US010646524B2

(12) United States Patent
Hwang et al.

(10) Patent No.: US 10,646,524 B2
(45) Date of Patent: May 12, 2020

(54) MODIFIED ONCOLYTIC VACCINIA VIRUSES EXPRESSING A CYTOKINE AND A CAR-BOXYLESTERASE AND METHODS OF USE THEREOF

(71) Applicant: SillaJen, Inc., Busan (KR)

(72) Inventors: Tae Ho Hwang, Busan (KR); Nam Hee Lee, Busan (KR); Euna Cho, Gyeongsangnam-do (KR)

(73) Assignee: SILLAJEN, INC., Busan (KR)

(*) Notice: Subject to any disclaimer, the term of this patent is extended or adjusted under 35 U.S.C. 154(b) by 0 days.

(21) Appl. No.: 15/758,689

(22) PCT Filed: Sep. 2, 2016

(86) PCT No.: PCT/KR2016/009866
§ 371 (c)(1),
(2) Date: Mar. 8, 2018

(87) PCT Pub. No.: WO2017/043815
PCT Pub. Date: Mar. 16, 2017

(65) Prior Publication Data
US 2018/0271921 A1    Sep. 27, 2018

Related U.S. Application Data

(60) Provisional application No. 62/215,651, filed on Sep. 8, 2015.

(51) Int. Cl.

| | | |
|---|---|---|
| *A61K 35/768* | (2015.01) | |
| *C07K 14/565* | (2006.01) | |
| *C12N 9/18* | (2006.01) | |
| *A61K 31/7068* | (2006.01) | |
| *C07K 14/52* | (2006.01) | |
| *A61K 31/513* | (2006.01) | |
| *A61K 31/519* | (2006.01) | |
| *A61K 31/337* | (2006.01) | |
| *A61K 31/4745* | (2006.01) | |
| *A61K 31/282* | (2006.01) | |
| *A61K 35/00* | (2006.01) | |
| *A61K 38/21* | (2006.01) | |
| *A61K 48/00* | (2006.01) | |
| *A61P 35/00* | (2006.01) | |

(52) U.S. Cl.
CPC .......... *A61K 35/768* (2013.01); *A61K 31/282* (2013.01); *A61K 31/337* (2013.01); *A61K 31/4745* (2013.01); *A61K 31/513* (2013.01); *A61K 31/519* (2013.01); *A61K 31/7068* (2013.01); *A61K 38/215* (2013.01); *A61P 35/00* (2018.01); *C07K 14/52* (2013.01); *C07K 14/565* (2013.01); *C12N 9/18* (2013.01); *C12Y 301/01001* (2013.01); *A61K 48/005* (2013.01); *C12N 2710/24132* (2013.01); *C12N 2710/24134* (2013.01); *C12N 2710/24141* (2013.01); *C12N 2710/24143* (2013.01)

(58) Field of Classification Search
CPC ................ A61K 35/768; A61K 31/282; A61K 31/7068; A61K 38/214; A61K 48/005; C07K 14/52; C07K 14/565; C12Y 301/01001; C12N 9/18; C12N 2710/24132; C12N 2710/24143; C12N 2710/24141
USPC ................... 514/44 R; 424/199.1; 435/320.1
See application file for complete search history.

(56) References Cited

U.S. PATENT DOCUMENTS 8,329,164 B2 * 12/2012 Kim ........................ A61K 45/06
424/93.3

FOREIGN PATENT DOCUMENTS

WO    WO 2012094386    *    1/2012

OTHER PUBLICATIONS

Michelle Caitlin Becker (2013) "The Combination of Carboxylesterase-Expressing Oncolytic Vaccinia Virus and Irinotecan", Thesis, pp. 1-136, University of Ottawa, http://hdl.handle.net/10393/23653 http://dx.doi.org/10.20381/ruor-6378.*
Xu et al. (2002) Clin. Canc. Res., vol. 8, 2605-2611.*
Kim et al. (2007) PLoS, vol. 4 (12) e353, pp. 2001-2012.*
Nishikawa et al. (2000) FEBS Letters, vol. 466, 179-182.*

* cited by examiner

*Primary Examiner* — Anne Marie S Wehbe
(74) *Attorney, Agent, or Firm* — Polsinelli PC; Christopher M. Cabral

(57) ABSTRACT

The present disclosure pertains to a compositions and combinations for simultaneous, separate or sequential use which comprises (a) an oncolytic vaccinia virus that expresses a cytokine and a carboxylesterase enzyme, and, preferably, (b) a cancer co-drug, and to their uses for the treatment of cancer.

21 Claims, 25 Drawing Sheets
Specification includes a Sequence Listing.

[Fig. 1A]
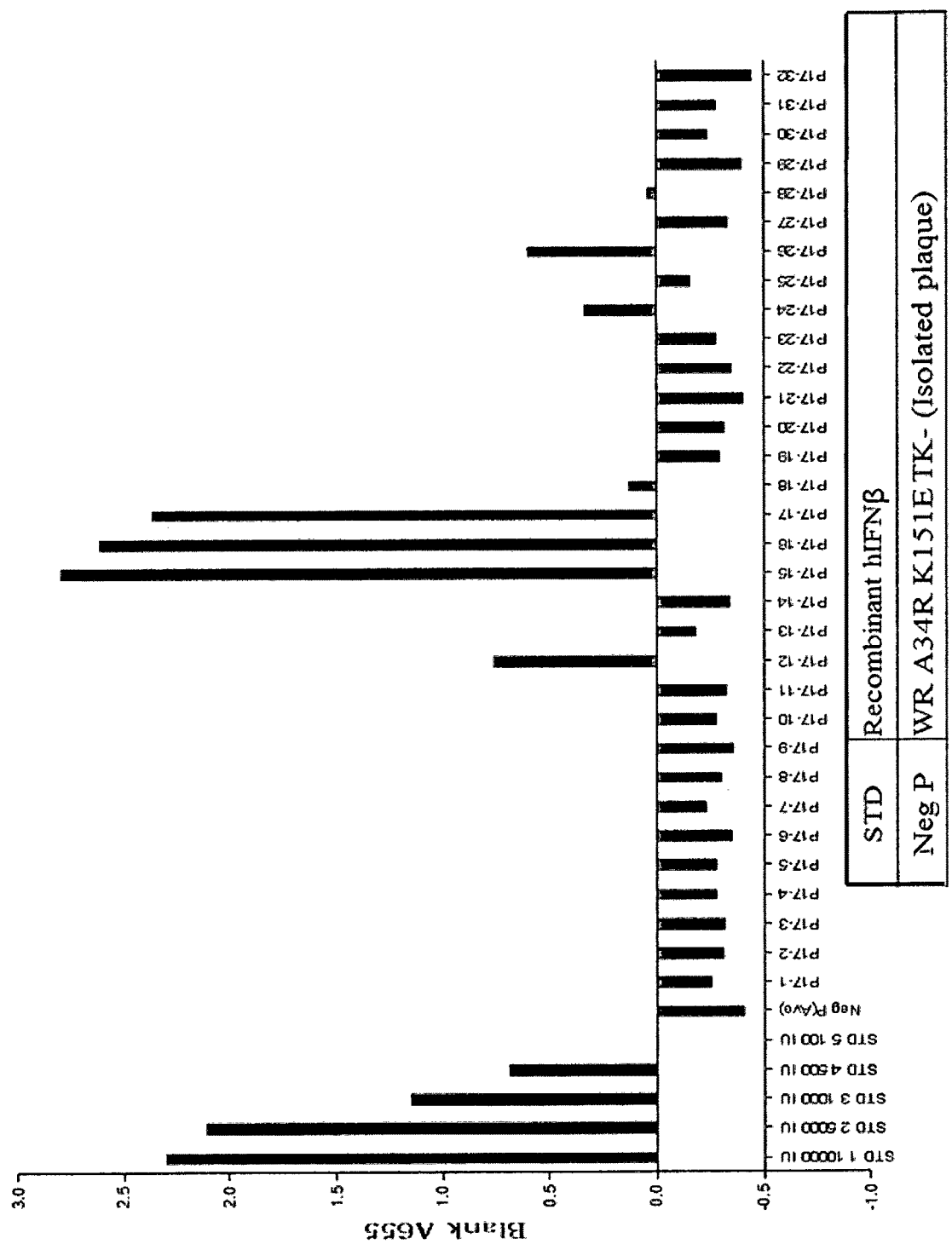

[Fig. 1B]
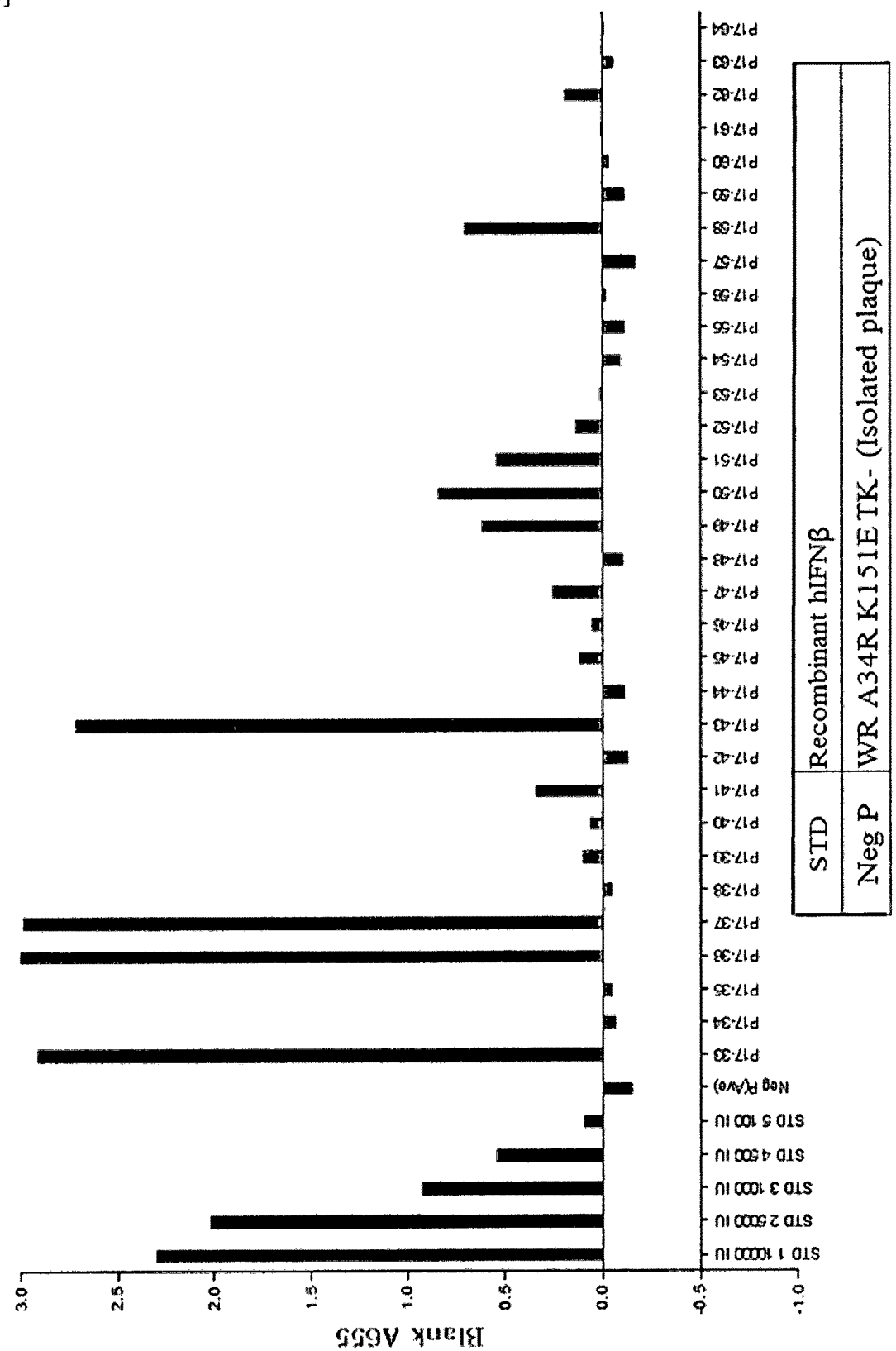

[Fig. 1C]
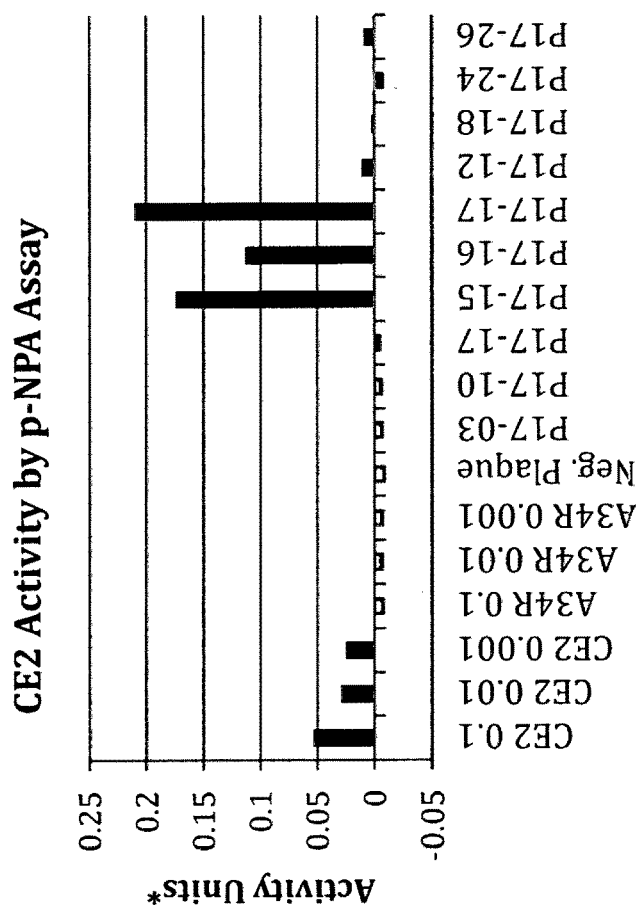

[Fig. 1D]
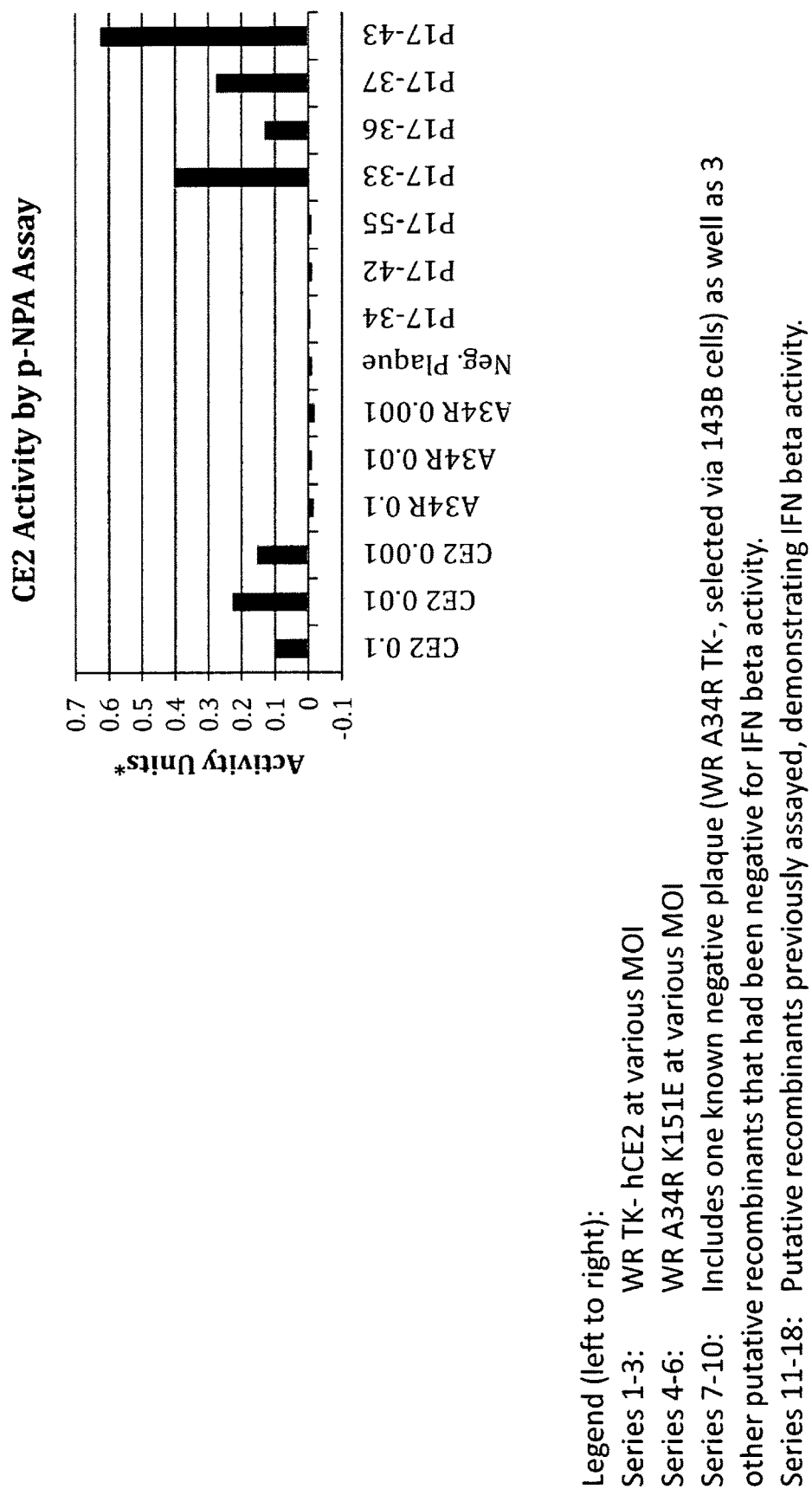
legend (left to right):
Series 1-3: WR TK- hCE2 at various MOI
Series 4-6: WR A34R K151E at various MOI
Series 7-10: Includes one known negative plaque (WR A34R TK-, selected via 143B cells) as well as 3 other putative recombinants that had been negative for IFN beta activity.
Series 11-18: Putative recombinants previously assayed, demonstrating IFN beta activity.

[Fig. 2]
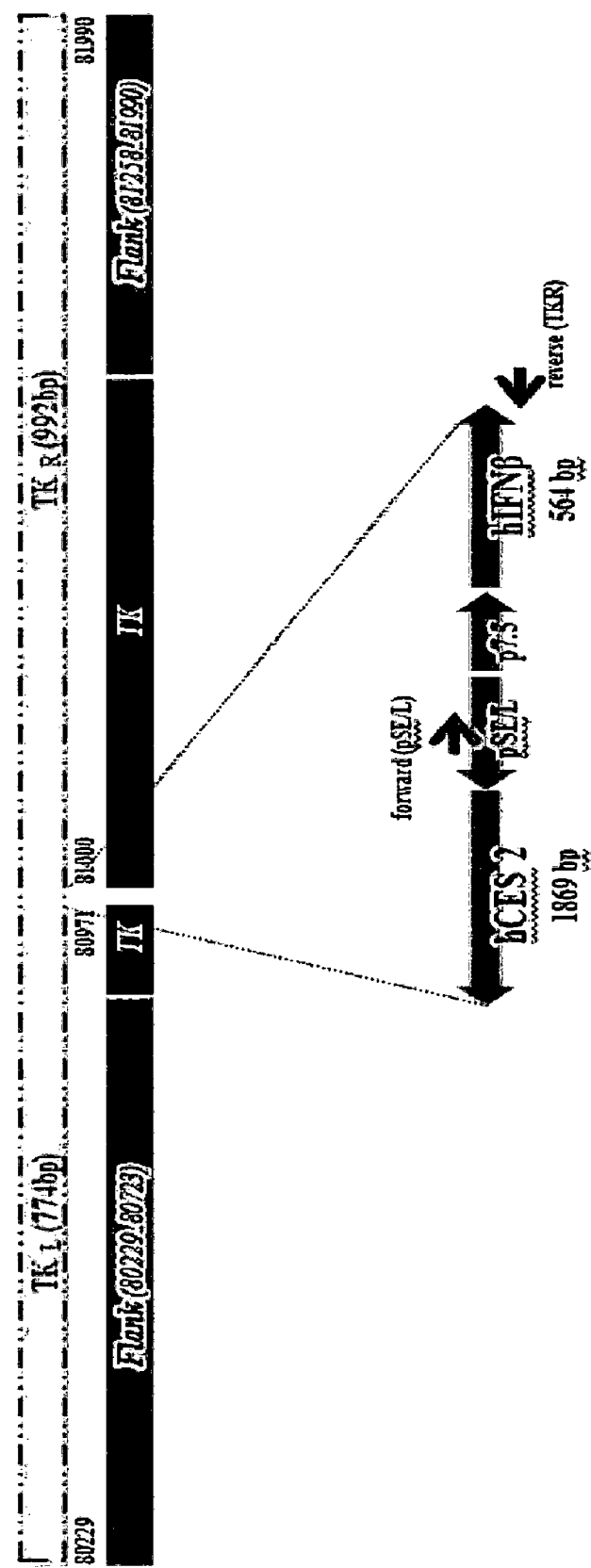

[Fig. 3A]
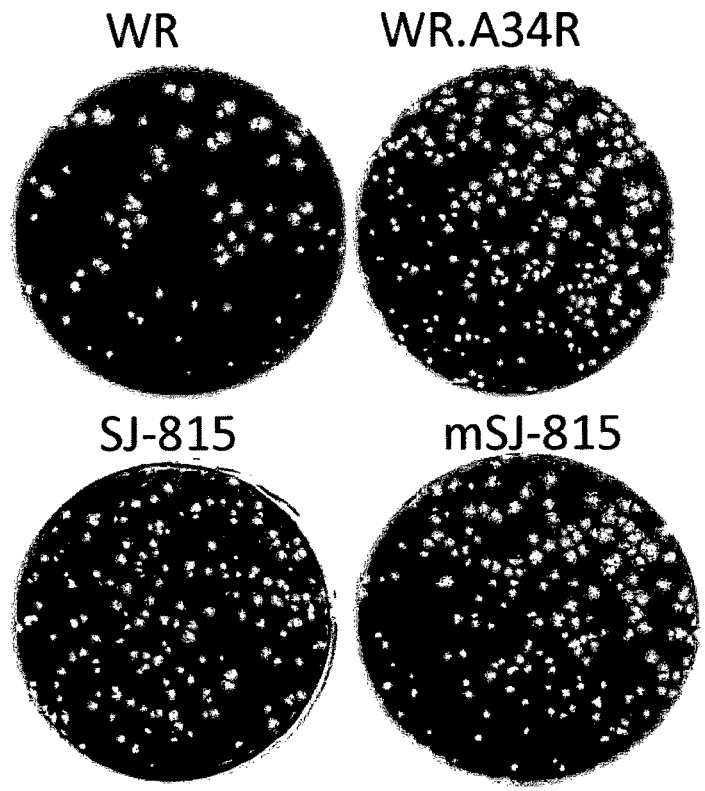
[Fig. 3B]
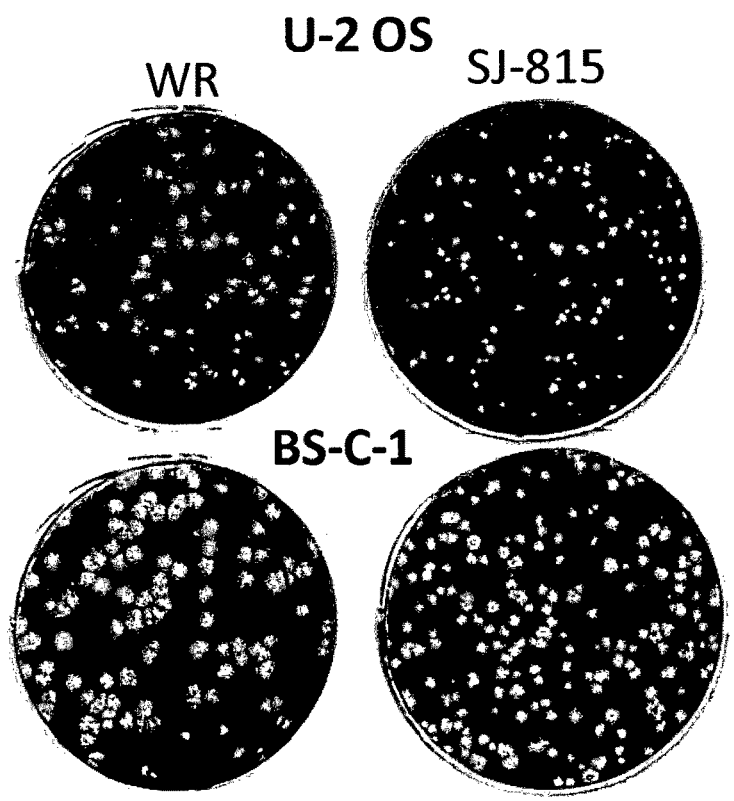

[Fig. 4A]
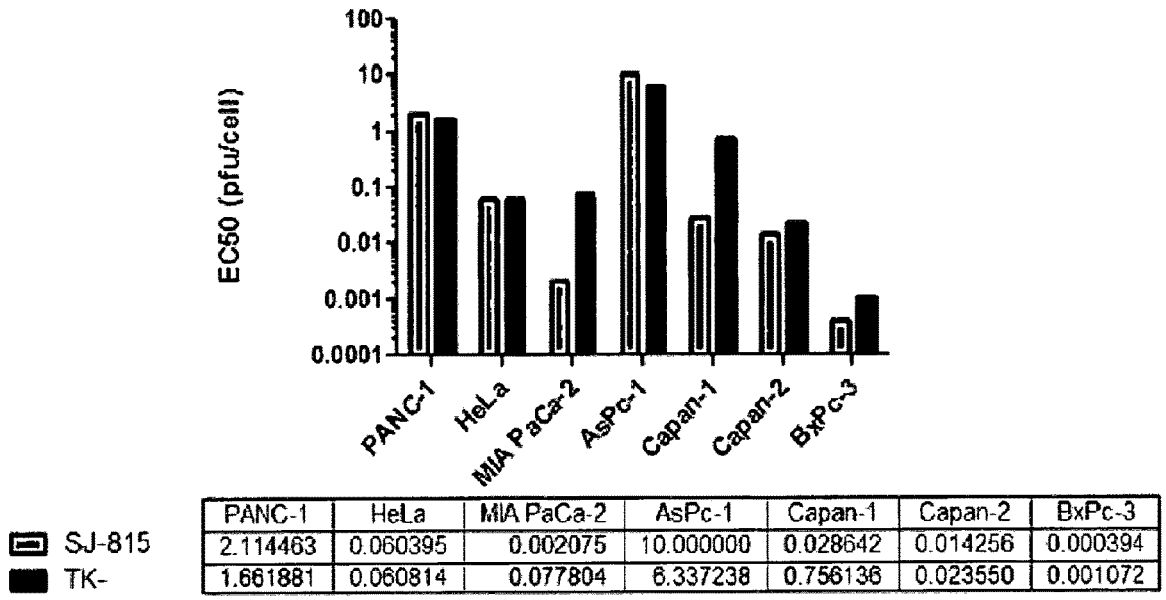
|  | PANC-1 | HeLa | MIA PaCa-2 | AsPc-1 | Capan-1 | Capan-2 | BxPc-3 |
|---|---|---|---|---|---|---|---|
| SJ-815 | 2.114463 | 0.060395 | 0.002075 | 10.000000 | 0.028642 | 0.014256 | 0.000394 |
| TK- | 1.661881 | 0.060814 | 0.077804 | 6.337238 | 0.756136 | 0.023550 | 0.001072 |
[Fig. 4B]
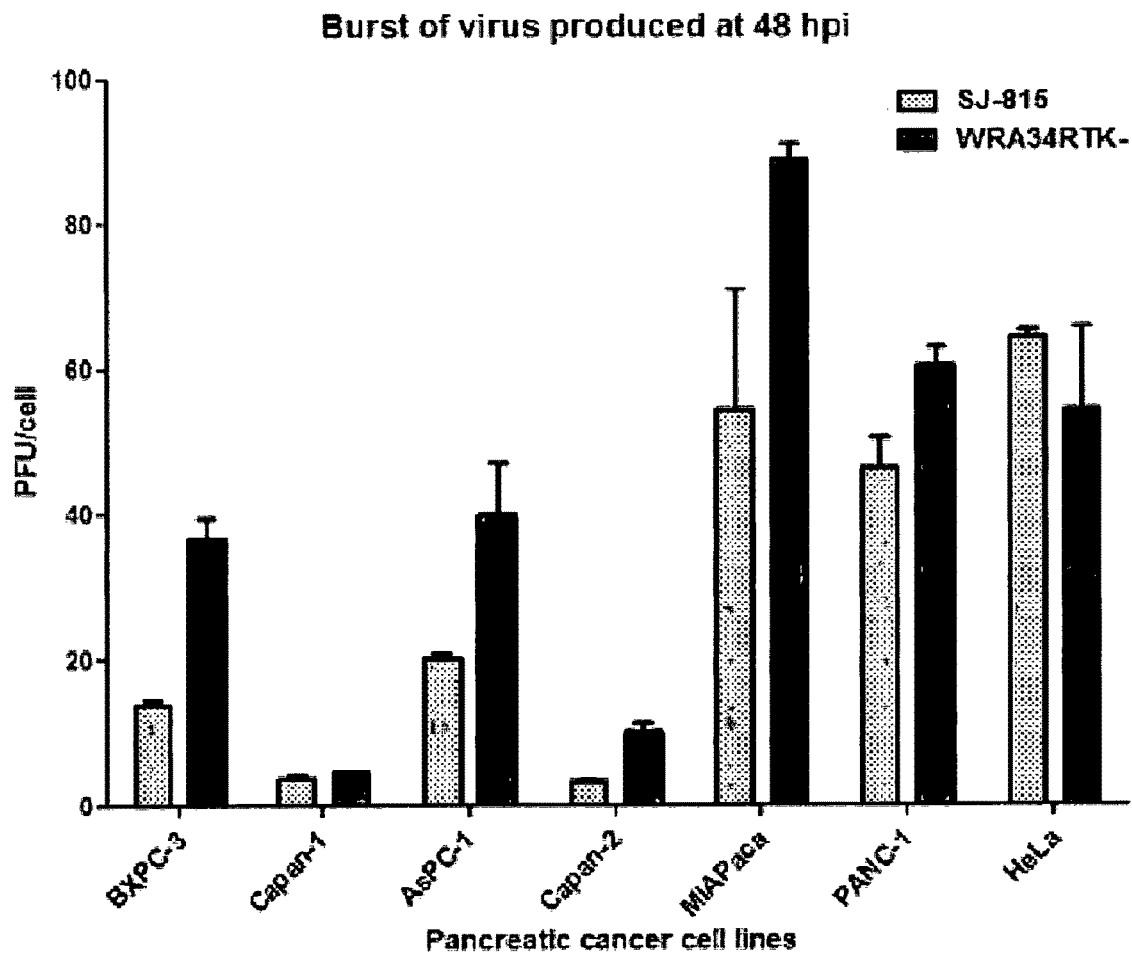

[Fig. 5A]
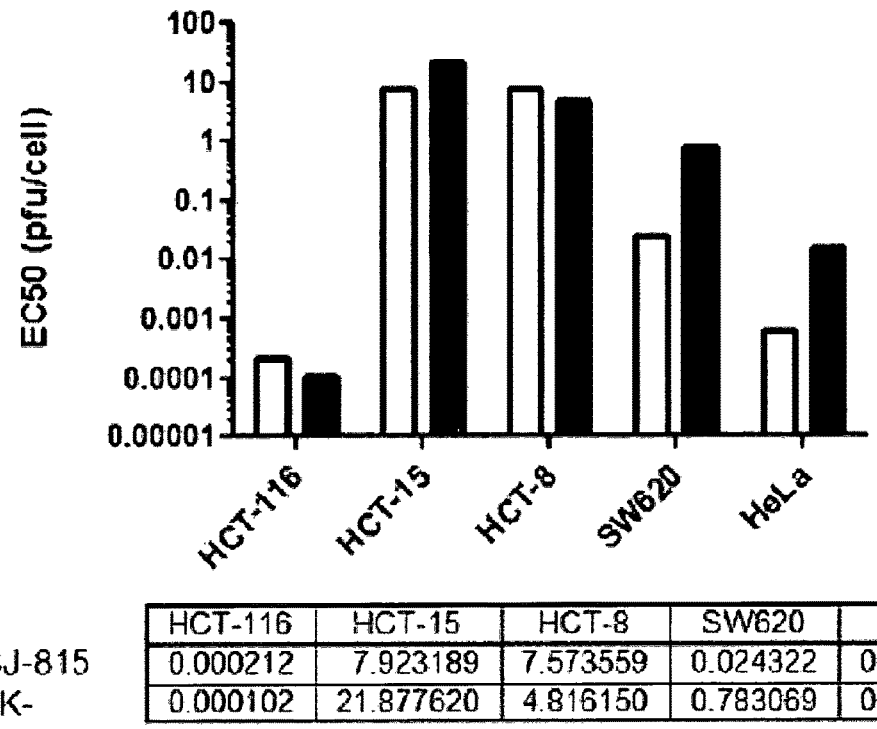
|  | HCT-116 | HCT-15 | HCT-8 | SW620 | HeLa |
|---|---|---|---|---|---|
| SJ-815 | 0.000212 | 7.923189 | 7.573559 | 0.024322 | 0.000624 |
| TK- | 0.000102 | 21.877620 | 4.816150 | 0.783069 | 0.016144 |
[Fig. 5B]
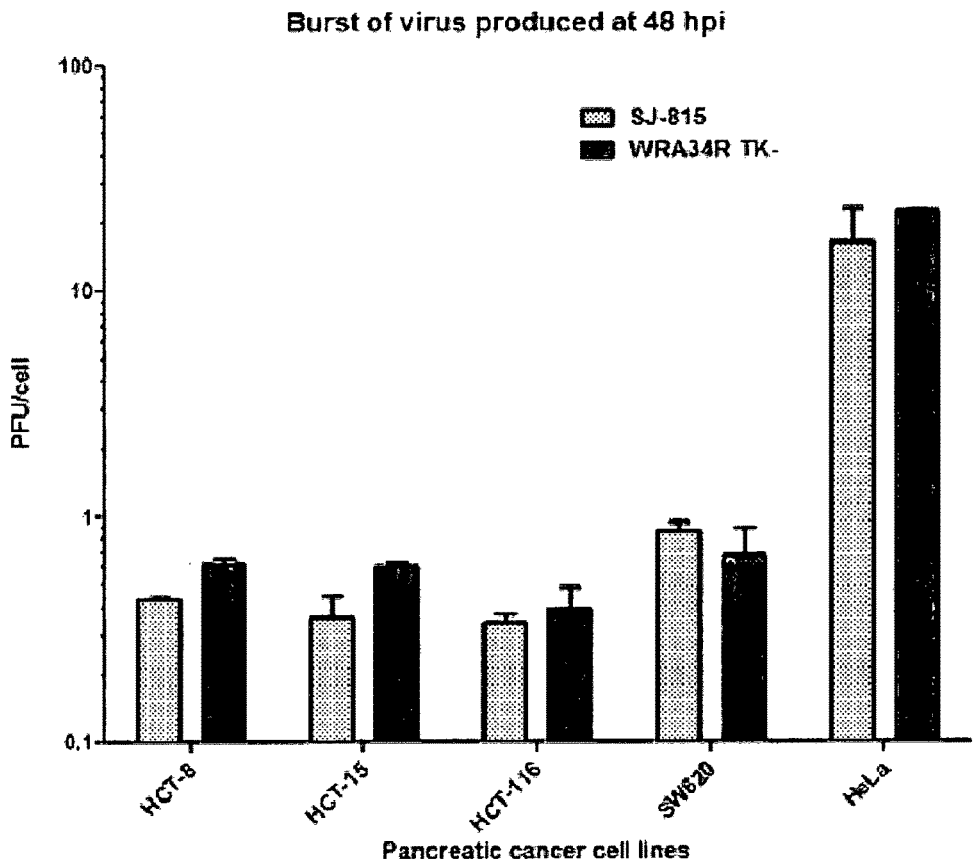

[Fig. 6A]
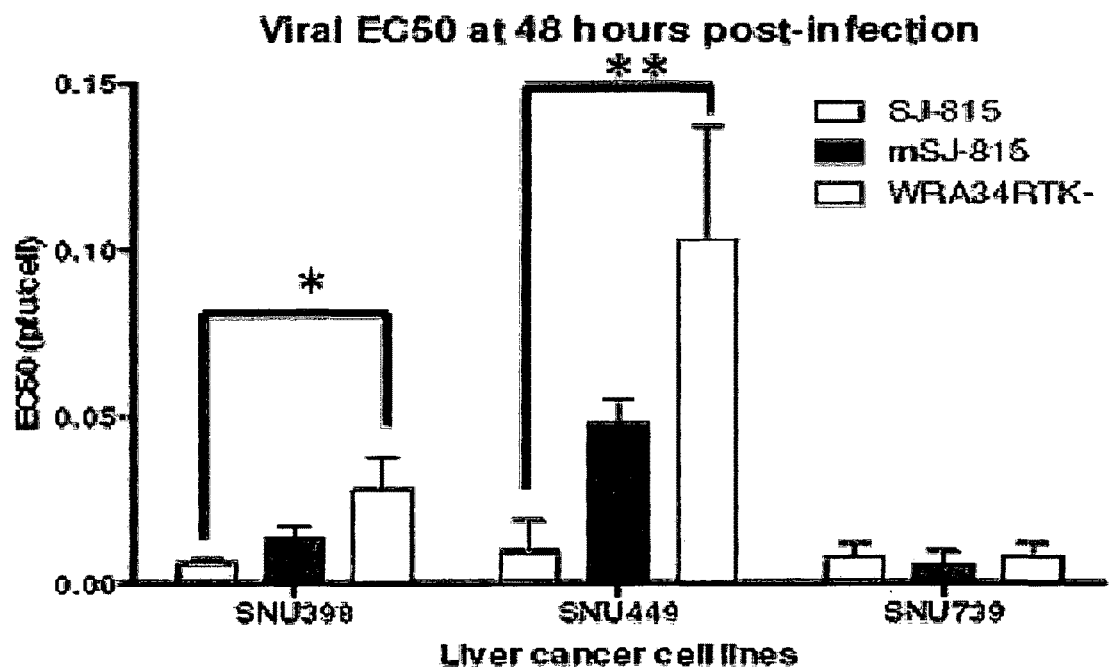
[Fig. 6B]
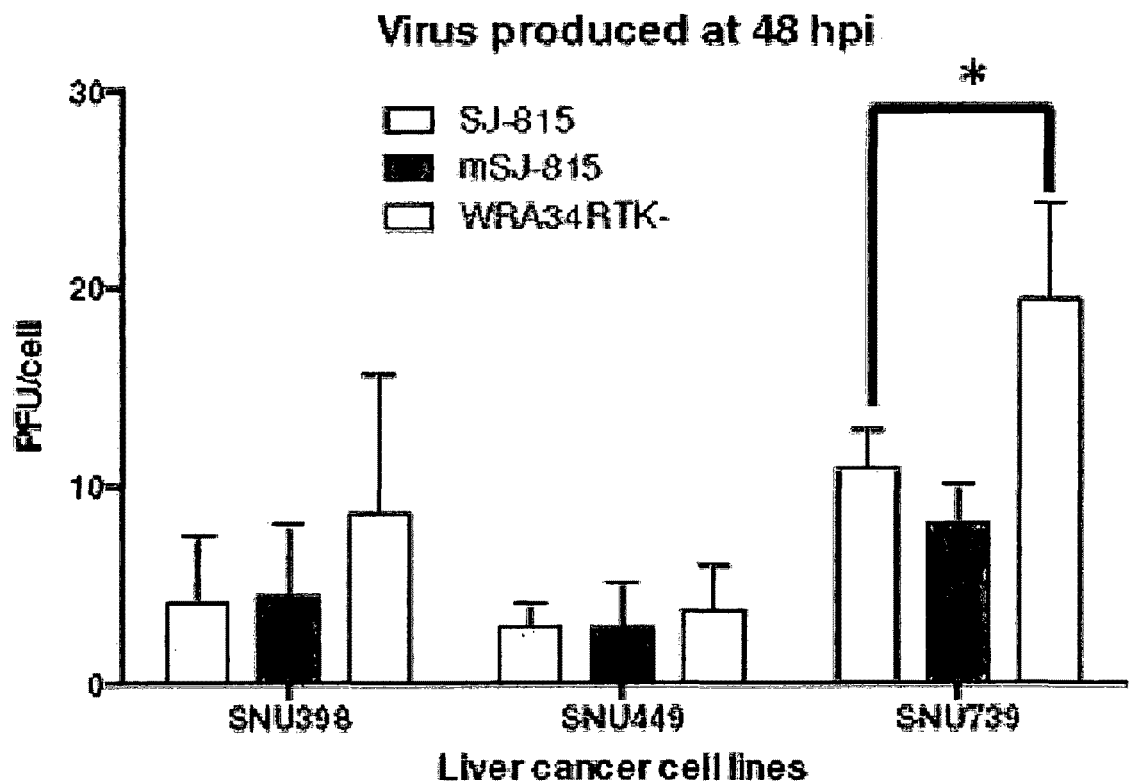

[Fig. 7A]
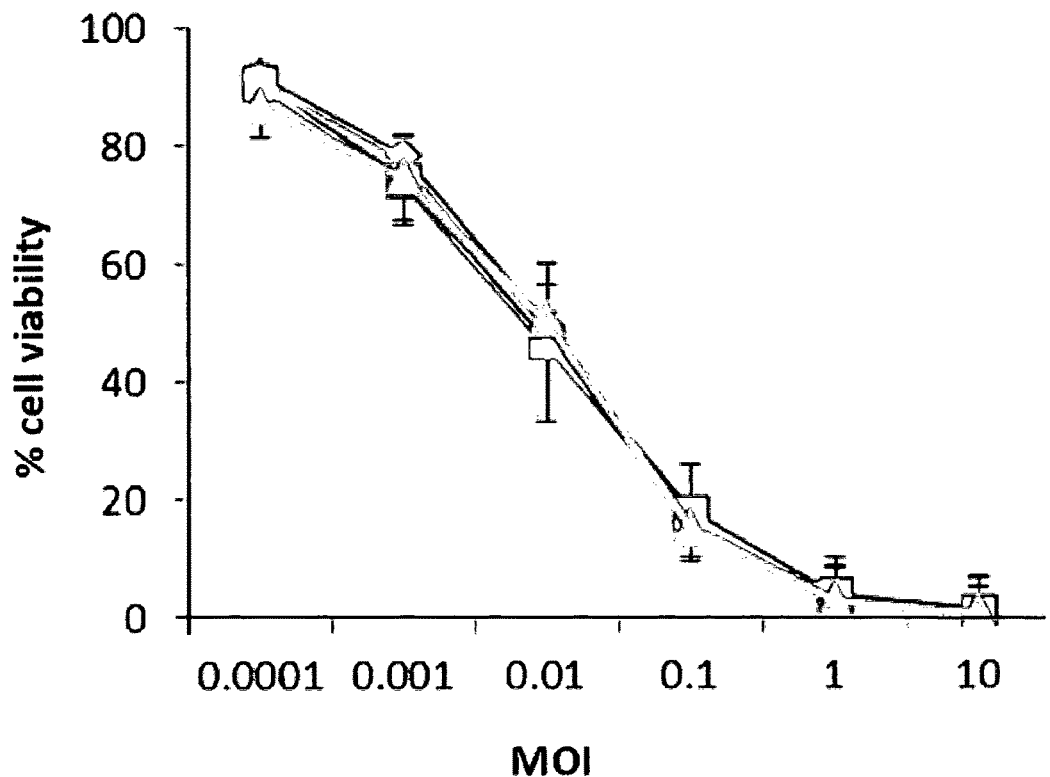
[Fig. 7B]
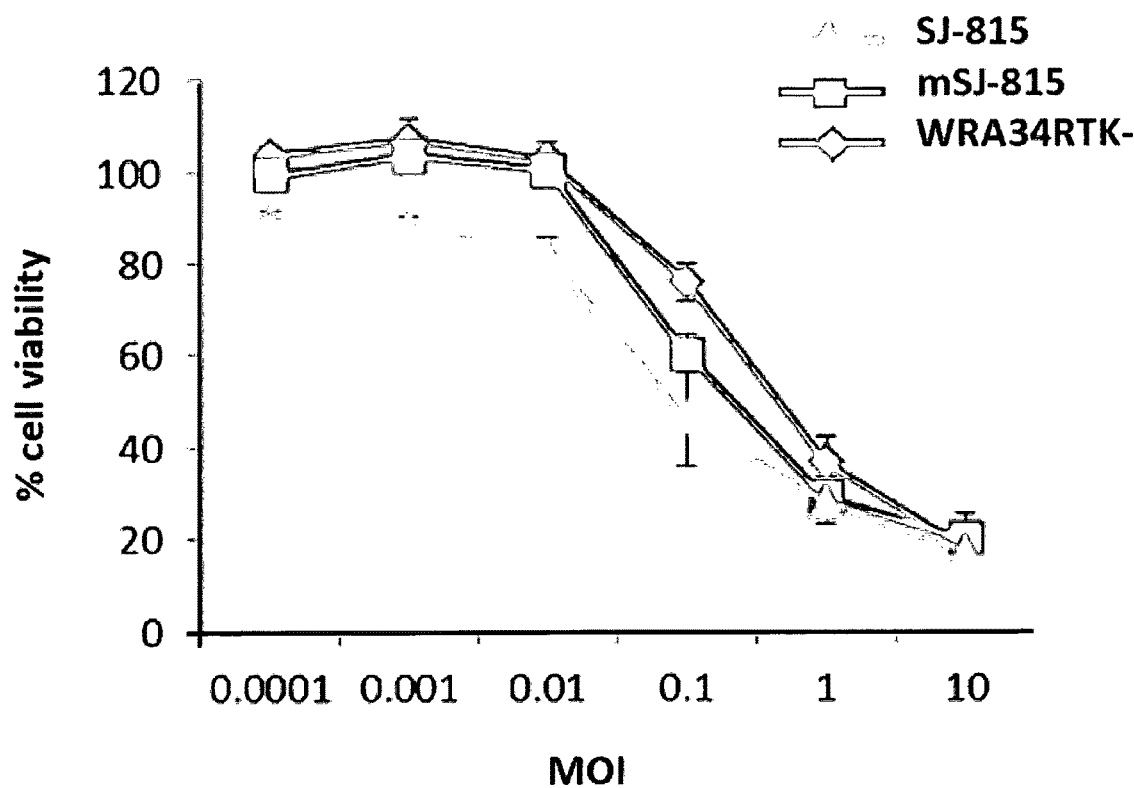

[Fig. 7C]
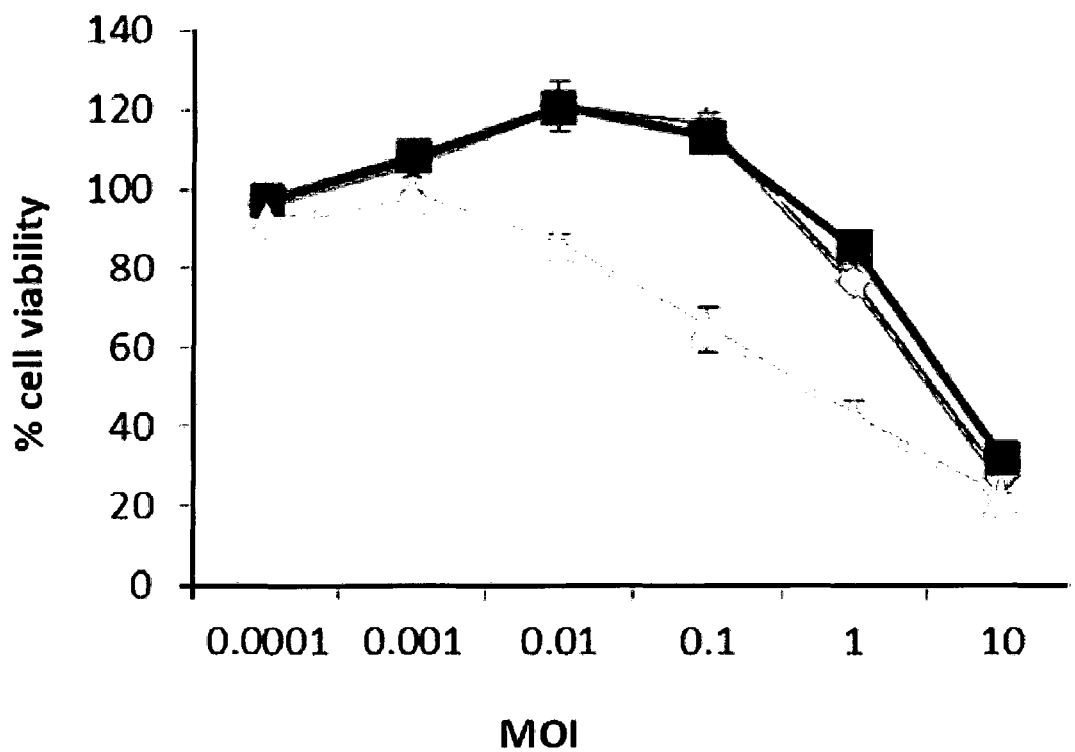
[Fig. 7D]
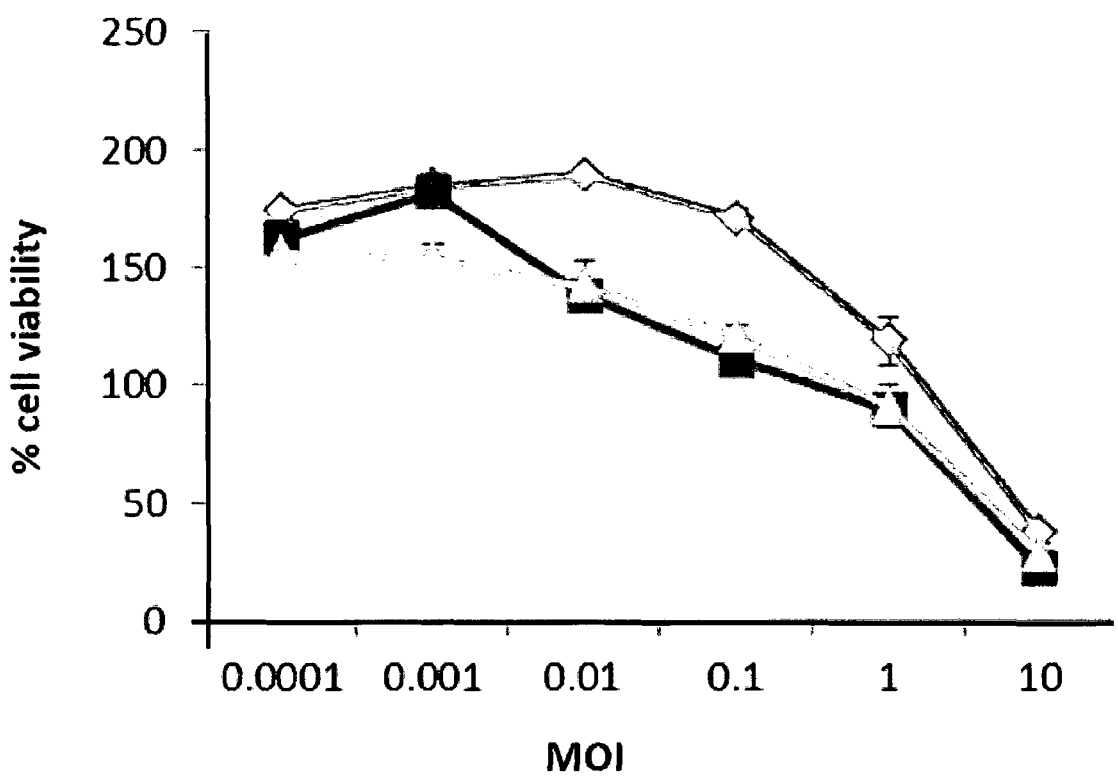

[Fig. 8]
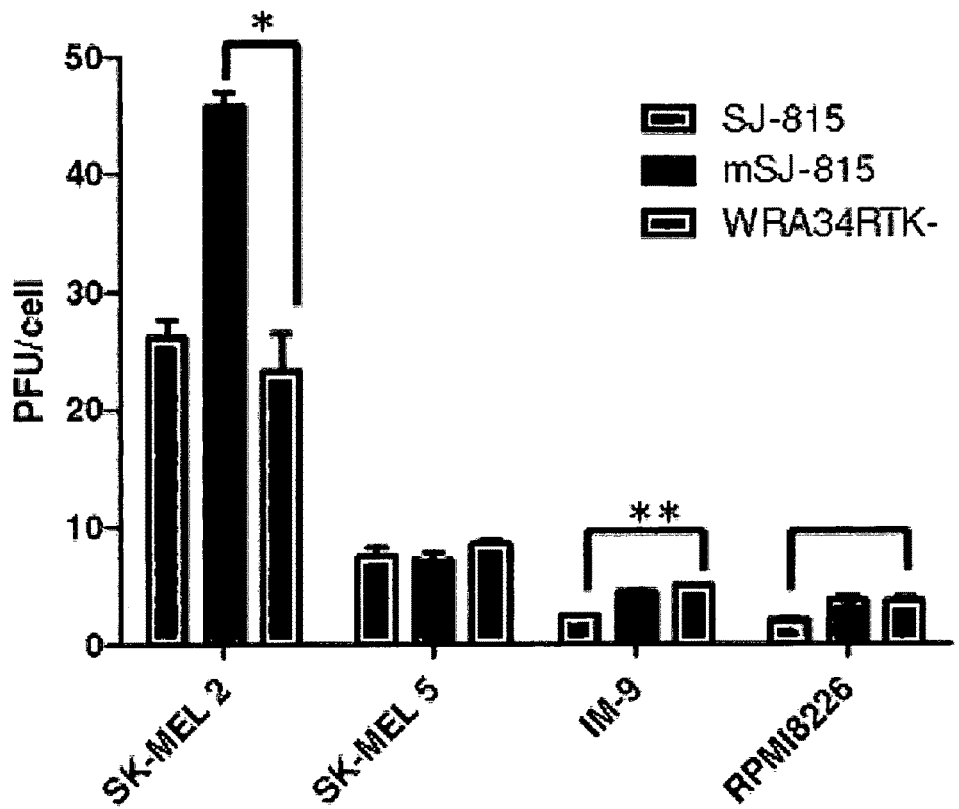
[Fig. 9A]
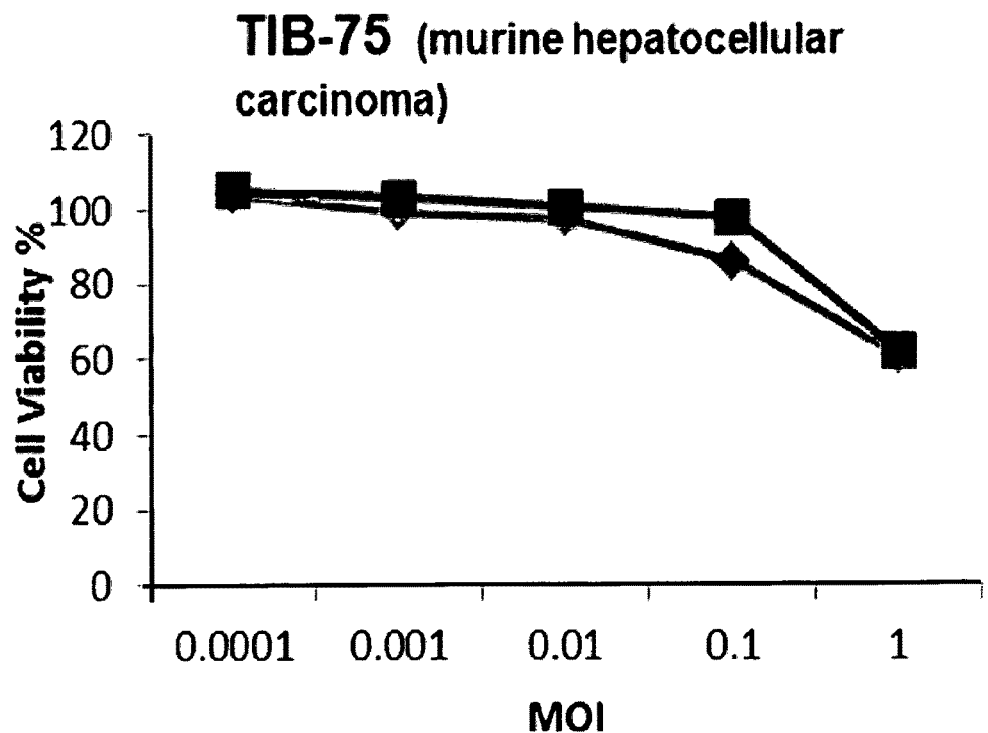

[Fig. 9B]
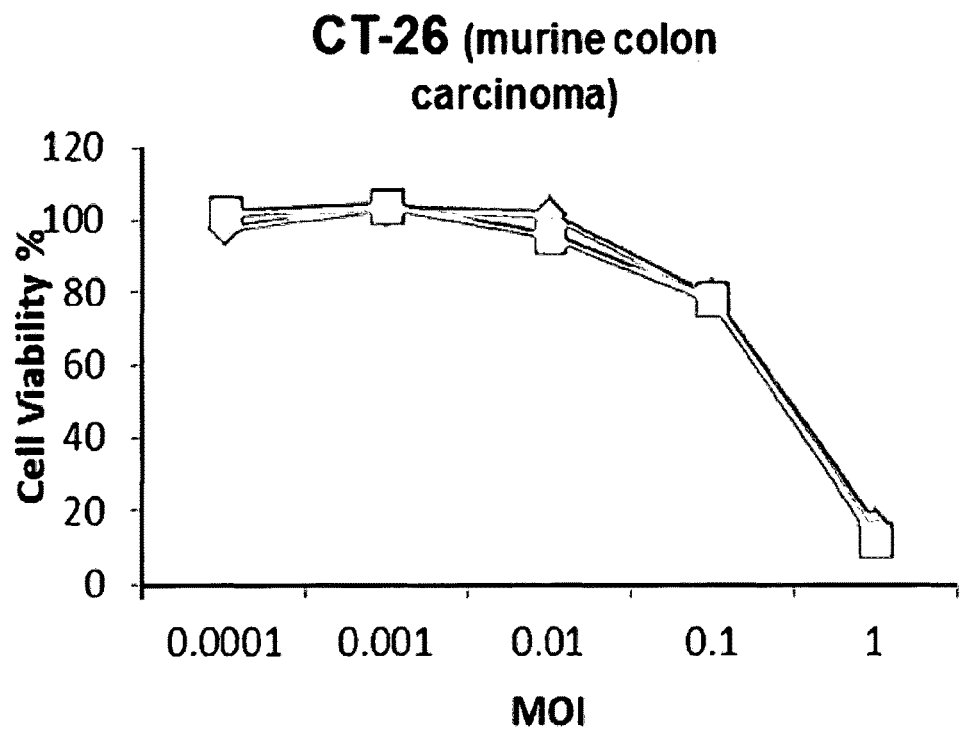
[Fig. 9C]
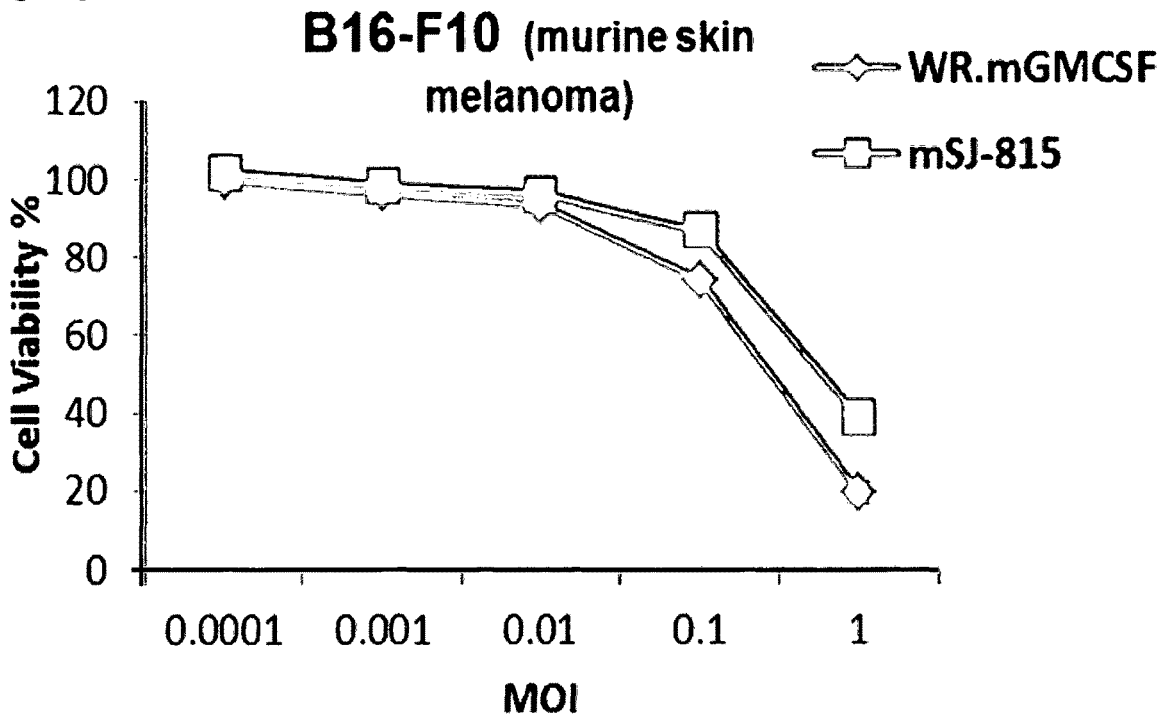

[Fig. 9D]
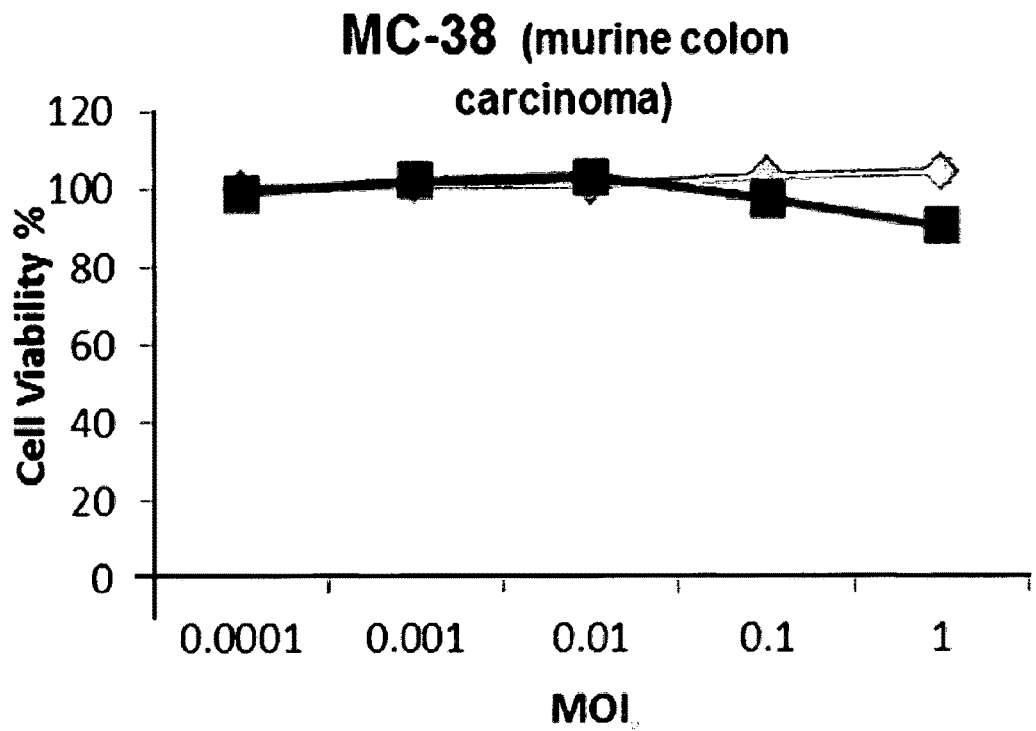
[Fig. 9E]
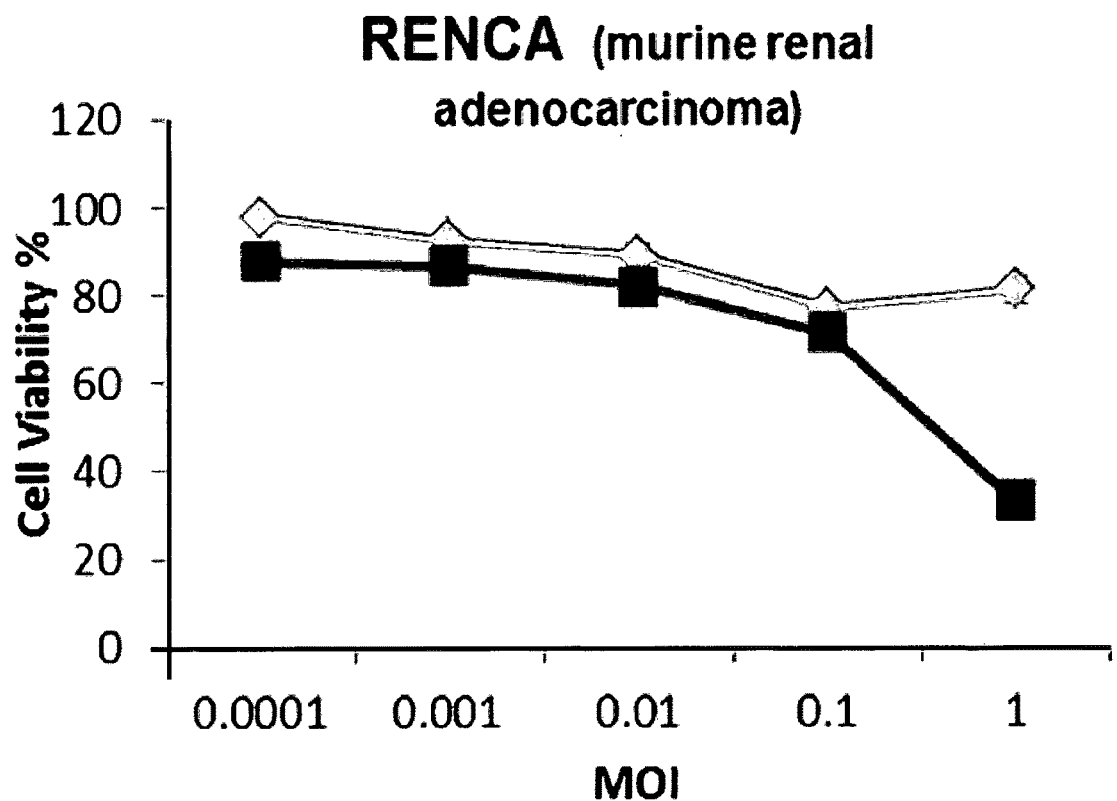

[Fig. 9F]
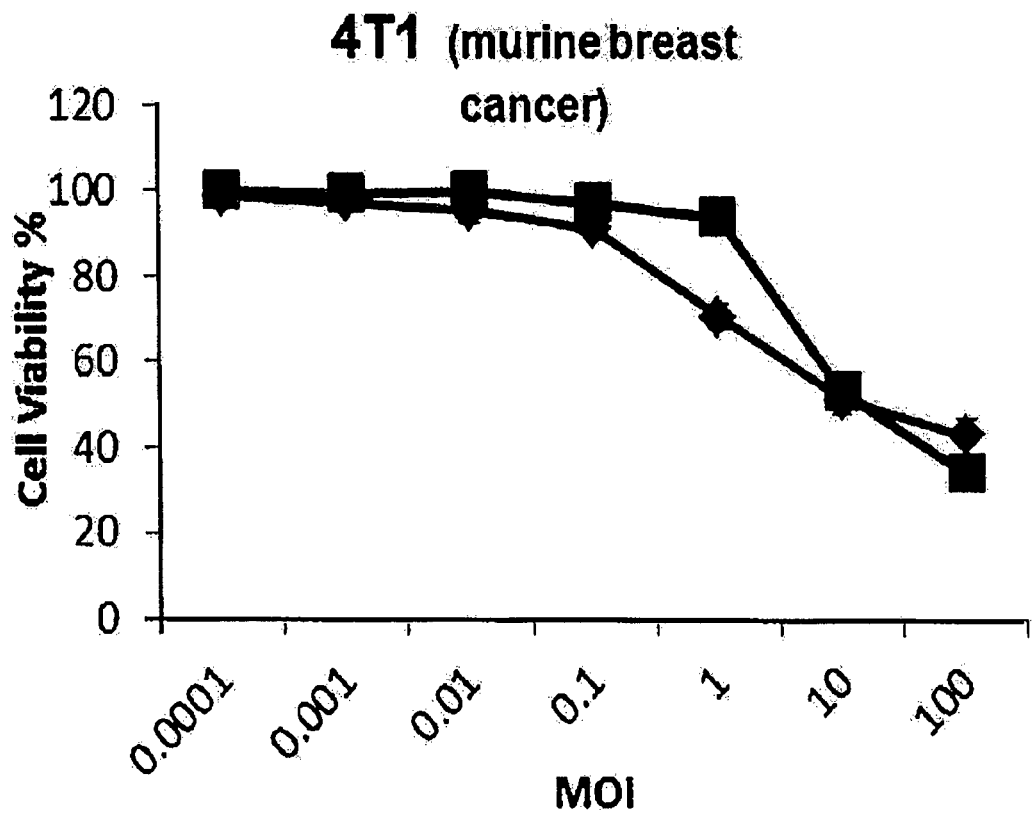
[Fig. 10A]
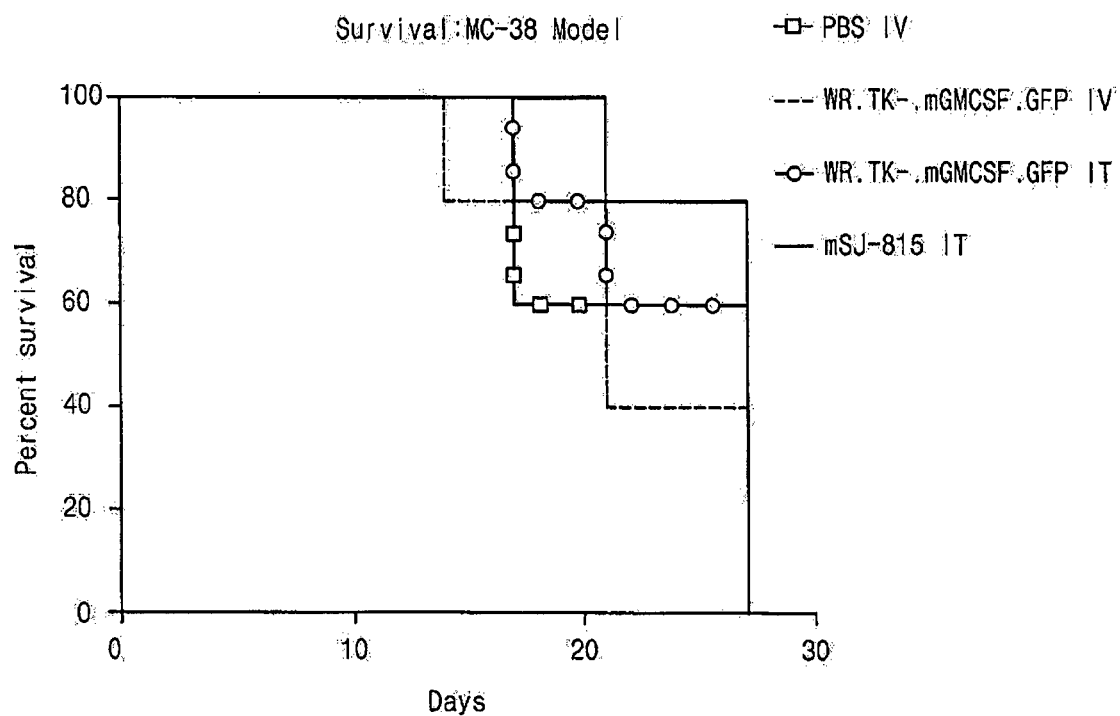

[Fig. 10B]
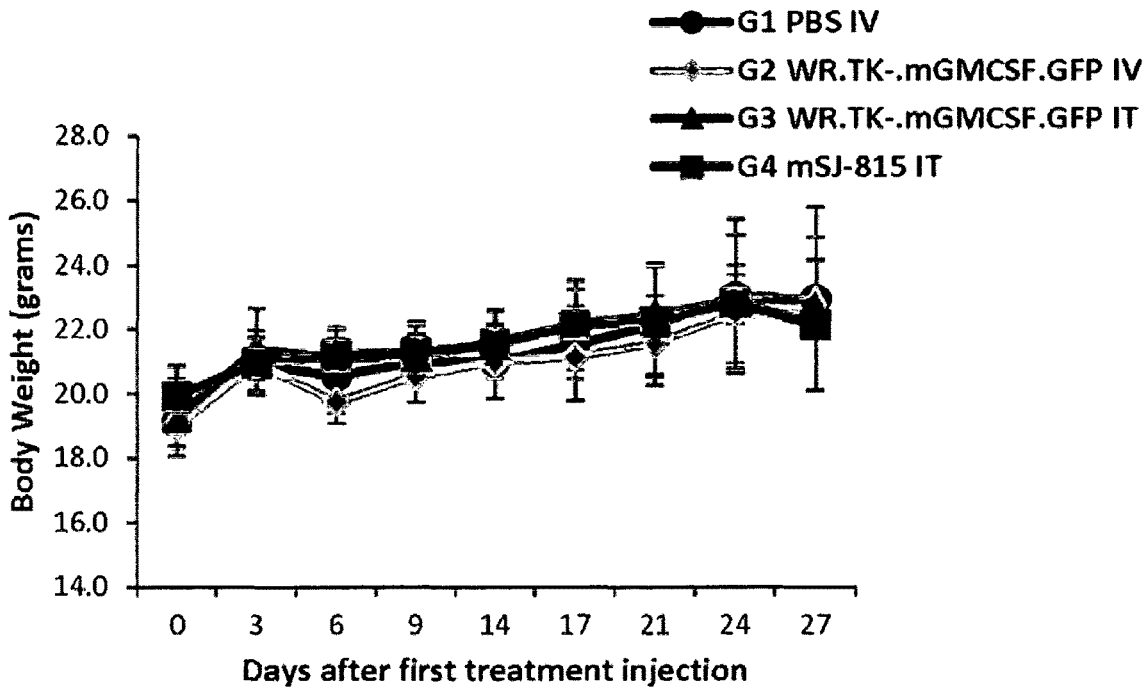
[Fig. 10C]
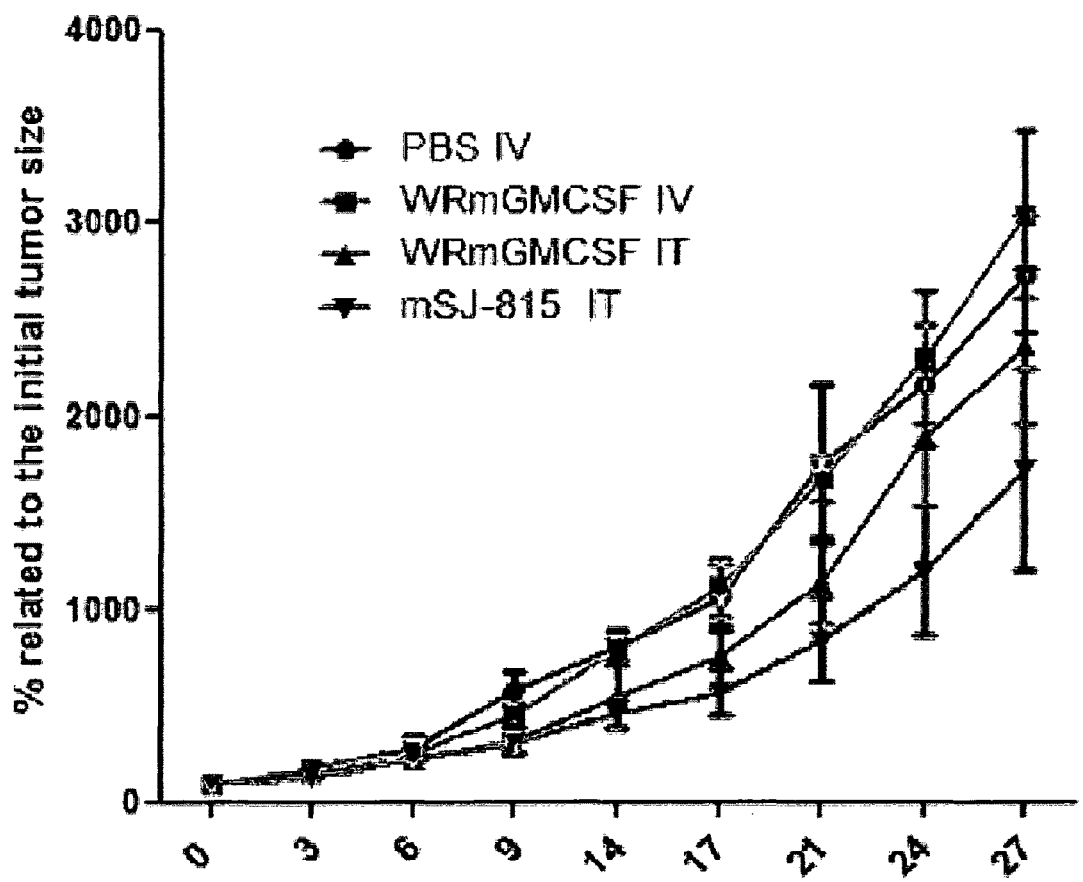

[Fig. 11]
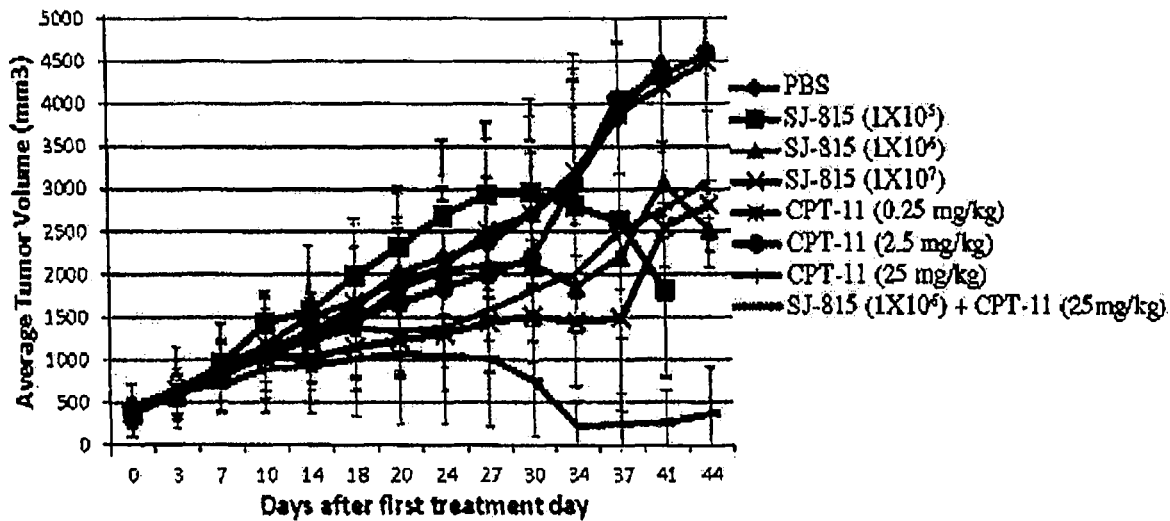
[Fig. 12A]
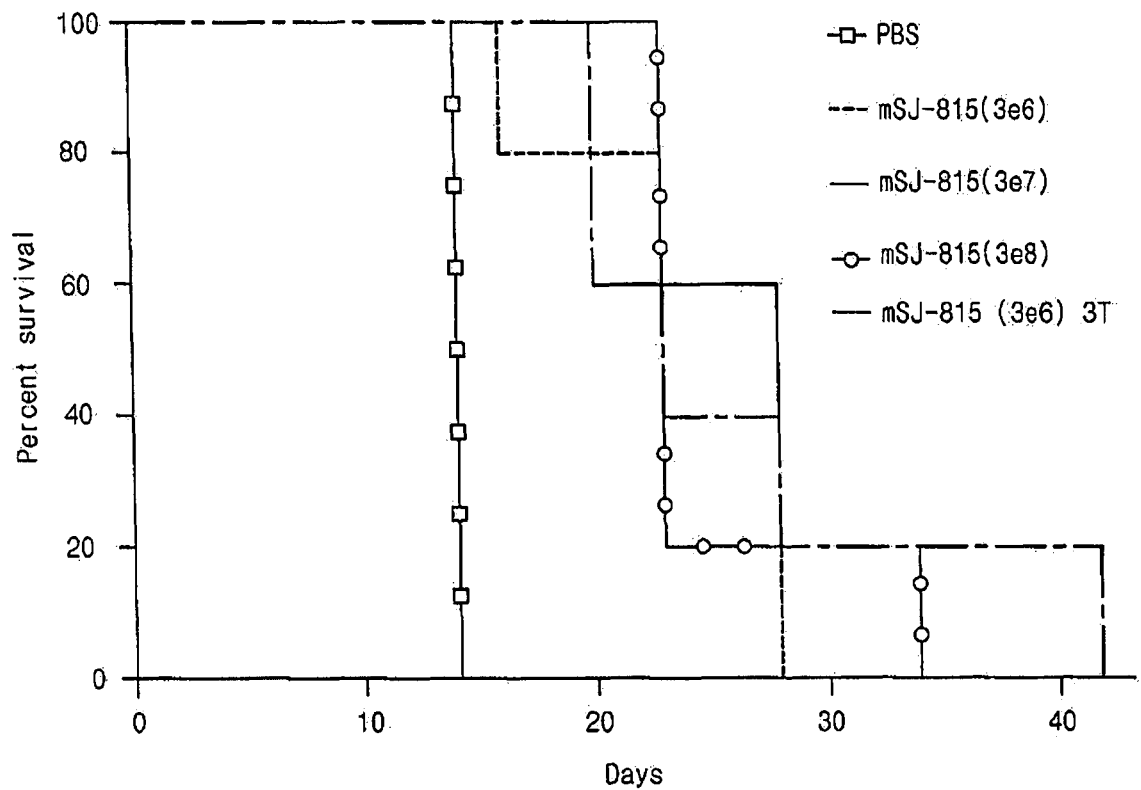

[Fig. 12B]
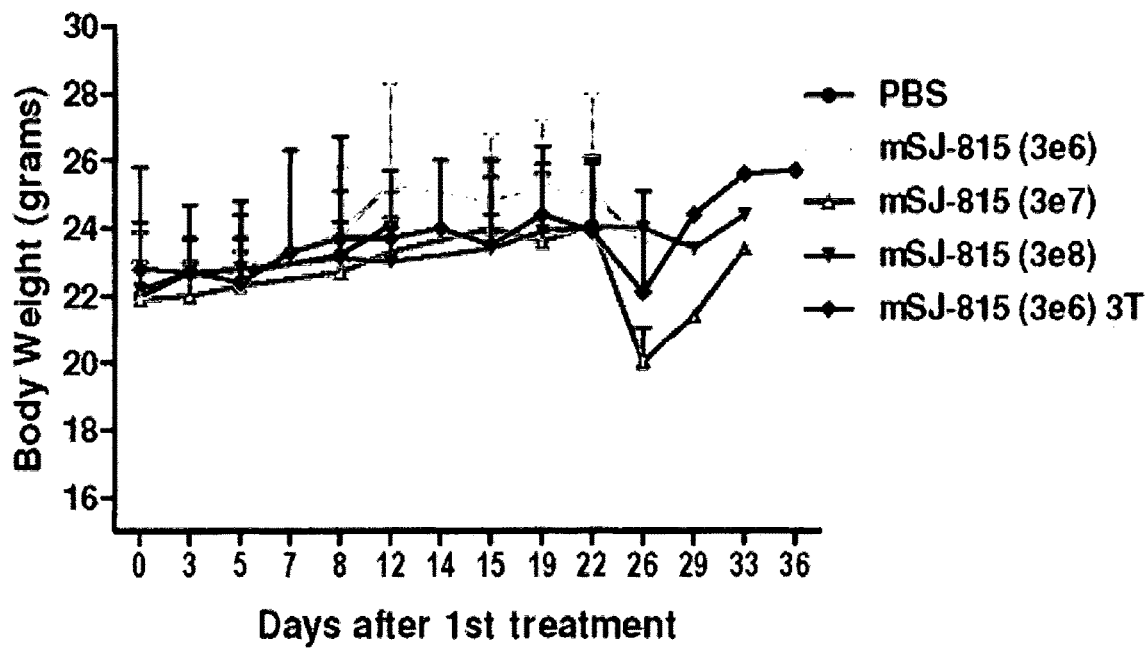
[Fig. 13A]
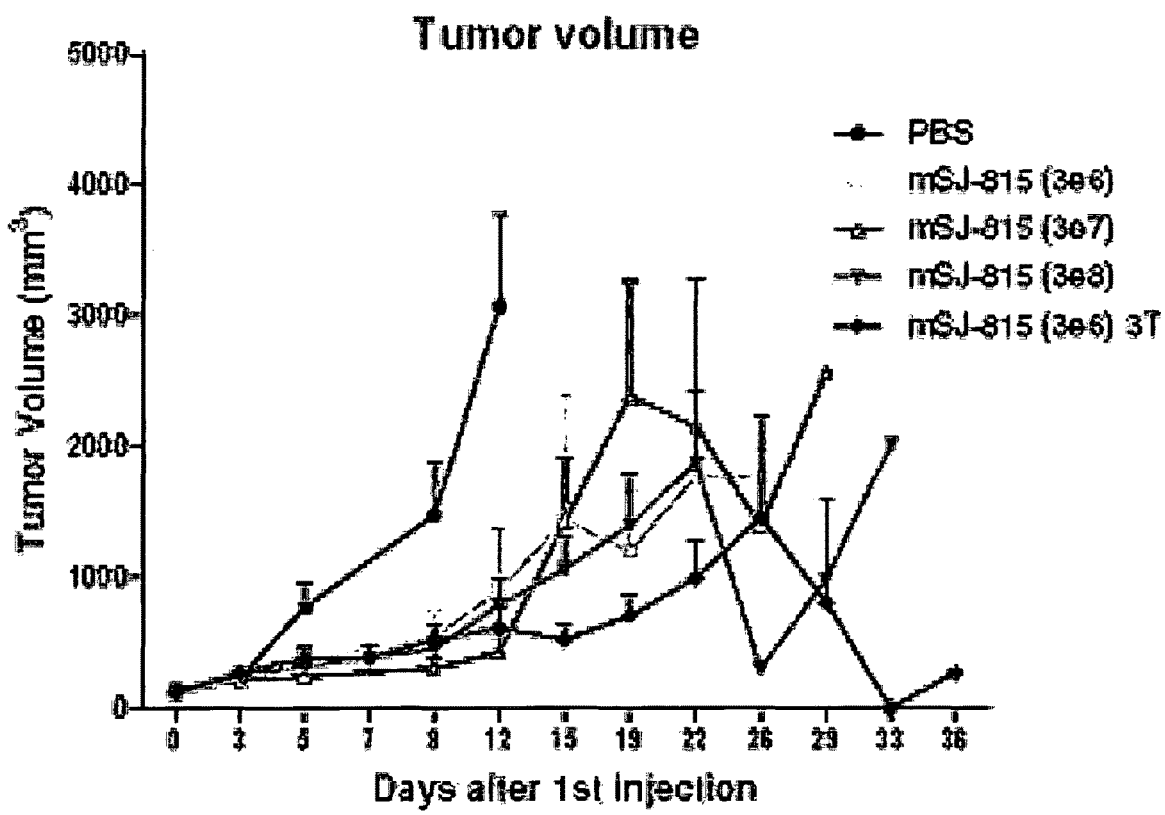

[Fig. 13B]
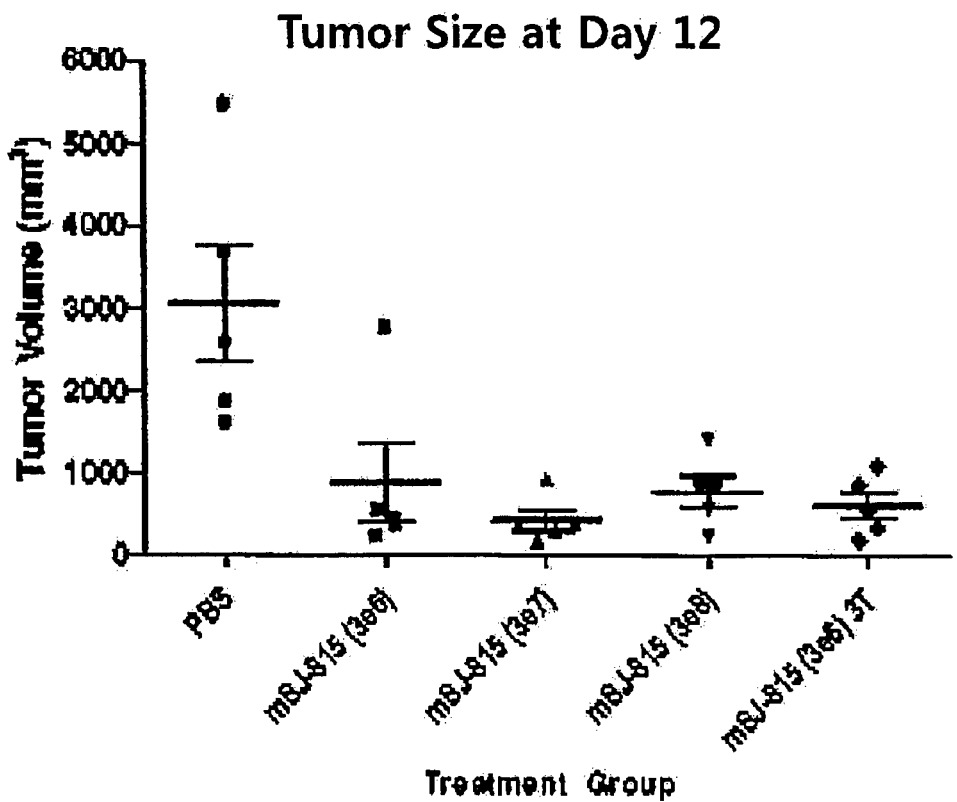
[Fig. 14]
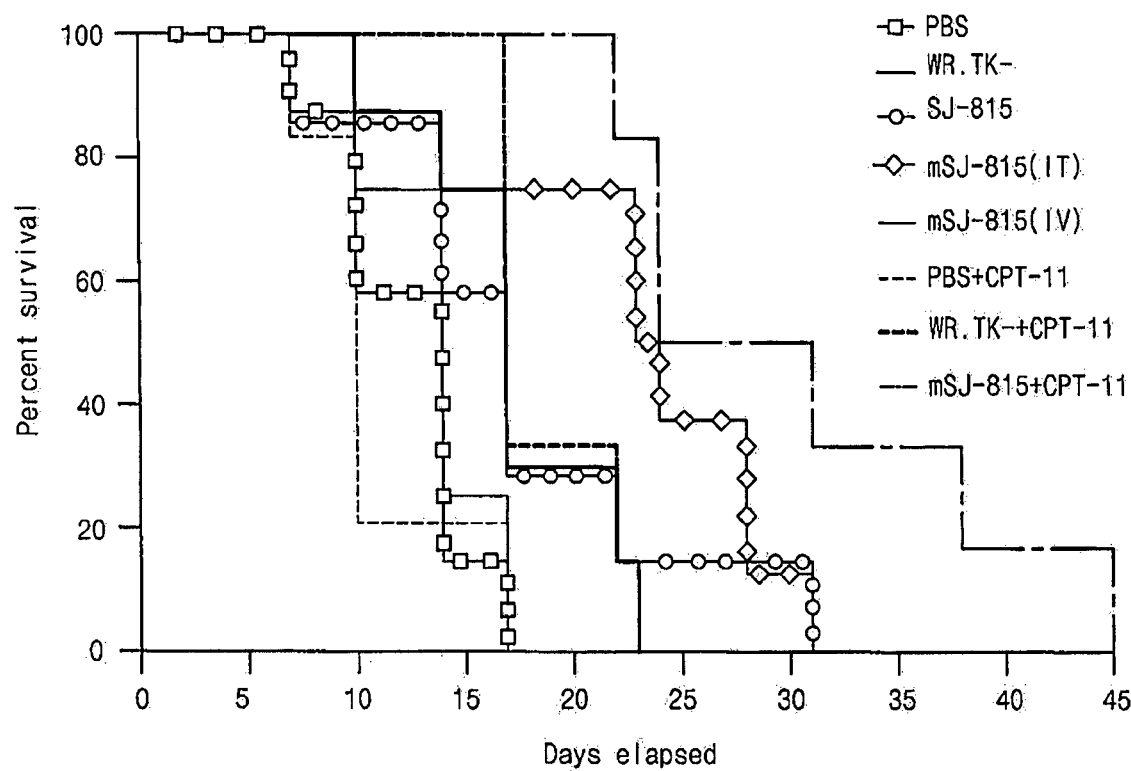

[Fig. 15A]
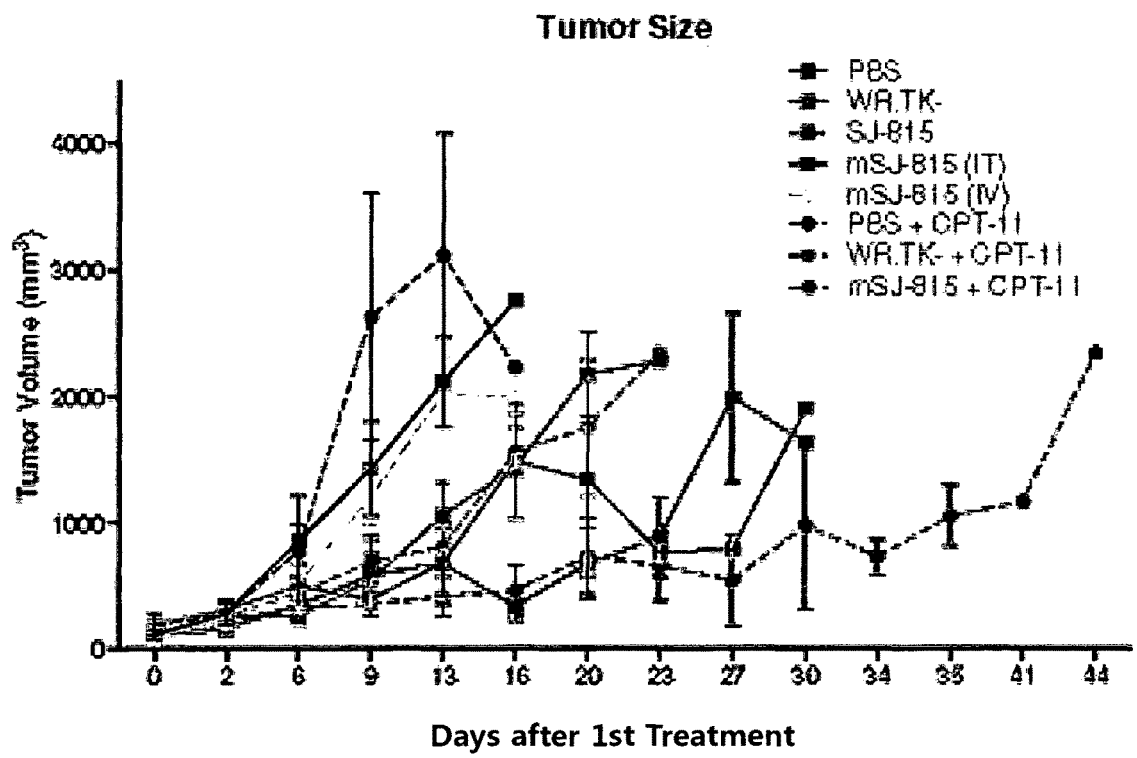
[Fig. 15B]
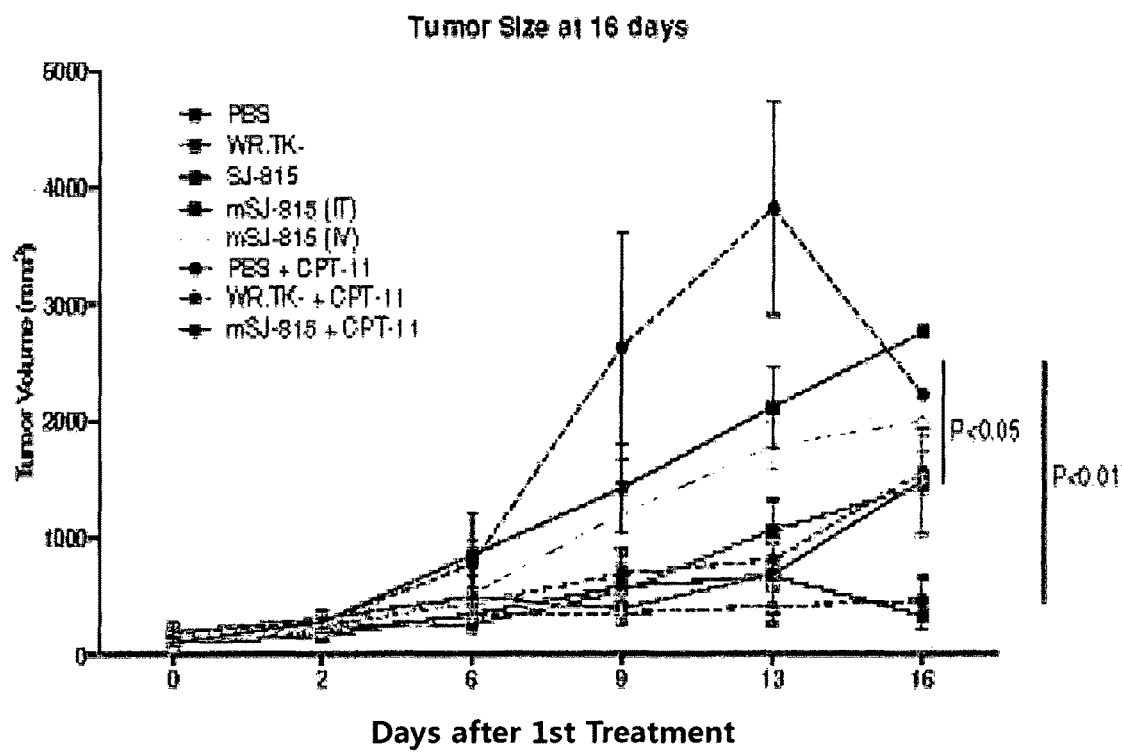

[Fig. 15C]
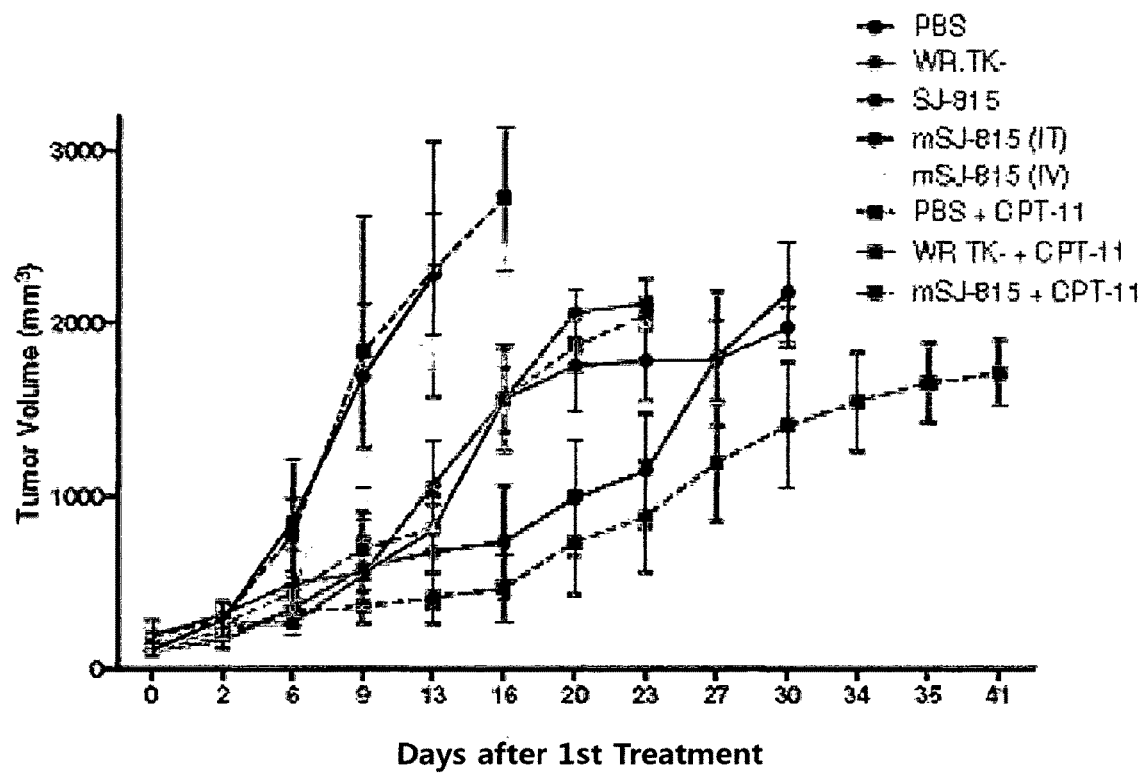
Days after 1st Treatment
[Fig. 15D]
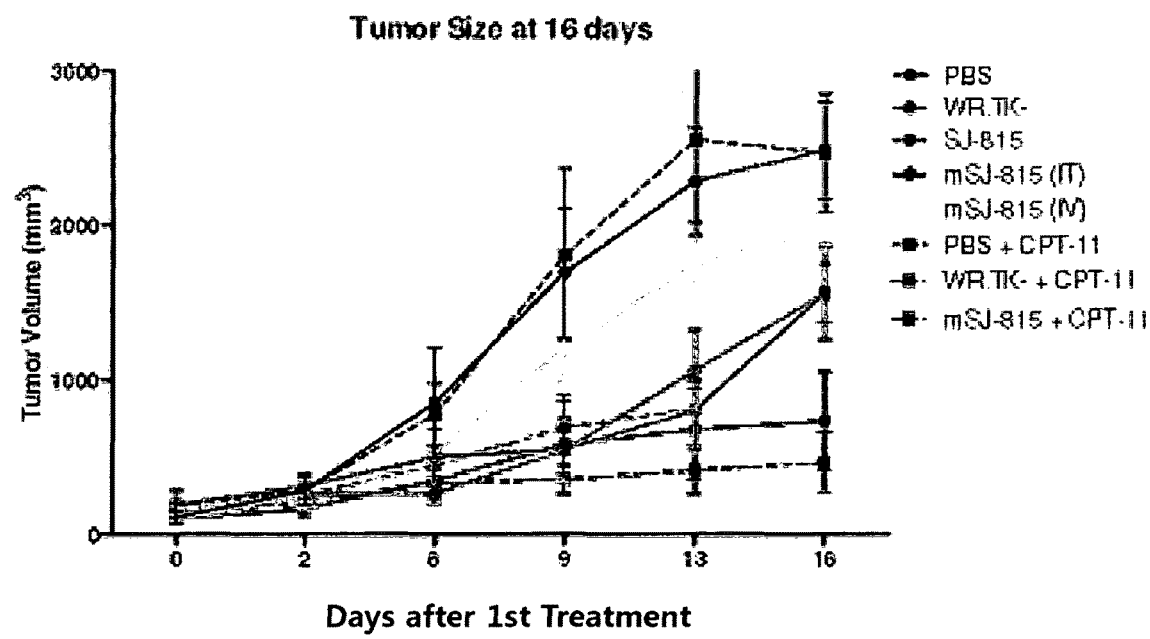
Days after 1st Treatment

[Fig. 16]
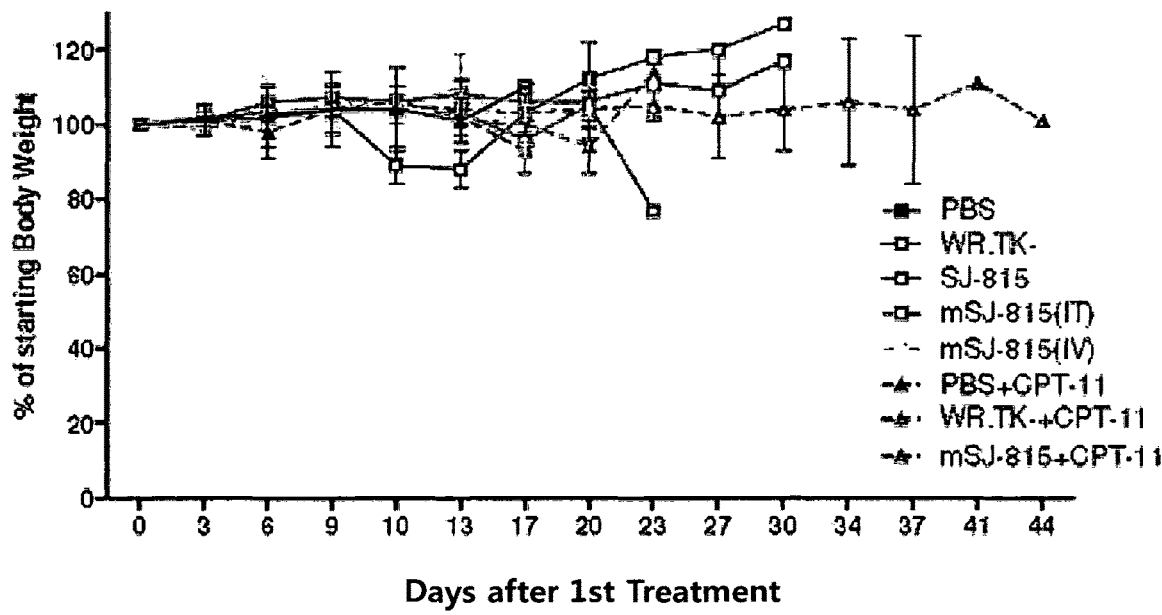
Days after 1st Treatment
[Fig. 17A]
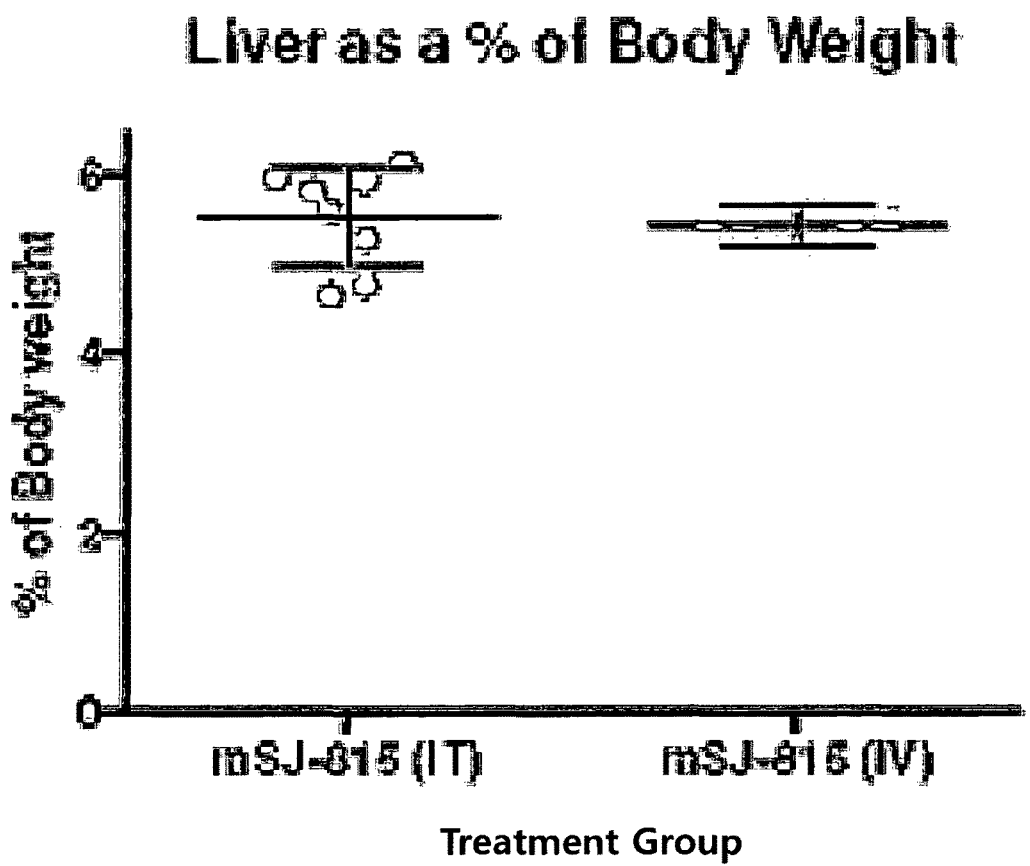

[Fig. 17B]
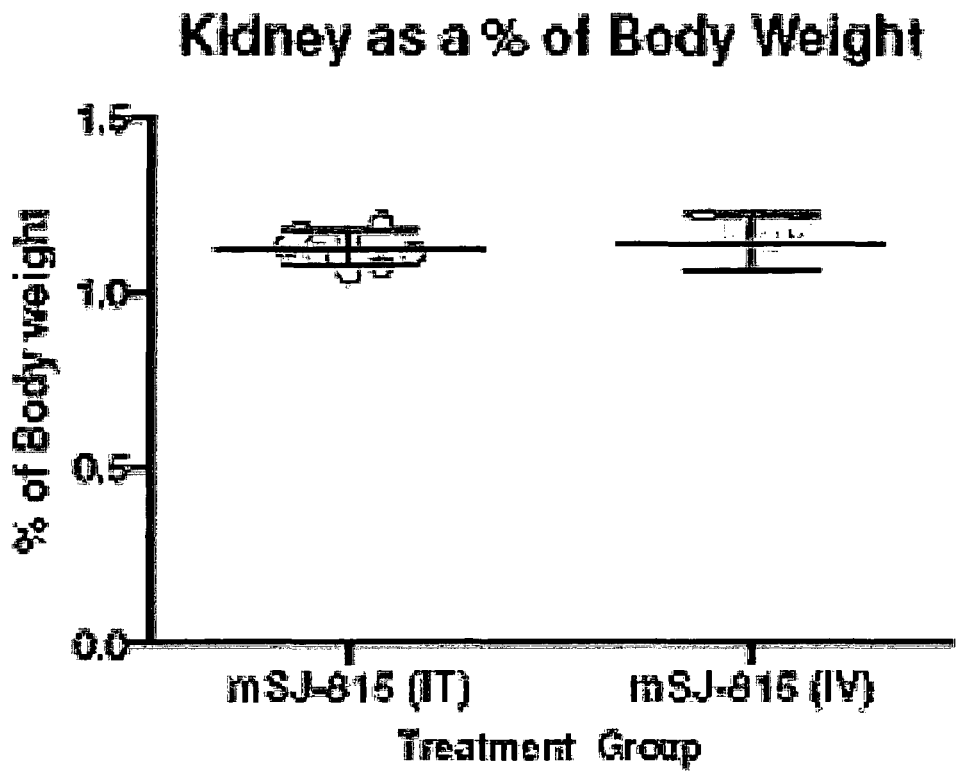
[Fig. 17C]
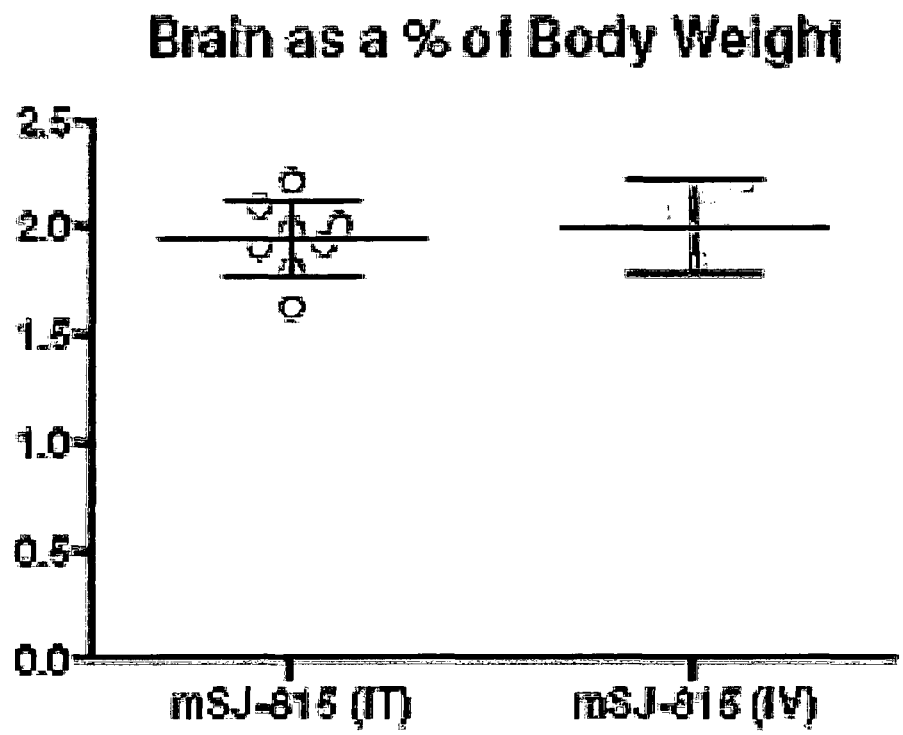

[Fig. 17D]
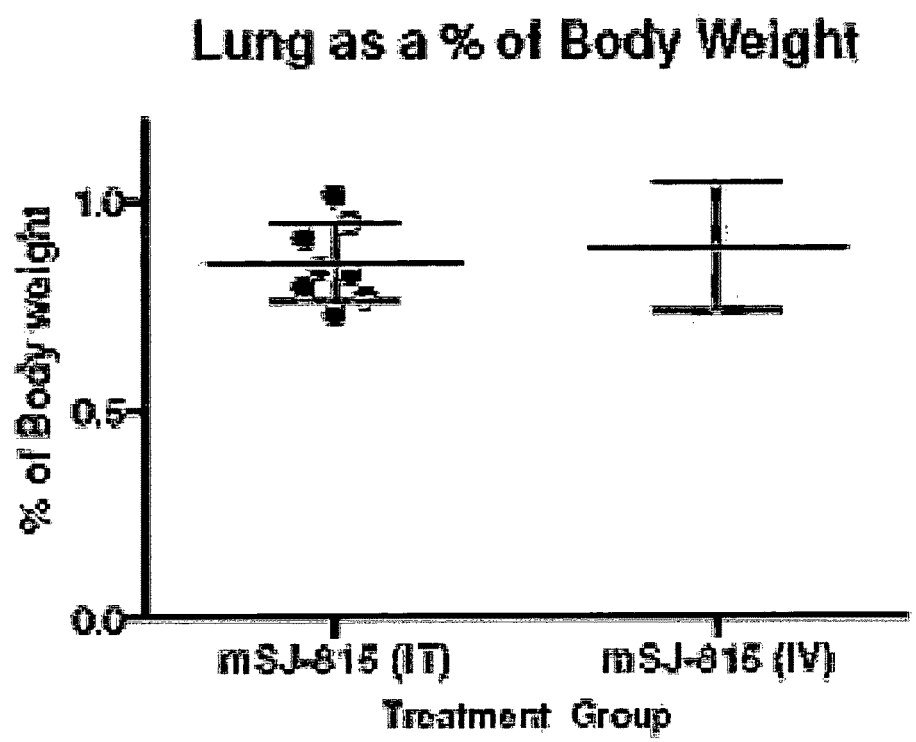
[Fig. 18A]
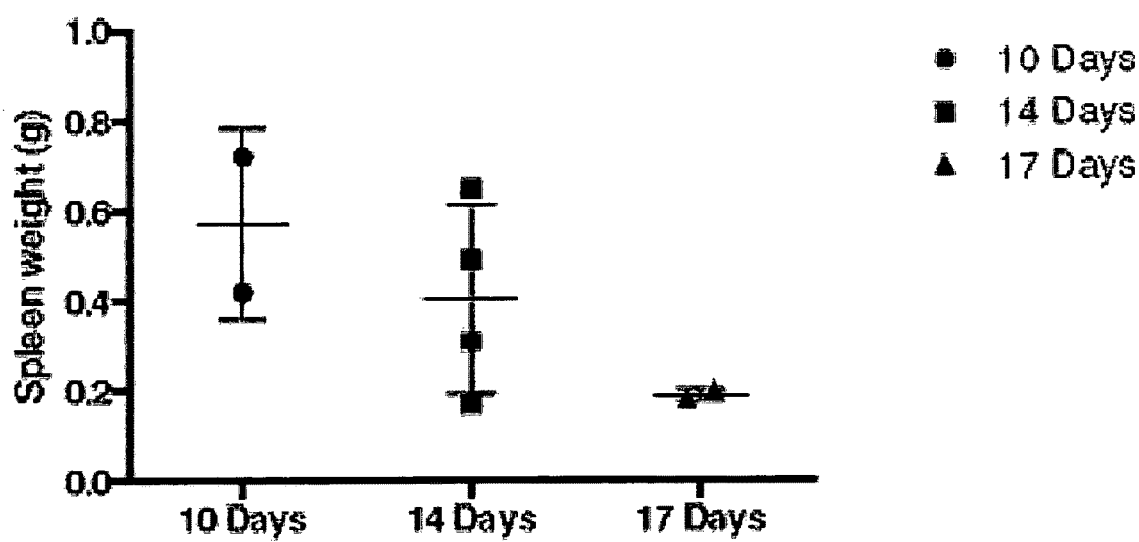

[Fig. 18B]
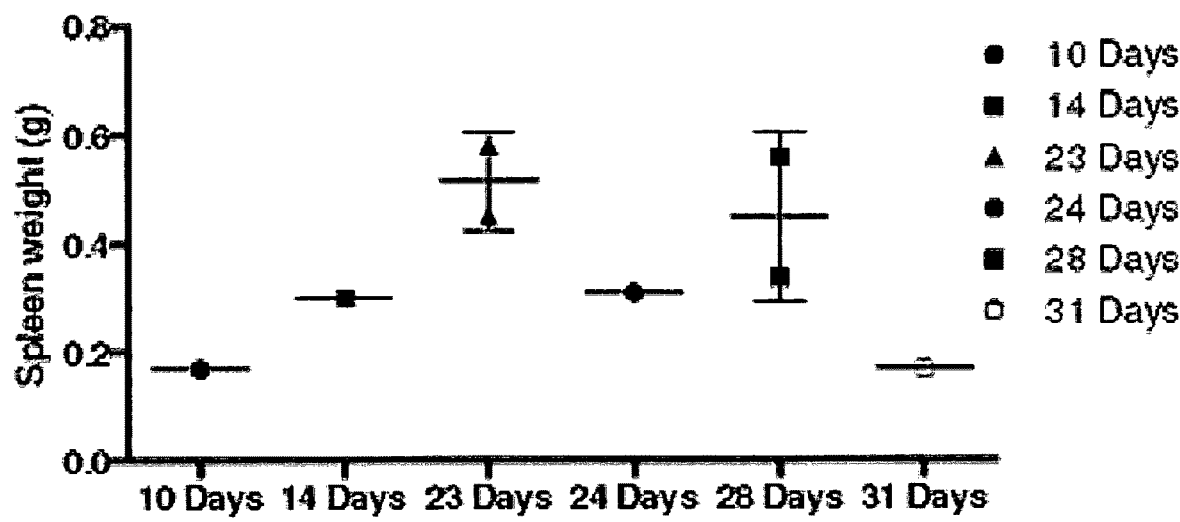
[Fig. 19]
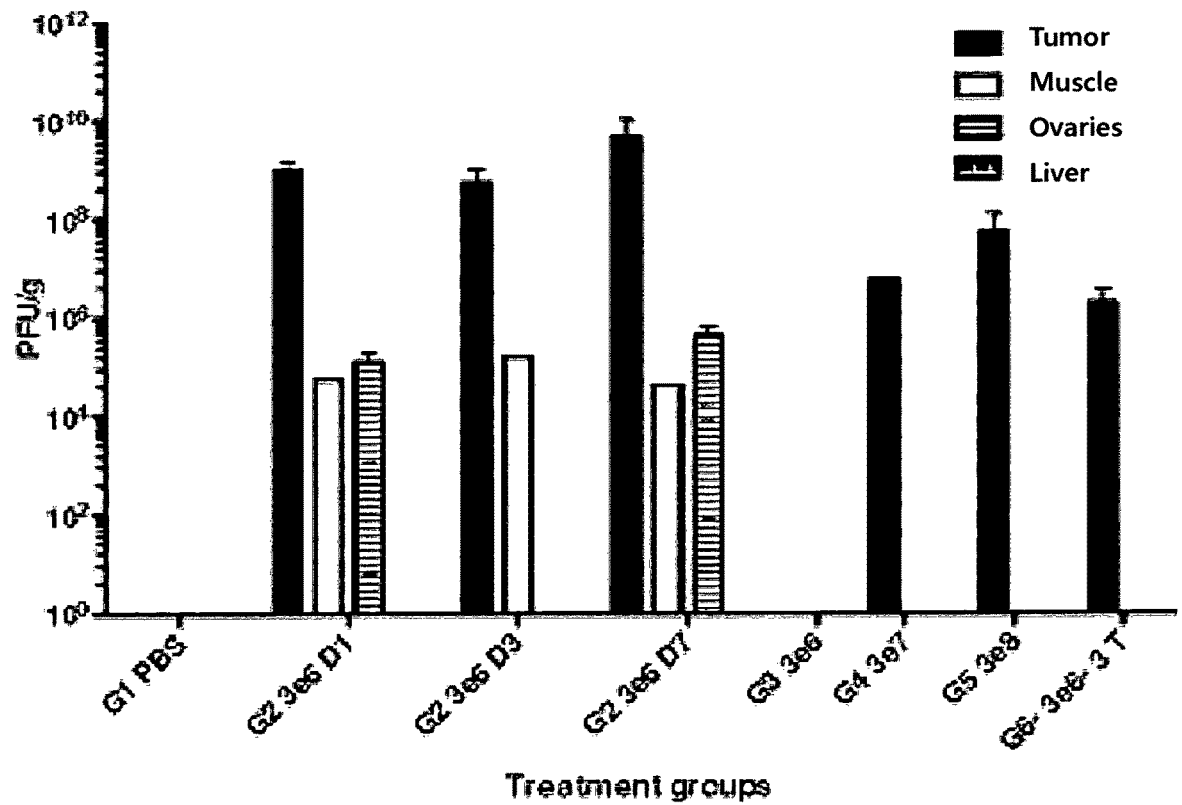

SEQUENCE LISTING

```
<160> NUMBER OF SEQ ID NOS: 3

<210> SEQ ID NO 1
<211> LENGTH: 4
<212> TYPE: PRT
<213> ORGANISM: Artificial Sequence
<220> FEATURE:
```

```
<223> OTHER INFORMATION: Synthetic Construct

<400> SEQUENCE: 1

His Thr Glu Leu
1

<210> SEQ ID NO 2
<211> LENGTH: 23
<212> TYPE: DNA
<213> ORGANISM: Artificial Sequence
<220> FEATURE:
<223> OTHER INFORMATION: Synthetic Construct

<400> SEQUENCE: 2
gcctagatct gtcgacttcg agc                                              23

<210> SEQ ID NO 3
<211> LENGTH: 24
<212> TYPE: DNA
<213> ORGANISM: Artificial Sequence
<220> FEATURE:
<223> OTHER INFORMATION: Synthetic Construct

<400> SEQUENCE: 3
aacgtatatg tgtaccggga gcag                                             24
```

MODIFIED ONCOLYTIC VACCINIA VIRUSES EXPRESSING A CYTOKINE AND A CAR-BOXYLESTERASE AND METHODS OF USE THEREOF

CROSS-REFERENCE TO RELATED APPLICATIONS

This application is a U.S. National Phase Patent Application of PCT/KR2016/009866, filed Sep. 2, 2016, which claims the benefit of U.S. Provisional Patent Application No. 62/215,651, filed Sep. 8, 2015, each of which are incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 737562000300SEQLIST.TXT, date recorded: Apr. 25, 2018, size: 1 KB).

TECHNICAL FIELD

The present disclosure relates generally to compositions and methods related to oncolytic vaccinia viruses that have been modified to express a cytokine and a carboxylesterase enzyme and that preferably do not express an active thymidine kinase, optionally in combinations with a cancer co-drug, preferably a topoisomerase inhibitor.

BACKGROUND ART

Normal tissue homeostasis is a highly regulated process of cell proliferation and cell death. An imbalance of either cell proliferation or cell death can develop into a cancerous state. For example, cervical, kidney, lung, pancreatic, colorectal, and brain cancer are just a few examples of the many cancers that can result. In fact, the occurrence of cancer is so high that over 500,000 deaths per year are attributed to cancer in the United States alone.

Currently, there are few effective options for the treatment of common cancer types. The course of treatment for a given individual depends on the diagnosis, the stage to which the disease has developed and factors such as age, sex, and general health of the patient. The most conventional options of cancer treatment are surgery, radiation therapy and chemotherapy. Chemotherapy is associated with substantial toxicity that can negatively impact quality of life. Surgery plays a central role in the diagnosis and treatment of cancer. Typically, a surgical approach is required for biopsy and to remove cancerous growths. However, if the cancer has metastasized and is widespread, surgery is unlikely to result in a cure and an alternate approach must be taken. New agents and therapies are needed to extend life and improve quality of life in patients with cancer.

Replication-selective oncolytic viruses hold promise for the treatment of cancer. These viruses can cause tumor cell death through direct replication-dependent oncolytic effects. In addition, viruses are able to enhance the cell-mediated antitumoral immunity within the host. These viruses also can be engineered to express therapeutic transgenes within the tumor to enhance antitumoral efficacy. However, major limitations exist to this therapeutic approach as well.

DISCLOSURE OF INVENTION

Technical Problem

Therefore, additional therapies for the treatment of cancer are needed. The use of oncolytic viruses expressing factors that enhance the immune response and increase chemotherapeutic efficacy presents a potential area for development.

Solution to Problem

Certain aspects of the compositions, combinations, and methods disclosed herein are based upon the targeted sequential multi-modal tumor killing effect of oncolytic vaccinia viruses disclosed herein that have been modified to express a cytokine and a carboxylesterase enzyme. In a preferred embodiment, the sequential multi-modal treatment results in an improvement over existing therapies and more effective tumor debulking. The selectivity of the oncolytic vaccinia virus means that expression of the cytokine and the carboxylesterase enzyme will be largely limited to the tumor environment. The oncolytic vaccinia virus and the cytokine, such as interferon-beta-1, will each act to debulk the tumor mass with the combination being even more effective than either the virus or the cytokine being administered on its own. After virus-mediated cell lysis, the carboxylesterase enzyme expressed from the virus genome will be released into the local tumor environment where it will ideally convert the cancer co-drugs to their active form largely within the local tumor environment, resulting in a high local concentration of the active drug form. This mechanism potentially allows for lower (and therefore safer) cancer co-drug doses needed to achieve effective treatment of the remaining cancer cells in the tumor that are not eliminated as a result of the combined debulking effects of the virus-mediated cell lysis and the cytokine. These effects all combined will result in a multi-modal killing of the tumor more thoroughly and effectively than any one of the three by themselves. Finally, each acts by a different mode thereby reducing the likelihood of selecting for cancerous cells that are resistant to further treatment.

An aspect of the invention includes compositions comprising a synthetic oncolytic vaccinia virus that expresses a cytokine and a carboxylesterase enzyme and that does not express an active thymidine kinase. In some embodiments, the carboxylesterase enzyme comprises a C-terminal retention sequence. In some embodiments, the C-terminal retention sequence is HTEL (SEQ ID NO: 1). In some embodiments, the carboxylesterase enzyme does not comprise a C-terminal retention sequence. In some embodiments, which can be combined with any of the preceding embodiments, the carboxylesterase enzyme is CES2, preferably human CES2 (hCES2). In some embodiments, which can be combined with any of the preceding embodiments, expression of the carboxylesterase enzyme is under control of a late-early VACV p7.5 promoter, a vaccinia modified H5 (mH5) promoter, a vaccinia short synthetic early-late pS promoter, a pC11R promoter, a pF11L promoter, a psFJ1-10 synthetic early promoter, a pHyb synthetic early promoter, any native vaccinia early promoters, and a Late-Early Optimized (LEO) promoter. In some embodiments, which can be combined with any of the preceding embodiments, the cytokine is selected from the group consisting of interferon-beta-1 (preferably human), IL-1α, IL-2, IL-3, IL-4, IL-5, IL-6, IL-7, IL-8, IL-9, IL-10, IL-12, IL-13, IL-14, IL-15, IL-17, IL-18, IL-21, IL-23, IL-24 CCL3, CCL5, and CXCR4. In some embodiments, which can be combined with any of the preceding embodiments, the cytokine is interferon-beta-1 (preferably human). In some embodiments, which can be combined with any of the preceding embodiments, expression of the cytokine is under control of a late-early VACV p7.5 promoter, a vaccinia modified H5 (mH5) promoter, a vaccinia short synthetic early-late pS promoter, a pC11R promoter, a pF11L promoter, a psFJ1-10 synthetic early promoter, a pHyb synthetic early promoter, any native vaccinia early promoters, and a Late-Early Optimized (LEO) promoter. In some embodiments, which can be combined with any of the preceding embodiments, the vaccinia virus is a Wyeth, Copenhagen, Western Reserve or Lister strain. In some embodiments, which can be combined with any of the preceding embodiments, the vaccinia virus expresses one or more of the following: a granulocyte-macrophage colony-stimulating factor (GM-CSF) (preferably human GM-CSF), a cytosine deaminase protein, and somatostatin receptor type 2 protein. In some embodiments, which can be combined with any of the preceding embodiments, the vaccinia virus does not express an active vaccinia growth factor (VGF) gene. In some embodiments, which can be combined with any of the preceding embodiments, the composition comprises between $1 \times 10^6$ and $1 \times 10^{12}$ plaque forming units (pfu), preferably between $1 \times 10^7$ and $1 \times 10^{10}$ pfu. In some embodiments, the vaccinia virus is the Western Reserve strain, the carboxylesterase is a human CES2 enzyme with a C-terminal retention sequence, and the cytokine is human interferon-beta-1. In some embodiments, the A34R gene comprises a K151E mutation. In some embodiments, which can be combined with any of the preceding embodiments, the composition further comprises a biocompatible microparticle or hydrophilic polymer gel agent suitable for active embolization. In some embodiments, which can be combined with any of the preceding embodiments, the biocompatible microparticle or hydrophilic polymer gel agent is selected from the list consisting of: degradable starch, polyvinyl alcohol, gelatin foam, and sulfonated polyvinyl alcohol hydrogel. In some embodiments, which can be combined with any of the preceding embodiments, the microparticles of the biocompatible microparticle agent are between 100 µm and 2000 µm, between 150 µm and 350 µm, between 150 µm and 200 µm, between 200 µm and 250 µm in size, between 250 µm and 300 µm, or between 300 µm and 350 µm in size. In some embodiments, which can be combined with any of the preceding embodiments, individual particles of the biocompatible microparticle agent vary in size from about 0 µm to about 100 µm, from about 0 µm to about 50 µm, or from about 0 µm to about 25 µm. In some embodiments, which can be combined with any of the preceding embodiments, individual particles of the biocompatible microparticle agent have an average difference in diameter of 100 µm or less, about 50 µm or less, about 25 µm or less, about 10 µm or less or about 5 µm or less. In some embodiments, which can be combined with any of the preceding embodiments individual particles of the biocompatible microparticle agent are aggregates of particulates that are between 10 and 200 µm or between 10 and 100 µm. In some embodiments, which can be combined with any of the preceding embodiments, the hydrophilic polymer gel agent comprises particulates that are between 10 and 200 µm or between 10 and 100 µm. In some embodiments, which can be combined with any of the preceding embodiments, the biocompatible microparticle or hydrophilic polymer gel agent is a temporary embolic agent or a permanent embolic agent.

Another aspect of the invention includes methods for treating cancer in a mammal, comprising administering to the mammal an effective amount of a composition comprising a synthetic oncolytic vaccinia virus that expresses a cytokine and a carboxylesterase enzyme and that does not express an active thymidine kinase. In some embodiments, the carboxylesterase enzyme comprises a C-terminal retention sequence. In some embodiments, the C-terminal retention sequence is HTEL (SEQ ID NO: 1). In some embodiments, the carboxylesterase enzyme does not comprise a C-terminal retention sequence. In some embodiments, which can be combined with any of the preceding embodiments, the carboxylesterase enzyme is CES2, preferably human CES2 (hCES2). In some embodiments, which can be combined with any of the preceding embodiments, expression of the carboxylesterase enzyme is under control of a late-early VACV p7.5 promoter, a vaccinia modified H5 (mH5) promoter, a vaccinia short synthetic early-late pS promoter, a pC11R promoter, a pF11L promoter, a psFJ1-10 synthetic early promoter, a pHyb synthetic early promoter, any native vaccinia early promoters, and a Late-Early Optimized (LEO) promoter. In some embodiments, which can be combined with any of the preceding embodiments, the cytokine is selected from the group consisting of interferon-beta-1 (preferably human), IL-1α, IL-2, IL-3, IL-4, IL-5, IL-6, IL-7, IL-8, IL-9, IL-10, IL-12, IL-13, IL-14, IL-15, IL-17, IL-18, IL-21, IL-23, IL-24 CCL3, CCL5, and CXCR4. In some embodiments, which can be combined with any of the preceding embodiments, the cytokine is interferon-beta-1 (preferably human). In some embodiments, which can be combined with any of the preceding embodiments, expression of the cytokine is under control of a a late-early VACV p7.5 promoter, a vaccinia modified H5 (mH5) promoter, a vaccinia short synthetic early-late pS promoter, a pC11R promoter, a pF11L promoter, a psFJ1-10 synthetic early promoter, a pHyb synthetic early promoter, any native vaccinia early promoters, and a Late-Early Optimized (LEO) promoter. In some embodiments, which can be combined with any of the preceding embodiments, the vaccinia virus is a Wyeth, Copenhagen, Western. Reserve or Lister strain. In some embodiments, which can be combined with any of the preceding embodiments, the vaccinia virus expresses one or more of the following: a granulocyte-macrophage colony-stimulating factor (GM-CSF) (preferably human GM-CSF), a cytosine deaminase protein, and somatostatin receptor type 2 protein. In some embodiments, which can be combined with any of the preceding embodiments, the vaccinia virus does not express an active vaccinia growth factor (VGF) gene. In some embodiments, the vaccinia virus is the Western Reserve strain, the carboxylesterase is a human CES2 enzyme with a C-terminal retention sequence, and the cytokine is human interferon-beta-1. In some embodiments, the A34R gene comprises a K151E mutation. In some embodiments, which can be combined with any of the preceding embodiments, the composition comprises between $1 \times 10^6$ and $1 \times 10^{12}$ plaque forming units (pfu), preferably between $1 \times 10^7$ and $1 \times 10^{10}$ pfu. In some embodiments, which can be combined with any of the preceding embodiments, the method further comprises a biocompatible microparticle or hydrophilic polymer gel agent suitable for active embolization. In some embodiments, which can be combined with any of the preceding embodiments, the biocompatible microparticle or hydrophilic polymer gel agent is selected from the list consisting of: degradable starch, polyvinyl alcohol, gelatin foam, and sulfonated polyvinyl alcohol hydrogel. In some embodiments, which can be combined with any of the preceding embodiments, the microparticles of the biocompatible microparticle agent are between 100 µm and 2000 µm, between 150 µm and 350 µm, between 150 µm and 200 µm, between 200 µm and 250 µm in size, between 250 µm and 300 µm, or between 300 µm and 350 µm in size. In some embodiments, which can be combined with any of the preceding embodiments, individual particles of the biocompatible microparticle agent vary in size from about 0 µm to about 100 µm, from about 0 µm to about 50 µm, or from about 0 µm to about 25 µm. In some embodiments, which can be combined with any of the preceding embodiments, individual particles of the biocompatible microparticle agent have an average difference in diameter of 100 µm or less, about 50 µm or less, about 25 µm or less, about 10 µm or less or about 5 µm or less. In some embodiments, which can be combined with any of the preceding embodiments, individual particles of the biocompatible microparticle agent are aggregates of particulates that are between 10 and 200 µm or between 10 and 100 µm. In some embodiments, which can be combined with any of the preceding embodiments, the hydrophilic polymer gel agent comprises particulates that are between 10 and 200 µm or between 10 and 100 µm. In some embodiments, which can be combined with any of the preceding embodiments, the biocompatible microparticle or hydrophilic polymer gel agent is a temporary embolic agent or a permanent embolic agent. In some embodiments, which can be combined with any of the preceding embodiments, the cancer is colorectal cancer, lung cancer, melanoma, pancreatic cancer, ovarian cancer, cervical cancer or liver cancer. In some embodiments, which can be combined with any of the preceding embodiments, the mammal is a human. In some embodiments, which can be combined with any of the preceding embodiments, the cancer is refractory to treatment with one or more chemotherapeutic agents and/or is refractory to treatment with one or more antibodies. In some embodiments, which can be combined with any of the preceding embodiments, the cancer is refractory to treatment with a topoisomerase inhibitor, preferably irinotecan. In some embodiments, which can be combined with any of the preceding embodiments, the cancer is melanoma. In some embodiments, which can be combined with any of the preceding embodiments, the cancer is refractory to treatment comprising fluoropyrimidine and oxaliplatin and/or is refractory to treatment comprising cetuximab and/or panitumumab. In some embodiments, which can be combined with any of the preceding embodiments, the oncolytic vaccinia virus is administered intratumorally or intravenously at one or more doses of between $1\times10^6$ and $1\times10^{12}$ plaque forming units (pfu), preferably between $1\times10^7$ and $1\times10^{10}$ pfu. In some embodiments, which can be combined with any of the preceding embodiments, the method further comprises administering to the mammal one or more additional anti-cancer agents, preferably selected from 5-fluorouracil (FU), folinic acid (FA), methotrexate, capecitabine, oxaliplatin, bevacizumab, cetuximab and any combination thereof.

Another aspect of the invention includes methods for treating cancer in a mammal, comprising administering to the mammal an effective amount of a combination comprising (a) a composition comprising a synthetic oncolytic vaccinia virus that expresses a cytokine and a carboxylesterase enzyme and that does not express an active thymidine kinase and (b) a cancer co-drug. In some embodiments, the cancer co-drug is a topoisomerase inhibitor. In some embodiments, the cancer co-drug is an activatable cancer co-drug. In some embodiments, the activatable cancer co-drug is selected from a topoisomerase inhibitor, paclitaxel-2-ethylcarbonate (which is converted to paclitaxel), capecitabine (which is converted to 5'-Deoxy-5-fluorocytidine (5-FU)), and any tertiary amidomethyl ester prodrugs of existing chemotherapeutics. In some embodiments, the carboxylesterase enzyme comprises a C-terminal retention sequence. In some embodiments, the C-terminal retention sequence is HTEL (SEQ ID NO: 1). In some embodiments, the carboxylesterase enzyme does not comprise a C-terminal retention sequence. In some embodiments, which can be combined with any of the preceding embodiments, the carboxylesterase enzyme is CES2, preferably human CES2 (hCES2). In some embodiments, which can be combined with any of the preceding embodiments, expression of the carboxylesterase enzyme is under control of a late-early VACV p'7.5 promoter, a vaccinia modified H5 (mH5) promoter, a vaccinia short synthetic early-late pS promoter, a pC11R promoter, a pF11L promoter, a psFJ1-10 synthetic early promoter, a pHyb synthetic early promoter, any native vaccinia early promoters, and a Late-Early Optimized (LEO) promoter. In some embodiments, which can be combined with any of the preceding embodiments, the cytokine is selected from the group consisting of interferon-beta-1 (preferably human), IL-1?, IL-2, IL-3, IL-4, IL-5, IL-6, IL-7, IL-8, IL-9, IL-10, IL-12, IL-13, IL-14, IL-15, IL-17, IL-18, IL-21, IL-23, IL-24 CCL3, CCL5, and CXCR4. In some embodiments, which can be combined with any of the preceding embodiments, the cytokine is interferon-beta-1 (preferably human). In some embodiments, which can be combined with any of the preceding embodiments, expression of the cytokine is under control of a a late-early VACV p7.5 promoter, a vaccinia modified H5 (mH5) promoter, a vaccinia short synthetic early-late pS promoter, a pC11R promoter, a pF11L promoter, a psFJ1-10 synthetic early promoter, a pHyb synthetic early promoter, any native vaccinia early promoters, and a Late-Early Optimized (LEO) promoter. In some embodiments, which can be combined with any of the preceding embodiments, the vaccinia virus is a Wyeth, Copenhagen, Western Reserve or Lister strain. In some embodiments, which can be combined with any of the preceding embodiments, the vaccinia virus expresses one or more of the following: a granulocyte-macrophage colony-stimulating factor (GM-CSF) (preferably human GM-CSF), a cytosine deaminase protein, and somatostatin receptor type 2 protein. In some embodiments, which can be combined with any of the preceding embodiments, the vaccinia virus does not express an active vaccinia growth factor (VGF) gene. In some embodiments, the vaccinia virus is the Western Reserve strain, the carboxylesterase is a human CES2 enzyme with a C-terminal retention sequence, and the cytokine is human interferon-beta-1. In some embodiments, the A34R gene comprises a K151E mutation. In some embodiments, which can be combined with any of the preceding embodiments, the composition comprises between $1\times10^6$ and $1\times10^{12}$ plaque forming units (pfu), preferably between $1\times10^7$ and $1\times10^{10}$ pfu. In some embodiments, which can be combined with any of the preceding embodiments, the method further comprises a biocompatible microparticle or hydrophilic polymer gel agent suitable for active embolization. In some embodiments, which can be combined with any of the preceding embodiments, the biocompatible microparticle or hydrophilic polymer gel agent is selected from the list consisting of: degradable starch, polyvinyl alcohol, gelatin foam, and sulfonated polyvinyl alcohol hydrogel. In some embodiments, which can be combined with any of the preceding embodiments, the microparticles of the biocompatible microparticle agent are between 100 µm and 2000 µm, between 150 µm and 350 µm, between 150 µm and 200 µm, between 200 µm and 250 µm in size, between 250 µm and 300 µm, or between 300 µm and 350 µm in size. In some embodiments, which can be combined with any of the preceding embodiments, individual particles of the biocompatible microparticle agent vary in size from about 0 µm to about 100 µm, from about 0 µm to about 50 µm, or from about 0 µm to about 25 µm. In some embodiments, which can be combined with any of the preceding embodiments, individual particles of the biocompatible microparticle agent have an average difference in diameter of 100 µm or less, about 50 µm or less, about 25 µm or less, about 10 µm or less or about 5 µm or less. In some embodiments, which can be combined with any of the preceding embodiments, individual particles of the biocompatible microparticle agent are aggregates of particulates that are between 10 and 200 µm or between 10 and 100 µm. In some embodiments, which can be combined with any of the preceding embodiments, the hydrophilic polymer gel agent comprises particulates that are between 10 and 200 µm or between 10 and 100 µm. In some embodiments, which can be combined with any of the preceding embodiments, the biocompatible microparticle or hydrophilic polymer gel agent is a temporary embolic agent or a permanent embolic agent. In some embodiments, which can be combined with any of the preceding embodiments, the cancer is colorectal cancer, lung cancer, melanoma, pancreatic cancer, ovarian cancer, cervical cancer or liver cancer. In some embodiments, which can be combined with any of the preceding embodiments, the mammal is a human. In some embodiments, which can be combined with any of the preceding embodiments, the cancer is refractory to treatment with one or more chemotherapeutic agents and/or is refractory to treatment with one or more antibodies. In some embodiments, which can be combined with any of the preceding embodiments, the cancer is refractory to treatment with a topoisomerase inhibitor, preferably irinotecan. In some embodiments, which can be combined with any of the preceding embodiments, the cancer is melanoma. In some embodiments, which can be combined with any of the preceding embodiments, the cancer is refractory to treatment comprising fluoropyrimidine and oxaliplatin and/or is refractory to treatment comprising cetuximab and/or panitumumab. In some embodiments, which can be combined with any of the preceding embodiments, the oncolytic vaccinia virus is administered intratumorally or intravenously at one or more doses of between $1\times10^6$ and $1\times10^{12}$ plaque forming units (pfu), preferably between $1\times10^7$ and $1\times10^{10}$ pfu. In some embodiments, which can be combined with any of the preceding embodiments, the method further comprises administering to the mammal one or more additional anti-cancer agents, preferably selected from 5-fluorouracil (FU), folinic acid (FA), methotrexate, capecitabine, oxaliplatin, bevacizumab, cetuximab and any combination thereof. In some embodiments, which can be combined with any of the preceding embodiments, (a) and (b) are administered in synergistically effective amounts. In some embodiments, which can be combined with any of the preceding embodiments, the co-drug is a camptothecin analogue, preferably selected from topotecan and irinotecan, more preferably irinotecan. In some embodiments, which can be combined with any of the preceding embodiments, (a) and (b) are sequentially, simultaneously or separately administered. In some embodiments, which can be combined with any of the preceding embodiments, (a) and (b) are co-administered to the mammal in the same formulation. In some embodiments, which can be combined with any of the preceding embodiments, (a) and (b) are co-administered to the mammal in different formulations. In some embodiments, which can be combined with any of the preceding embodiments, (a) and (b) are administered to the mammal by the same route, preferably wherein (a) and (b) are both administered by intravenous administration. In some embodiments, which can be combined with any of the preceding embodiments, a first dose of oncolytic vaccinia virus is administered prior to a first dose of cancer co-drug. In some embodiments, which can be combined with any of the preceding embodiments, the cancer co-drug is administered every other week at a dosage of from 120 to 250 mg/m$^2$, preferably wherein the cancer co-drug is irinotecan and is administered every other week at a dosage of about 180 mg/m$^2$. In some embodiments, which can be combined with any of the preceding embodiments, the oncolytic vaccinia virus is administered weekly or every other week and wherein the cancer co-drug is administered every other week, preferably wherein administration of the cancer co-drug is initiated one to three days after the second weekly dose of the oncolytic vaccinia virus.

Another aspect of the invention includes methods for treating cancer in a mammal, comprising introducing into the vasculature of a mammal a composition comprising a synthetic oncolytic vaccinia virus that expresses a cytokine and a carboxylesterase enzyme and that does not express an active thymidine kinase and a biocompatible microparticle or hydrophilic polymer gel agent suitable for active embolization. In some embodiments, the carboxylesterase enzyme comprises a C-terminal retention sequence. In some embodiments, the C-terminal retention sequence is HTEL (SEQ ID NO: 1). In some embodiments, the carboxylesterase enzyme does not comprise a C-terminal retention sequence. In some embodiments, which can be combined with any of the preceding embodiments, the carboxylesterase enzyme is CES2, preferably human CES2 (hCES2). In some embodiments, which can be combined with any of the preceding embodiments, expression of the carboxylesterase enzyme is under control of a late-early VACV p7.5 promoter, a vaccinia modified H5 (mH5) promoter, a vaccinia short synthetic early-late pS promoter, a pC11R promoter, a pF11L promoter, a psFJ1-10 synthetic early promoter, a pHyb synthetic early promoter, any native vaccinia early promoters, and a Late-Early Optimized (LEO) promoter. In some embodiments, which can be combined with any of the preceding embodiments, the cytokine is selected from the group consisting of interferon-beta-1 (preferably human), IL-1α, IL-2, IL-3, IL-4, IL-5, IL-6, IL-7, IL-8, IL-9, IL-10, IL-12, IL-13, IL-14, IL-15, IL-17, IL-18, IL-21, IL-23, IL-24 CCL3, CCL5, and CXCR4. In some embodiments, which can be combined with any of the preceding embodiments, the cytokine is interferon-beta-1 (preferably human). In some embodiments, which can be combined with any of the preceding embodiments, expression of the cytokine is under control of a a late-early VACV p7.5 promoter, a vaccinia modified H5 (mH5) promoter, a vaccinia short synthetic early-late pS promoter, a pC11R promoter, a pF11L promoter, a psFJ1-10 synthetic early promoter, a pHyb synthetic early promoter, any native vaccinia early promoters, and a Late-Early Optimized (LEO) promoter. In some embodiments, which can be combined with any of the preceding embodiments, the vaccinia virus is a Wyeth, Copenhagen, Western Reserve or Lister strain. In some embodiments, which can be combined with any of the preceding embodiments, the vaccinia virus expresses one or more of the following: a granulocyte-macrophage colony-stimulating factor (GM-CSF) (preferably human GM-CSF), a cytosine deaminase protein, and somatostatin receptor type 2 protein. In some embodiments, which can be combined with any of the preceding embodiments, the vaccinia virus does not express an active vaccinia growth factor (VGF) gene. In some embodiments, the vaccinia virus is the Western Reserve strain, the carboxylesterase is a human CES2 enzyme with a C-terminal retention sequence, and the cytokine is human interferon-beta-1. In some embodiments, the A34R gene comprises a K151E mutation. In some embodiments, which can be combined with any of the preceding embodiments, the composition comprises between $1\times10^6$ and $1\times10^{12}$ plaque forming units (pfu), preferably between $1\times10^7$ and $1\times10^{10}$ pfu. In some embodiments, which can be combined with any of the preceding embodiments, the method further comprises a biocompatible microparticle or hydrophilic polymer gel agent suitable for active embolization. In some embodiments, which can be combined with any of the preceding embodiments, the biocompatible microparticle or hydrophilic polymer gel agent is selected from the list consisting of: degradable starch, polyvinyl alcohol, gelatin foam, and sulfonated polyvinyl alcohol hydrogel. In some embodiments, which can be combined with any of the preceding embodiments, the microparticles of the biocompatible microparticle agent are between 100 μm and 2000 μm, between 150 μm and 350 μm, between 150 μm and 200 μm, between 200 μm and 250 μm in size, between 250 μm and 300 μm, or between 300 μm and 350 μm in size. In some embodiments, which can be combined with any of the preceding embodiments, individual particles of the biocompatible microparticle agent vary in size from about 0 μm to about 100 μm, from about 0 μm to about 50 μm, or from about 0 μm to about 25 μm. In some embodiments, which can be combined with any of the preceding embodiments, individual particles of the biocompatible microparticle agent have an average difference in diameter of 100 μm or less, about 50 μm or less, about 25 μm or less, about 10 μm or less or about 5 μm or less. In some embodiments, which can be combined with any of the preceding embodiments, individual particles of the biocompatible microparticle agent are aggregates of particulates that are between 10 and 200 μm or between 10 and 100 μm. In some embodiments, which can be combined with any of the preceding embodiments, the hydrophilic polymer gel agent comprises particulates that are between 10 and 200 μm or between 10 and 100 μm. In some embodiments, which can be combined with any of the preceding embodiments, the biocompatible microparticle or hydrophilic polymer gel agent is a temporary embolic agent or a permanent embolic agent. In some embodiments, which can be combined with any of the preceding embodiments, the cancer is colorectal cancer, lung cancer, melanoma, pancreatic cancer, ovarian cancer, cervical cancer or liver cancer. In some embodiments, which can be combined with any of the preceding embodiments, the mammal is a human. In some embodiments, which can be combined with any of the preceding embodiments, the cancer is refractory to treatment with one or more chemotherapeutic agents and/or is refractory to treatment with one or more antibodies. In some embodiments, which can be combined with any of the preceding embodiments, the cancer is refractory to treatment with a topoisomerase inhibitor, preferably irinotecan. In some embodiments, the cancer is melanoma. In some embodiments, which can be combined with any of the preceding embodiments, the cancer is refractory to treatment comprising fluoropyrimidine and oxaliplatin and/or is refractory to treatment comprising cetuximab and/or panitumumab. In some embodiments, which can be combined with any of the preceding embodiments, the oncolytic vaccinia virus is administered intratumorally or intravenously at one or more doses of between $1\times10^6$ and $1\times10^{12}$ plaque forming units (pfu), preferably between $1\times10^7$ and $1\times10^{10}$ pfu. In some embodiments, which can be combined with any of the preceding embodiments, the method further comprises administering to the mammal one or more additional anti-cancer agents, preferably selected from 5-fluorouracil (FU), folinic acid (FA), methotrexate, capecitabine, oxaliplatin, bevacizumab, cetuximab and any combination thereof.

Another aspect of the invention includes methods for treating cancer in a mammal, comprising (a) introducing into the vasculature of a mammal a composition comprising a synthetic oncolytic vaccinia virus that expresses a cytokine and a carboxylesterase enzyme and that does not express an active thymidine kinase and a biocompatible microparticle or hydrophilic polymer gel agent suitable for active embolization and (b) administering to the mammal a composition comprising an effective amount of a cancer co-drug. In some embodiments, the cancer co-drug is a topoisomerase inhibitor. In some embodiments, the cancer co-drug is an activatable cancer co-drug. In some embodiments, the cancer co-drug is any cancer drug activatable by a carboxylesterase, including, without limitation, a topoisomerase inhibitor, paclitaxel-2-ethylcarbonate (which is converted to paclitaxel), capecitabine (which is converted to 5'-Deoxy-5-fluorocytidine (5-FU)), and any tertiary amidomethyl ester prodrugs of existing chemotherapeutics. In some embodiments, the carboxylesterase enzyme comprises a C-terminal retention sequence. In some embodiments, the C-terminal retention sequence is HTEL (SEQ ID NO: 1). In some embodiments, the carboxylesterase enzyme does not comprise a C-terminal retention sequence. In some embodiments, which can be combined with any of the preceding embodiments, the carboxylesterase enzyme is CES2, preferably human CES2 (hCES2). In some embodiments, which can be combined with any of the preceding embodiments, expression of the carboxylesterase enzyme is under control of a late-early VACV p7.5 promoter, a vaccinia modified H5 (mH5) promoter, a vaccinia short synthetic early-late pS promoter, a pC11R promoter, a pF11L promoter, a psFJ1-10 synthetic early promoter, a pHyb synthetic early promoter, any native vaccinia early promoters, and a Late-Early Optimized (LEO) promoter. In some embodiments, which can be combined with any of the preceding embodiments, the cytokine is selected from the group consisting of interferon-beta-1 (preferably human), IL-1α, IL-2, IL-3, IL-4, IL-5, IL-6, IL-7, IL-8, IL-9, IL-10, IL-12, IL-13, IL-14, IL-15, IL-17, IL-18, IL-21, IL-23, IL-24 CCL3, CCL5, and CXCR4. In some embodiments, which can be combined with any of the preceding embodiments, the cytokine is interferon-beta-1 (preferably human). In some embodiments, which can be combined with any of the preceding embodiments, expression of the cytokine is under control of a a late-early VACV p7.5 promoter, a vaccinia modified H5 (mH5) promoter, a vaccinia short synthetic early-late pS promoter, a pC11R promoter, a pF11L promoter, a psFJ1-10 synthetic early promoter, a pHyb synthetic early promoter, any native vaccinia early promoters, and a Late-Early Optimized (LEO) promoter. In some embodiments, which can be combined with any of the preceding embodiments, the vaccinia virus is a Wyeth, Copenhagen, Western Reserve or Lister strain. In some embodiments, which can be combined with any of the preceding embodiments, the vaccinia virus expresses one or more of the following: a granulocyte-macrophage colony-stimulating factor (GM-CSF) (preferably human GM-CSF), a cytosine deaminase protein, and somatostatin receptor type 2 protein. In some embodiments, which can be combined with any of the preceding embodiments, the vaccinia virus does not express an active vaccinia growth factor (VGF) gene. In some embodiments, the vaccinia virus is the Western Reserve strain, the carboxylesterase is a human CES2 enzyme with a C-terminal retention sequence, and the cytokine is human interferon-beta-1. In some embodiments, the A34R gene comprises a K151E mutation. In some embodiments, which can be combined with any of the preceding embodiments, the composition comprises between $1\times10^6$ and $1\times10^{12}$ plaque forming units (pfu), preferably between $1\times10^7$ and $1\times10^{10}$ pfu. In some embodiments, which can be combined with any of the preceding embodiments, the method further comprises a biocompatible microparticle or hydrophilic polymer gel agent suitable for active embolization. In some embodiments, which can be combined with any of the preceding embodiments, the biocompatible microparticle or hydrophilic polymer gel agent is selected from the list consisting of: degradable starch, polyvinyl alcohol, gelatin foam, and sulfonated polyvinyl alcohol hydrogel. In some embodiments, which can be combined with any of the preceding embodiments, the microparticles of the biocompatible microparticle agent are between 100 μm and 2000 μm, between 150 μm and 350 μm, between 150 μm and 200 μm, between 200 μm and 250 μm in size, between 250 μm and 300 μm, or between 300 μm and 350 μm in size. In some embodiments, which can be combined with any of the preceding embodiments, individual particles of the biocompatible microparticle agent vary in size from about 0 μm to about 100 μm, from about 0 μm to about 50 μm, or from about 0 μm to about 25 μm. In some embodiments, which can be combined with any of the preceding embodiments, individual particles of the biocompatible microparticle agent have an average difference in diameter of 100 μm or less, about 50 μm or less, about 25 μm or less, about 10 μm or less or about 5 μm or less. In some embodiments, which can be combined with any of the preceding embodiments, individual particles of the biocompatible microparticle agent are aggregates of particulates that are between 10 and 200 μm or between 10 and 100 μm. In some embodiments, which can be combined with any of the preceding embodiments, the hydrophilic polymer gel agent comprises particulates that are between 10 and 200 μm or between 10 and 100 μm. In some embodiments, which can be combined with any of the preceding embodiments, the biocompatible microparticle or hydrophilic polymer gel agent is a temporary embolic agent or a permanent embolic agent. In some embodiments, which can be combined with any of the preceding embodiments, the cancer is colorectal cancer, lung cancer, melanoma, pancreatic cancer, ovarian cancer, cervical cancer or liver cancer. In some embodiments, which can be combined with any of the preceding embodiments, the mammal is a human. In some embodiments, which can be combined with any of the preceding embodiments, the cancer is refractory to treatment with one or more chemotherapeutic agents and/or is refractory to treatment with one or more antibodies. In some embodiments, which can be combined with any of the preceding embodiments, the cancer is refractory to treatment with a topoisomerase inhibitor, preferably irinotecan. In some embodiments, the cancer is melanoma. In some embodiments, which can be combined with any of the preceding embodiments, the cancer is refractory to treatment comprising fluoropyrimidine and oxaliplatin and/or is refractory to treatment comprising cetuximab and/or panitumumab. In some embodiments, which can be combined with any of the preceding embodiments, the oncolytic vaccinia virus is administered intratumorally or intravenously at one or more doses of between $1\times10^6$ and $1\times10^{12}$ plaque forming units (pfu), preferably between $1\times10^7$ and $1\times10^{10}$ pfu. In some embodiments, which can be combined with any of the preceding embodiments, the method further comprises administering to the mammal one or more additional anti-cancer agents, preferably selected from 5-fluorouracil (FU), folinic acid (FA), methotrexate, capecitabine, oxaliplatin, bevacizumab, cetuximab and any combination thereof. In some embodiments, which can be combined with any of the preceding embodiments, (a) and (b) are administered in synergistically effective amounts. In some embodiments, which can be combined with any of the preceding embodiments, the co-drug is a camptothecin analogue, preferably selected from topotecan and irinotecan, more preferably irinotecan. In some embodiments, which can be combined with any of the preceding embodiments, (a) and (b) are sequentially, simultaneously or separately administered. In some embodiments, which can be combined with any of the preceding embodiments, (a) and (b) are co-administered to the mammal in the same formulation. In some embodiments, which can be combined with any of the preceding embodiments, (a) and (b) are co-administered to the mammal in different formulations. In some embodiments, which can be combined with any of the preceding embodiments, (a) and (b) are administered to the mammal by the same route, preferably wherein (a) and (b) are both administered by intravenous administration. In some embodiments, which can be combined with any of the preceding embodiments, a first dose of oncolytic vaccinia virus is administered prior to a first dose of cancer co-drug. In some embodiments, which can be combined with any of the preceding embodiments, the cancer co-drug is administered every other week at a dosage of from 120 to 250 mg/m$^2$, preferably wherein the cancer co-drug is irinotecan and is administered every other week at a dosage of about 180 mg/m$^2$. In some embodiments, which can be combined with any of the preceding embodiments, the oncolytic vaccinia virus is administered weekly or every other week and wherein the cancer co-drug is administered every other week, preferably wherein administration of the cancer co-drug is initiated one to three days after the second weekly dose of the oncolytic vaccinia virus.

Other embodiments of the disclosure are discussed throughout this application. Any embodiment discussed with respect to one aspect of the disclosure applies to other aspects of the disclosure as well and vice versa. The embodiments in the Example section are understood to be embodiments of the disclosure that are applicable to all aspects of the disclosure.

The terms "inhibiting," "reducing," or "prevention," or any variation of these terms, when used in the claims and/or the specification includes any measurable decrease or complete inhibition to achieve a desired result.

As used herein, the term "combination" means the combined administration of the anti-cancer agents, namely the oncolytic vaccinia virus and the cancer co-drug, which can be dosed independently or by the use of different fixed combinations with distinguished amounts of the combination partners, i.e. simultaneously or at different time points. The term "combination" also defines a "kit" comprising the combination partners which can e.g. be administered simultaneously or chronologically staggered, that is at different time points and with equal or different time intervals for any part of the kit. Preferably, the time intervals are chosen such that the combination of agents shows a synergistic effect. As used herein, the term "synergistic" or "synergy" means that the effect achieved with the combinations of anticancer agents encompassed in this disclosure is greater than the sum of the effects that result from using anti-cancer agents namely the oncolytic vaccinia virus and the cancer co-drug, as a monotherapy. Advantageously, such synergy provides greater efficacy at the same doses, and/or prevents or delays the build-up of multi-drug resistance.

The term "cancer co-drug", includes any anti-cancer drug activatable by a carboxylesterase and any topoisomerase. Topoisomerase inhibitors include topoisomerase I inhibitors and topoisomerase II inhibitors in free form or in the form of a pharmaceutically acceptable salt. Examples of topoisomerase i inhibitors include, but are not limited to, irinotecan (e.g. irinotecan hydrochloride), also known as CPT-11; topotecan (e.g. topotecan hydrochloride), gimatecan (also known as LBQ707), camptothecin and its derivatives, 9-nitrocamptothecin and the camptothecin conjugate PNU-166148 (compound A1 in WO 99/17804); 10-hydroxycamptothecin acetate salt; etoposide; idarubicin hydrochloride; teniposide; doxorubicin; epirubicin hydrochloride; mitoxantrone hydrochloride; pentyl carbamate of p-aminobenzyl carbamate of doxazolidine (PPD); and daunorubicin hydrochloride. Irinotecan can be administered, e.g., in the form as it is marketed, e.g., under the trademark CAMPTOSAR™. Topotecan can be administered, e.g., in the form as it is marketed, e.g., under the trademark HYCAMTIN™. Topoisomerase II inhibitors include, without limitation, the anthracyclines, such as doxorubicin, including liposomal formulation, e.g., CAELYX™ daunorubicin, including liposomal formulation, e.g., DAUNOSOME™, epirubicin, idarubicin and nemorubicin; the anthraquinones mitoxantrone and losoxantrone; and the podophillotoxines etoposide and teniposide. Etoposide is marketed as ETOPOPHOS™; teniposide as VM 26-BRISTOL™; doxorubicin as ADRIBLASTIN™ or ADRIAMYCIN™; epirubicin as FARMORUBICIN™; idarubicin as ZAVEDOS™; and mitoxantrone as NOVANTRON?. In addition to topoisomerase inhibitors, other anti-cancer agents activated by carboxylesterases can also be used including paclitaxel-2-ethylcarbonate (which is converted to paclitaxel), capecitabine (which is converted to 5'-Deoxy-5-fluorocytidine (5-FU)), and generally any tertiary amidomethyl ester prodrugs of existing chemotherapeutics (which are converted to their carboxylic acid or amine forms).

The term "activatable cancer co-drug", includes any cancer drug that is transformed into its active form by a carboxylesterase, including topoisomerase inhibitors such as irinotecan. For example, the carboxylesterases catalyze the conversion of a topoisomerase or cancer drug from its parent form to its active metabolite.

The term "refractory cancer," as used herein refers to cancer that either fails to respond favorably to an antineoplastic treatment, or alternatively, recurs or relapses after responding favorably to an antineoplastic treatment. Accordingly, "a cancer refractory to a treatment" as used herein means a cancer that fails to respond favorably to, or resistant to, the treatment, or alternatively, recurs or relapses after responding favorably to the treatment. For example, such a prior treatment may be a chemotherapy regimen including irinotecan.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method, composition, or combination of the disclosure, and vice versa. Furthermore, compositions, combinations, and kits of the disclosure can be used to achieve methods of the disclosure.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The disclosure may be better understood by reference to one or more of these drawings in combination with the detailed description of specific embodiments presented herein.

FIGS. 1A & 1B show detection of the functional interferon protein in different SJ-815 virus clones by a hIFNb report cell assay. FIGS. 1C & 1D show detection of carboxylesterase function in different isolates of SJ-815 virus by p-NPA assay. Activity units were calculated by measuring absorbance at 405 nm at 5 minutes after addition of pNPA assay buffer minus absorbance measured at 0 minutes.

FIG. 2 shows a genetic map demonstrating the use of primers specifically targeting both flanking sides of the interferon transgene.

FIG. 3A shows images of plaques from U-2 OS cell seeded in 6-well plates and infected with the virus indicated after 24 hours of seeding. After 72 hours the cells were stained with crystal violet. FIG. 3B shows U-2 OS cells and BS-C-1 cells seeded in 6-well plates and infected with WR or SJ-815. Plaques were stained as in FIG. 3A. One picture from each representative experiment is shown.

FIG. 4A shows SJ-815 EC50 (pfu/cell) on human pancreatic and cervix cancer cell lines. Pancreatic cancer cell lines and HeLa cells were treated with either SJ-815 or control virus (WR.A34R.TK−) labeled as TK−, at different multiplicities of infection. Cell viability was assessed after 48 hours post-infection by CCK-8. The EC50 was determined and plotted. FIG. 4B shows replication of SJ-815 on human pancreatic and cervix cancer cells. Pancreatic cancer cell lines and HeLa cells were infected with SJ-815 or WR.A34R.TK– at 1 PFU/cell. After 48 hours post-infection the cells were harvested and the infectious virus produced in each cancer cell was determined by plaque assay in U-2 OS cells. The data from one representative experiment repeated 3 times in triplicate is presented.

FIG. 5A shows SJ-815 EC50 (pfu/cell) on human colon cancer cell lines. Colon cancer cell lines were treated with either SJ-815 or control virus (WR.A34R.TK–) labeled as TK–, at different multiplicities of infection. Cell viability was assessed after 48 hours post-infection by CCK-8. The EC50 was determined and plotted.

FIG. 5B shows replication of SJ-815 on human colon cancer cells. Colon cancer cell lines were infected with SJ-815 or WR.A34R.TK– at a multiplicity of 1 PFU/cell. After 48 hours post-infection the cells were harvested and the infectious virus produced in each pancreatic cell was determined by plaque assay in U-2 OS cells. The data from one representative experiment repeated 3 times in triplicate is presented.

FIG. 6A shows SJ-815 EC50 (pfu/cell) on human liver cancer cell lines. Liver cancer cell lines were treated with either SJ-815, mSJ-815 or control virus (WR.A34R.TK–) at different multiplicities of infection. Cell viability was assessed after 48 hours post-infection by CCK-8. The EC50 was determined and plotted. FIG. 6B shows replication of SJ-815 on human liver cancer cells. Liver cancer cell lines were infected with SJ-815, mSJ-815 and WR.A34R.TK– at a multiplicity of 1 PFU/cell. After 48 hours post-infection the cells were harvested and the infectious virus produced in each liver cell was determined by plaque assay in U-2 OS cells. The data from three different experiments run in triplicate is presented. Unpaired t-test was used to analyze the data *P<0.05 and **P<0.01.

FIGS. 7A-D show cell viability after increasing concentrations of virus treatment in myeloma and melanoma cancer cells. Myeloma and melanoma cancer cells SK-MEL 5 (FIG. 7A), SK-MEL 2 (FIG. 7B), RPMI8226 (FIG. 7C) and IM-9 (FIG. 7D) were treated with either SJ-815, mSJ-815 or control virus (WR.A34R.TK–) at different multiplicities of infection. Cell viability was assessed after 48 hours post-infection by CCK-8. The data from three different experiments run in triplicate is presented.

FIG. 8 shows replication of SJ-815 on human liver cancer cells. Myeloma and melanoma cancer cell lines were infected with SJ-815, mSJ-815 and WR.A34R.TK– at a multiplicity of 1 PFU/cell. After 48 hours post-infection the cells were harvested and the infectious virus produced in each cell line was determined by plaque assay in U-2 OS cells. The data from three different experiments run in triplicate is presented. Unpaired t-test was used to analyze the data *P<0.05 and **P<0.01.

FIGS. 9A-F shows cell viability after increasing concentrations of virus treatment in murine cancer cells: TIB-75 hepatocellular carcinoma (FIG. 9A), CT-26 colon carcinoma (FIG. 9B), B16-F10 skin melanoma (FIG. 9C), MC-38 colon carcinoma (FIG. 9D), RENCA renal adenocarcinoma (FIG. 9E), and 4T1 breast cancer (FIG. 9F) were treated with either mSJ-815 WR.mGM-CSF at different multiplicities of infection. Cell viability was assessed after 48 hours post-infection by CCK-8. The data from three different experiments run in triplicate is presented.

FIG. 10A shows survival of B57BL/6 mice with MC-38 colon cancer tumors treated with mSJ-815 and WR.TK–.mGMCSF virus via IV and IT. Kaplan-Meier curves for each treatment regimen are shown. Animals were sacrificed upon reaching the endpoint tumor volume of 1,500 mm³. FIG. 10B shows average of body weight for the different groups followed during the days after the first treatment injection. FIG. 10C shows tumor size in percentage relative to initial tumor size over time following treatment of mice harboring MC-38 tumors with mSJ-815 and WR.TK–.mGMCSF (Days 0, 3, 6 and 9), via IT and IV relative to control (PBS). Group averages are presented (n=5). None of the groups presented statistically significant differences with respect to the PBS (control) group, except on Days 21, 24 and 27, where the mSJ-815 group's smaller tumor volume was statistically significant from the PBS group, with a P<0.05 for Day 21 and Day 24 and P<0.01 for Day 27.

FIG. 11 shows tumor size over time following treatment of mice harboring MIA PaCa-2 tumors with SJ-815 intratumoral alone at increasing doses ($1\times10^5$, $1\times10^6$ and $1\times10^7$ PFU) (Days 0, 7 and 14), irinotecan intravenous treatment alone (Days 3, 10 and 17) and combination treatment with SJ-815 ($1\times10^6$) and irinotecan (above schedules combined) relative to control (PBS). Group averages are presented (n=3).

FIG. 12A shows Kaplan-Meier curves for each treatment regimen displayed. Animals were sacrificed upon reaching the endpoint tumor volume of 1,500 mm³. Data as analyzed by Long-rank (Mantel-Cox) test was significantly different with a P=0.002. FIG. 12B shows average and standard deviations of body weight for the different groups followed during the days after the first treatment injection.

FIG. 13A shows the average tumor size of B57BL/6 mice with B16-F10 melanoma tumors treated with different concentrations and doses of mSJ-815. The average tumor size per group was calculated and the SEM was plotted. The difference in the tendency of the plots was due to the animals that were sacrificed. Data was analyzed by One-way analysis of variance (ANOVA) followed by Dunnett's multiple comparison test and unpaired t test. The data was not statistically significant with a P=0.3755. FIG. 13B shows the size of the tumor in individual mice at day 12 after treatment. The data is statistically significant by one-way ANOVA with a P=0.0119. All the groups were statistically different from the PBS groups by Dunnet's multiple comparison test (P<0.05).

FIG. 14 shows Kaplan-Meier curves for each treatment regimen displayed. Animals were sacrificed upon reaching the endpoint tumor volume of 1,500 mm³. Data analyzed by Long-rank (Mantel-Cox) test was significantly different with a P<0.0001.

FIG. 15A shows the average tumor size of B57BL/6 mice with B16-F10 melanoma tumors treated with Vaccinia virus and CPT-11 alone and combination treatment with virus plus Irinotecan. Tumor volume values from a single dead mouse were excluded from this figure and analysis. The average in tumor size per group was calculated and the SEM was plotted. Data was analyzed by unpaired t-test. The data was statistically different between PBS (control group) and animals treated either with WR. A34R.TK– (WR.TK–), mSJ-815, or virus+CPT-11 in combination on Day 9 and 13. FIG. 15B shows the average size of the tumor per group until day 16 after treatment. Tumor volume values from a single dead mouse were excluded from this figure and analysis. The data was statistically significant by unpaired t-test. FIG. 15C shows the average tumor size of B57BL/6 mice with B16-F10 melanoma tumors treated with Vaccinia virus and CPT-11 alone and combination treatment with virus plus Irinotecan. The data displayed is the same as that shown in FIG. 15A, with the exception that tumor volume values from the single dead mouse are included. The average in tumor size per group was calculated and the SEM was plotted. Data was analyzed by unpaired t-test. FIG. 15D shows the average size of the tumor per group until day 16 after treatment.

The data displayed is the same as that shown in FIG. 15C, with the exception that tumor volume values from the single dead mouse are included.

FIG. 16 shows the average and standard deviations of body weight for the different groups of B57BL/6 mice with B16-F10 melanoma tumors treated with vaccinia virus and the combination with irinotecan. Mice were measured twice per week after treatment. Data was analyzed by one-way analysis of variance (ANOVA) followed by Dunnett's multiple comparison test. The data was not statistically significant with a P=0.1845. There was not a significant difference between any of the groups with Dunnett's multiple comparison test.

FIGS. 17A-D shows liver (FIG. 17A), kidney (FIG. 17B), brain (FIG. 17C), and lung (FIG. 17D) weight of B57BL/6 mice with B16-F10 melanoma tumors treated with mSJ-815 intratumoral or intravenous. Organs were collected at the endpoint, weighted and the weight was normalized against body weight.

FIGS. 18A & 18B shows spleen weight of B57BL/6 mice with B16-F10 melanoma tumors treated with mSJ-815 intravenous (FIG. 18A) or intratumoral (FIG. 18B). Spleens were collected at the endpoint, weighted and the weight was normalized against body weight.

FIG. 19 shows virus titers on the day of animal death within tumor, muscle, ovaries and liver. Bars represent standard deviation of the mean (SD).

MODE FOR THE INVENTION

Certain aspects of the disclosures described herein are based upon the surprising discovery that oncolytic vaccinia virus that has been engineered to express a cytokine and a carboxylesterase enzyme results in an unexpected improvement in the treatment of cancer, including when combined with a cancer co-drug. Without wishing to be bound by theory, expression of a cytokine such as the preferred human interferon beta 1 (hIFNb1) by the oncolytic vaccinia virus stimulates the anti-cancer immune response and enhances cancer selectivity.

It has been found that combination therapy with the oncolytic vaccinia virus described herein and a cancer co-drug, preferably an activatable cancer co-drug, results in unexpected improvement in the treatment of cancer. When administered simultaneously, sequentially or separately, the oncolytic vaccinia virus and the cancer co-drug, especially activatable cancer co-drugs, interact to kill cancer cells to a greater degree than by administration of either component by itself. This unexpected improvement should allow a reduction in the dose required of each component, leading to a reduction in the side effects and enhancement of the clinical effectiveness of the compounds and treatment. Cancer co-drugs such as irinotecan can cause significant side effects including frequent and severe gastrointestinal problems such as diarrhea, emesis, diaphoresis, abdominal cramping, hyperlacrimation, and rhinorrhea. The frequency and severity of symptoms is dose-related, with patients received higher doses demonstrating more severe symptoms. Thus, potential reduction in the cancer co-drug dose required when used in combination with the oncolytic vaccinia virus described herein would lead to a reduction in clinical side effects.

I. Oncolytic Vaccinia Virus

Certain aspects of the present disclosure relate to an oncolytic vaccinia virus that expresses a cytokine and a carboxylesterase enzyme and that preferably does not express an active thymidine kinase. Vaccinia virus is a large, complex enveloped virus having a linear double-stranded DNA genome of about 190K bp and encoding for approximately 250 genes. Vaccinia virus is a large virus roughly 360 nm by 250 nm in size. Vaccinia is well-known for its role as a vaccine that eradicated smallpox. Post-eradication of smallpox, scientists have been exploring the use of vaccinia virus as a tool for delivering genes or as a vaccine into biological tissues (gene therapy and genetic engineering).

Vaccinia virus preferentially infects through the basolateral surface of cells, but its viral progeny are released from the apical surface. Polarized cells include, without limitation, epithelial cells, endothelial cells, immune cells, osteoclasts, neurons, and fibroblasts.

Vaccinia virus is unique among DNA viruses as it replicates only in the cytoplasm of the host cell. Therefore, the large genome is required to code for various enzymes and proteins needed for viral DNA replication. During replication, vaccinia produces several infectious forms which differ in their outer membranes: the intracellular mature virion (IMV), the intracellular enveloped virion (IEV), the cell-associated enveloped virion (CEV) and the extracellular enveloped virion (EEV). IMV is the most abundant infectious form and is thought to be responsible for spread between hosts. On the other hand, the CEV is believed to play a role in cell-to-cell spread and the EEV is thought to be important for long range dissemination within the host organism. The oncolytic vaccinia virus of the present disclosure can optionally be modified to enhance EEV output including by mutating the A34R gene, which is known to produce enhanced amounts of the extracellular enveloped form (EEV) of vaccinia virus Any known oncolytic strain of vaccinia virus may be used as the vaccinia virus component of the compositions and combinations of the disclosure. In preferred embodiments, the oncolytic vaccinia virus of the present disclosure is a Copenhagen, Western Reserve, Lister, or Wyeth strain, most preferably a Western Reserve or Wyeth strain. Other strains which have been isolated and characterized from infected individuals or through bioselection methods selecting for tumor specific targeting properties may also be used.

The oncolytic vaccinia virus of the present disclosure can be engineered to express a foreign protein such as granulocyte-macrophage colony stimulating factor, or GM-CSF. GM-CSF is a protein secreted by macrophages that stimulates stem cells to produce granulocytes (neutrophils, eosinophils, and basophils) and macrophages. Human GM-CSF is glycosylated at amino acid residues 23 (leucine), 27 (asparagine), and 39 (glutamic acid) (see U.S. Pat. No. 5,073,627, incorporated herein by reference).

In some embodiments, the vaccinia virus is engineered to express a cytosine deaminase protein. Cytosine deaminase catalyzes the hydrolysis of cytosine to uracil. Cytosine deaminase plays a role in the pyrimidine salvage pathway, which permits the cell to utilize cytosine for pyrimidine nucleotide synthesis. Cytosine deaminase is also able to catalyze deamination of isoguanine, a mutagenic oxidation product of adenine in DNA, and of isocytosine and catalyzes the conversion of 5-fluorocytosine (5FC) to 5-fluorouracil (5FU), allowing the creation of a cytotoxic chemotherapeutic agent from a non-cytotoxic precursor.

In some embodiments, the vaccinia virus is engineered to express a somatostatin receptor type 2 protein. Somatostatin receptor type 2 is the receptor for somatostatin-14 and -28. Somatostatin receptor type 2 is coupled via pertussis toxin sensitive G proteins to inhibition of adenylyl cyclase. In also stimulates phosphotyrosine phosphatase and PLC, inhibits calcium entry by suppressing voltage-dependent calcium channels, inhibits cell growth through enhancement of MAPK1 and MAPK2 phosphorylation, stimulates neuronal migration and axon outgrowth, mediates negative regulation of insulin receptor signaling through PTPN6, and inactivates SSTR3 receptor function following heterodimerization.

The oncolytic vaccinia virus may be engineered to lack one or more functional genes in order to increase the cancer selectivity of the virus. In preferred embodiments, the oncolytic vaccinia virus is engineered to lack TK activity. A TK-deficient vaccinia virus requires thymidine triphosphate for DNA synthesis, which leads to preferential replication in dividing cells (particularly cancer cells). In another aspect, the oncolytic vaccinia virus may be engineered to lack vaccinia virus growth factor (VGF). This secreted protein is produced early in the infection process, acting as a mitogen to prime surrounding cells for infection. In another aspect, the oncolytic vaccinia virus may be engineered to lack both VFG and TK activity. In other aspects, the oncolytic vaccinia virus may be engineered to lack one or more genes involved in evading host interferon (IFN) response such as E3L, K3L, B18R, or B8R. In some preferred embodiments, the oncolytic vaccinia virus is a Western Reserve or Wyeth strain and lacks a functional TK gene. In other embodiments, the oncolytic vaccinia virus is a Western Reserve strain lacking a functional B18R and/or B8R gene.

In some embodiments, the oncolytic vaccinia virus lacks a functional TK gene and expresses human GM-CSF. In a preferred embodiment, the oncolytic vaccinia virus is a Wyeth strain oncolytic vaccinia virus that lacks a functional TK gene and expresses human GM-CSF.

A. Carboxylesterase Enzymes

The oncolytic vaccinia virus component of the combination can be engineered to express a carboxylesterase. Carboxylesterases are serine esterase enzymes primarily in the liver (carboxylesterase 1) and intestine (carboxylesterase 2) thought to be involved in the detoxification of a variety of xenobiotics. Carboxylesterases as used herein include any enzyme that catalyzes the conversion of irinotecan to the active metabolite SN-38, such as butyrylcholinesterase. SN-38, like irinotecan is a topoisomerase I inhibitor, but is ~100 to 1000 times more active than the parent drug. Only a small percentage of irinotecan is converted to SN-38 in human cancer patients receiving standard treatment with irinotecan. The carboxy terminal four amino acids of carboxylesterase 1 (HIEL) and carboxylesterase 2 (HTEL), cause the enzyme to be retained in the cell. Removal of these terminal four amino acids causes the enzyme to be secreted.

The present application demonstrates that combination therapy with irinotecan and a vaccinia virus genetically engineered to express a carboxylesterase results in a tumor-specific increase in the conversion of irinotecan to SN-38. A significant decrease in cell viability in a variety of cell lines following infection of the cells with vaccinia virus expressing carboxylesterase 2 compared to the same virus not expressing the carboxylesterase trans-gene was observed. Superior results were observed across several human cancer lines when the vaccinia virus expressed carboxylesterase 2.

In a preferred embodiment, the oncolytic virus expresses human carboxylesterase 2 (e.g. UniProt Accession Number 000748 incorporated herein by reference). In some embodiments, the vaccnia virus is engineered to express a polypeptide at least 80%, at least 85%, at least 90%, at least 95% or at least 99% identical to human carboxylesterase 2. In other embodiments, the onocolytic vaccinia virus expresses rabbit carboxylesterase 2 (UniProt Accession Number P14943 incorporated herein by reference) or a polypeptide at least 80%, at least 85%, at least 90%, at least 95% or at least 99% identical thereto. In related embodiments, the vaccinia virus expresses carboxylesterase 2 comprising a deletion of the carboxy terminal four amino acids so that the carboxylesterase is secreted.

In some preferred embodiments, the carboxylesterase enzyme comprises a C-terminal retention sequence. In some embodiments, the C-terminal retention sequence is HTEL (SEQ ID NO: 1). In some embodiments, the carboxylesterase enzyme does not comprise a C-terminal retention sequence. In some embodiments, the carboxylesterase enzyme is CES2, preferably human CES2 (hCES2). In some embodiments, expression of the carboxylesterase enzyme is under control of a late-early VACV p7.5 promoter, a vaccinia modified H5 (mH5) promoter, a vaccinia short synthetic early-late pS promoter, a pC11R promoter, a pF11L promoter, a psFJ1-10 synthetic early promoter, a pHyb synthetic early promoter, any native vaccinia early promoters, and a Late-Early Optimized (LEO) promoter.

B. Cytokines

In certain embodiments, the oncolytic viruses for use in the compositions, combinations and methods of the present disclosure may be engineered to express a cytokine.

Cytokines and chemokines can have potent antitumoral effects (Vicari et al., 2002; Homey et al., 2002). These effects can be on tumor cells themselves directly or they can be indirect through effects on non-cancerous cells. An example of the latter is TNF, which can have antitumoral effects by causing toxicity to tumor-associated blood vessels; this leads to a loss of blood flow to the tumor followed by tumor necrosis. In addition, cytokines and chemokines can act to recruit (and in some cases activate) immune effector cells such as neutrophils, eosinophils, macrophages and/or lymphocytes. These immune effector cells can cause tumor destruction by a number of mechanisms. These mechanisms include the expression of antitumoral cytokines, expression of fas-ligand, expression of perforin and granzyme, recruitment of natural killer (NK) cells, etc. The inflammatory response can eventually lead to the induction of systemic tumor-specific immunity. Finally, many of these cytokines or chemokines can act in combination with chemotherapy or radiation therapy to destroy tumors.

Clinically effective systemic administration of recombinant versions of these immunostimulatory proteins is not feasible due to (1) induction of severe toxicity with systemic administration and (2) local expression within tumor tissue is needed to stimulate local infiltration and antitumoral effects. Approaches are needed to achieve high local concentrations of these molecules within tumor masses while minimizing levels in the systemic circulation. Viruses can be engineered to express cytokine or chemokine genes in an attempt to enhance their efficacy. Expression of these genes from replication-selective vectors has potential advantages over expression from nonreplicating vectors. Expression from replicating viruses can result in higher local concentrations within tumor masses; in addition, replicating viruses can help to induce antitumoral immunity through tumor cell destruction/oncolysis and release of tumor antigens in a proinflammatory environment.

In some embodiments, the cytokine is selected from the group consisting of interferon-beta-1 (preferably human), IL-1α, IL-2, IL-3, IL-4, IL-5, IL-6, IL-7, IL-8, IL-9, IL-10, IL-12, IL-13, IL-14, IL-15, IL-17, IL-18, IL-21, IL-23, IL-24 CCL3, CCL5, and CXCR4. In certain embodiments, the cytokine is interferon-beta-1, preferably human. Human interferon beta, a type I interferon, is a 166 amino acid glycosylated protein which is secreted by fibroblasts in response to viral infection or exposure to double-stranded RNA. Interferon beta signals through a receptor composed of two chains: interferon-alpha receptor 1 (IFNAR1) and interferon-alpha receptor 2 (IFNAR2). Upon binding to the receptor, IFNb activates the JAK/STAT pathways, which leads to phosphorylation of STAT1 and STAT2. The STAT proteins subsequently dimerize, associate with interferon regulatory factor 3 (IRF3), and bind to interferon response elements within the cell nucleus. These elements serve to stimulate interferon responsive genes, leading to the downstream effects of interferon beta. Interferon beta possesses anti-viral and antiproliferative activity and has been used for the chemotherapy of certain types of tumors and in treating multiple sclerosis. Expression of IFN-beta-1 by the oncolytic vaccinia virus described herein stimulates the anticancer immune response and enhances cancer selectivity.

In some embodiments, expression of the cytokine is under control of a late-early VACV p7.5 promoter, a vaccinia modified H5 (mH5) promoter, a vaccinia short synthetic early-late pS promoter, a pC11R promoter, a pF11L promoter, a psFJ1-10 synthetic early promoter, a pHyb synthetic early promoter, any native vaccinia early promoters, and a Late-Early Optimized (LEO) promoter. Specific Exemplary Embodiments In a particularly preferred embodiment, the oncolytic vaccinia virus is SJ-815. SJ-815 is an attenuated transgenic oncolytic vaccinia virus derived from Western Reserve Vaccinia parental strain WR A34R K151E. WR A34R K151E contains the A34R gene with a K151E mutation to enhance EEV production (Blasco 1993). SJ-815 was derived by inserting the genes for human CES2 and human IFNbeta1 into the thymidine kinase (TK) gene of the parental virus (under the control of the synthetic early-late and p7.5 early-late promoters, respectively), thereby rendering the TK gene inactive. Inactivation of the TK gene has been shown to decrease the virulence of vaccinia virus and to increase tumor specific replication.

In another preferred embodiment, the oncolytic vaccinia virus is an attenuated transgenic oncolytic vaccinia virus derived from a Western Reserve Vaccinia parental strain with a wild-type (WT) A34R gene. This strain is derived by inserting the genes for human CES2 and human IFNbeta1 into the thymidine kinase (TK) gene of the parental virus (under the control of the synthetic early-late and p7.5 early-late promoters, respectively), thereby rendering the TK gene inactive. Inactivation of the TK gene has been shown to decrease the virulence of vaccinia virus and to increase tumor specific replication.

In a particularly preferred embodiment for use in mouse models, the oncolytic vaccinia virus is mSJ-815. mSJ-815 is an attenuated transgenic oncolytic vaccinia virus derived from Western Reserve Vaccinia parental strain WR A34R K151E. WR A34R K151E contains the A34R gene with a K151E mutation to enhance EEV production (Blasco 1993). SJ-815 was derived by inserting the genes for human CES2 and mouse IFNbeta1 into the thymidine kinase (TK) gene of the parental virus (under the control of the synthetic early-late and p7.5 early-late promoters, respectively), thereby rendering the TK gene inactive. Inactivation of the TK gene has been shown to decrease the virulence of vaccinia virus and to increase tumor specific replication.

II. Methods of Using the Disclosed Compositions

Oncolytic vaccinia viruses according to the present disclosure may be administered locally, regionally or systemically. For example, without limitation, oncolytic vaccinia viruses according to the disclosure can be administered intravascularly (intraarterially or intravenously), intratumorally, intramuscularly, intradermally, intraperitoneally, subcutaneously, orally, parenterally, intranasally, intratracheally, percutaneously, intraspinally, ocularly, or intracranially. Preferably, the vaccinia virus is administered intravascularly and/or intratumorally. Intratumoral administration generally entails injection into a tumor mass or into tumor associated vasculature. In certain aspects, the tumor is imaged prior to or during administration of the virus.

Oncolytic vaccinia viruses according to the disclosure may be administered in a single administration or multiple administrations. The virus may be administered at dosage of $1\times10^5$ plaque forming units (PFU), $5\times10^5$ PFU, at least $1\times10^6$ PFU, $5\times10^6$ or about $5\times10^6$ PFU, $1\times10^7$, at least $1\times10^7$ PFU, $1\times10^8$ or about $1\times10^8$ PFU, at least $1\times10^8$ PFU, about or at least $5\times10^8$ PFU, $1\times10^9$ or at least $1\times10^9$ PFU, $5\times10^9$ or at least $5\times10^9$ PFU, $1\times10^{10}$ PFU or at least $1\times10^{10}$ PFU, $5\times10^{10}$ or at least $5\times10^{10}$ PFU, $1\times10^{11}$ or at least $1\times10^{11}$, $1\times10^{12}$ or at least $1\times10^{12}$, $1\times10^{13}$ or at least $1\times10^{13}$. For example, the virus may be administered at a dosage of between about $10^7$-$10^{13}$ pfu, between about $10^8$-$10^{13}$ pfu, between about $10^9$-$10^{12}$ pfu, or between about $10^8$-$10^{12}$. Preferably, the virus is administered at a dosage of between $10^7$ and $10^{10}$ pfu.

It is contemplated that a single dose of virus refers to the amount administered to a subject or a tumor over a 0.1, 0.5, 1, 2, 5, 10, 15, 20, or 24 hour period, including all values there between. The dose may be spread over time or by separate injection. Typically, multiple doses are administered to the same general target region, such as in the proximity of a tumor or in the case of intravenous administration a particular entry point in the blood stream or lymphatic system of a subject. In certain aspects, the viral dose is delivered by injection apparatus comprising a needle providing multiple ports in a single needle or multiple prongs coupled to a syringe, or a combination thereof. A single dose of the vaccinia virus may be administered or the multiple doses may be administered over a treatment period which may comprise 1, 2, 3, 4, 5, 6, 7, 8, 9, 10, 11, 12 or more weeks. For example, the vaccinia virus may be administered every other day, weekly, every other week, every third week for a period of 1, 2, 3, 4, 5, 6 or more months.

Vaccinia virus may be propagated using the methods described by Earl and Moss in Ausubel et al., 1994 or the methods described in WIPO Publication No. WO2013/022764, both of which are incorporated herein by reference for their methods of propagation of vaccinia virus, but not any defined terms therein.

III. Cancer Co-DRUGS

Cancer co-drugs useful in combination with an oncolytic vaccinia virus include inhibitors of topoisomerases I and II. It will be understood that reference to topoisomerase inhibitors is meant to include their pharmaceutically acceptable salts. If the topoisomerase inhibitor has at least one basic group, it can form acid addition salts. Topoisomerase inhibitors having an acid group can also form salts with bases. Topoisomerase inhibitors and their salts may also be used in the form of a hydrate or include other solvents used e.g. for crystallization.

Topoisomerase I inhibitors include camptothecin and its derivatives such as irinotecan and topotecan, marine alkaloids such as lamellarin D (3,11-Dihydroxy-14-(4-hydroxy-3-methoxyphenyl)-2,12-dimethoxy-6H-chromeno[4',3':4,5] pyrrolo[2,1-a]isoquinolin-6-one) and idenoisoquinoline analogues such as indotecan (also called LMP400 or 2,3-dimethoxy-6-(3-morpholinopropyl)-5H-[1,3]dioxolo[4',5': 5,6]indeno[1,2-c]isoquin oline-5,12(6H)-dione), indimitecan (also called LMP776 or 6-(3-(1H-imidazol-1-yl)

propyl)-2,3-dimethoxy-6,6a-dihydro-5H-[1,3]dioxolo[4',5': 5,6]indeno[1,2-c]isoquinoline-5,12(12aH)-dione) and NSC-706744.

Topoisomerase II inhibitors include etoposide (also called VP-16), teniposide, doxorubicin, daunorubicin, epirubicin, idarubucin, mitoxantrone, amsacrine, ellipticines, aurintricarboxylic acid, HU-331 and ICRF-193, ICRF-187, and merbarone. Etoposide phosphate may be administered to a human in a dosage range varying from about 25 to 115 mg/m$^2$. Teniposide may be administered to a human in a dosage range of about 75 to 150 mg/m$^2$ every two weeks. Doxorubucin may be administered to a human in a dosage range of about 10 to 100 mg/m$^2$. Epirubicin may be administered to a human in a dosage range varying from about 10 to 200 mg/m$^2$ e.g. 100 mg/m$^2$ i.v. every 3-4 weeks. Idarubucin may be administered to a human in a dosage of about 0.5 to 50 mg/m$^2$.

Camptothecin derivatives are preferred topoisomerase inhibitors for use in the combination. Camptothecin derivatives are anticancer agents which inhibit topoisomerase I. These compounds are usually administered by injection, more particularly intravenously in the form of a sterile solution or emulsion; however, they can also be administered orally, in solid or liquid formulations. Representative camptothecin derivatives useful in the present disclosure include irinotecan, topotecan (also called Hycamtin or S)-10-[(dimethylamino)methyl]-4-ethyl-4,9-dihydroxy-1H-pyrano[3',4':6,7]indolizino[1,2-b]quinoline-3,14(4H,12H)-dione monohydrochloride), DB-67 (also called AR67 or 7-t-butyldimethylsilyl-10-hydroxycamptothecin), BNP-1350 (7-[(2-trimethylsilyl)ethyl]-20(S)-camptothecin), exatecan ((1S,9S)-1-Amino-9-ethyl-5-fluoro-1,2,3,9,12,15-hexahydro-9-hydroxy-4-methyl-10H, 13H-benzo(de)pyrano (3',4':6,7)indolizino(1,2-b)quinoline-10,13-dione), lurtotecan (also called GI147211 or 7-(4-methylpiperazineomethylene)-10,11-ethylenedioxy-20(S)-camptothecin dihydrochloride), ST-1481 (7-t-butoxyiminomethylcamptothecin), and CKD-602 ((20S)-7-(2-isopropylamino)-ethylcamptothecin). Topotecan can be administered to a human in a dosage range varying from about 1 to 5 mg/m$^2$ e.g. at 1.5 mg/m$^2$ by intravenous infusion over 30 minutes daily for 5 consecutive days.

Irinotecan (also known as CPT-11, Camptosar, or (S)-4,11-diethyl-3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate) is a particularly preferred camptothecin derivative. Irinotecan is a prodrug that is converted by carboxylesterase enzymes to the active drug known as SN-38 (7-ethyl-10-hydroxy-camptothecin) (Satoh T. et al., Biol. Pharm. Bull., 17:662-664 (1994). It acts by preventing re-ligation of the DNA strand by binding to topoisomerase I-DNA complex and causes double-strand DNA breakage and cell death. Irinotecan has been demonstrated to be particularly effective in the treatment of cancer either alone or in combination with other agents such as 5-fluorouracil (5-FU) and oxaliplatin. Irinotecan is in fact the reference treatment in metastatic cancer after failure on prior 5-FU treatment. In this respect, irinotecan has been shown to be at least as active as the standard 5-FU/folinic acid (FA) in patients with metastatic cancer who had not previously received chemotherapy. In addition to colon cancer, activity has been observed in ovarian cancer, lung cancer, gastric cancer, oesophageal cancer and cervical cancer.

Irinotecan (preferably as a hydrochloride salt) may be administered according to treatment protocols known in the art taking into account the expression of the carboxylesterase by the oncolytic vaccinia virus, which will increase the local concentration in the tumor environment. For example, when used as a single agent in the treatment of cancer, irinotecan is usually administered at a starting dose of 350 mg/m$^2$ intravenously over 90 minutes every three weeks which can be adjusted as low as 200 mg/m$^2$ in 50 mg/m$^2$ decrements depending on a patient's tolerance, or alternatively is administered at a starting dose of 125 mg/m$^2$ intravenously over 90 minutes once a week, which can adjusted as high as 150 mg/m$^2$ or to as low as 50 mg/m$^2$ in 25-50 mg/m$^2$ decrements depending on a patient's tolerance, for as long as the patient continues to experience clinical benefit. When used in combination with 5-FU and FA, irinotecan is generally administered at 125 mg/m$^2$ intravenously over 90 minutes once a week for four doses or is administered at a dose of 180 mg/m$^2$ intravenously over 90 minutes every other week for three doses. Thus, according to the disclosure, irinotecan may be administered at a dose range of 50-350 mg/m$^2$ e.g. a 90 minute continuous infusion once per week at a dose of 125 mg/m$^2$ or a 90 minute continuous infusion every other week at a dose of 180 mg/m$^2$. Irinotecan dosing can continue for as long as a clinical benefit is experienced.

In addition to topoisomerase inhibitors, other anti-cancer agents activated by carboxylesterases can also be used including paclitaxel-2-ethylcarbonate (which is converted to paclitaxel), capecitabine (which is converted to 5'-Deoxy-5-fluorocytidine (5-FU)), and generally any tertiary amidomethyl ester prodrugs of existing chemotherapeutics (which are converted to their carboxylic acid or amine forms). Dosing can suitably adapted for these other anti-cancer agents taking into account the expression of the carboxylesterase by the oncolytic vaccinia, which will increase the local concentration in the tumor environment.

IV. Treatment Regimens and Pharmaceutical Formulations of the Combinations

Some aspects of the present disclosure relate to methods for treating cancer in a mammal by administering to the mammal an effective amount of a synthetic oncolytic vaccinia virus that expresses a carboxylesterase enzyme and a cytokine and that preferably does not express an active thymidine kinase, ideally for use in conjunction with a cancer co-drug. Some aspects of the present disclosure relate to methods for treating cancer in a mammal by administering an effective amount of a combination containing (a) a composition comprising a synthetic oncolytic vaccinia virus that expresses a cytokine and a carboxylesterase enzyme and that preferably does not express an active thymidine kinase, and (b) cancer co-drug.

The oncolytic vaccinia virus and the cancer co-drug may be administered simultaneously, sequentially or separately. Simultaneous administration may, e.g., take place in the form of one fixed combination comprising these agents, or by simultaneously administering each agent in independent formulations. Sequential use (administration) preferably means that the oncolytic vaccinia virus and the cancer co-drug are administered at different time points, that is, in a chronically staggered manner, preferably such that the combination is more effective than when the oncolytic vaccinia virus and the cancer co-drug are independently administered. Separate use (administration) preferably means that the oncolytic vaccinia virus and the cancer co-drug are administered independently of each other at different time points. The present disclosure is therefore to be understood as embracing all such regimes of simultaneous or alternating treatment and the term "administering" is to be interpreted accordingly.

If the oncolytic virus and the cancer co-drug are not administered simultaneously, the order of administration of the oncolytic virus and the cancer co-drug may be varied. Thus, the oncolytic virus may be administered first followed by administration of the cancer co-drug or the cancer co-drug may be administered first followed by the oncolytic virus. In embodiments where the oncolytic vaccinia virus and the cancer co-drug are not administered simultaneously, each agent is preferably administered such that an advantageously combined effect on the cell is obtained. In such instances, it is contemplated that the agents are administered within the same general time frame and preferably within two weeks, more preferably within one week, of each other. In some situations, it may be desirable to extend the time period for treatment significantly where several days (e.g. 2, 3, 4, 5, 6 or 7) lapse between the respective administrations. In a preferred combination, sequential administration of the oncolytic virus and the cancer co-drug comprises first administering one or more doses of the oncolytic virus followed by administration of one or more doses of the cancer co-drug, preferably with an intervening period of 14 or fewer (e.g. 13, 12, 11, 10, 9, 8, 7, 6, 5, 4, 3, 2, 1 or 0) days between administration of the respective agents. By "intervening period" it is meant a time period beginning from the end of the last dose of the oncolytic virus up until the beginning of the first dose of cancer co-drug. In embodiments in which the intervening period is 0 days, the cancer co-drug is administered immediately following the last dose of the oncolytic virus.

A particularly preferred sequential treatment protocol comprises weekly administration of oncolytic virus staggered with every other week administration of cancer co-drug, wherein the oncolytic virus is administered first with an intervening period of from 1 to 3 days. For example, every other week administration of the cancer co-drug may begin 1 to 3 days after the second weekly dose of oncolytic virus:

Oncolytic virus (Days 1, 8, 15, 22, 29?)
Cancer co-drug (Days 9, 23, 37, 51, 65?).

Administration of the oncolytic vaccinia virus and the cancer co-drug will follow general protocols for the administration of each particular therapy, taking into account the toxicity, if any, of the treatment. It is expected that the treatment cycles would be repeated as necessary. It also is contemplated that various standard therapies, as well as surgical intervention, may be applied in addition to therapy of the present disclosure.

Treatment regimens may vary and often depend on tumor type, tumor location, disease progression, and health and age of the patient. Certain types of tumor will require more aggressive treatment, while at the same time, certain patients cannot tolerate more taxing protocols. The clinician will be best suited to make such decisions based on the known efficacy and toxicity (if any) of the therapeutic formulations.

In certain embodiments, the tumor being treated may not, at least initially, be resectable. Treatment with a combination therapy of the disclosure may increase the resectability of the tumor due to shrinkage at the margins or by elimination of certain particularly invasive portions. Following treatment, resection may be possible. Additional treatments subsequent to resection will serve to eliminate microscopic residual disease at the tumor site Determining a synergistic interaction between one or more components, the optimum range for the effect and absolute dose ranges of each component for the effect may be definitively measured by administration of the components over different w/w ratio ranges and doses to patients in need of treatment. For humans, the complexity and cost of carrying out clinical studies on patients renders impractical the use of this form of testing as a primary model for synergy. However, the observation of synergy in one species can be predictive of the effect in other species and animal models exist, as described herein, to measure a synergistic effect and the results of such studies can also be used to predict effective dose and plasma concentration ratio ranges and the absolute doses and plasma concentrations required in other species by the application of pharmacokinetic/pharmacodynamic methods. Established correlations between tumor models and effects seen in man suggest that synergy in animals may e.g. be demonstrated in the human xenograft tumor models as described in the Example below.

In certain aspects, the combination is used to treat cancer in mammal, wherein the cancer selected from the group consisting of brain cancer, head & neck cancer, esophageal cancer, skin cancer, lung cancer, thymic cancer, stomach cancer, colon cancer, liver cancer, ovarian cancer, uterine cancer, bladder cancer, renal cancer, testicular cancer, rectal cancer, breast cancer, and pancreatic cancer. In some embodiments, the combination is used to treat a cancer selected from the group consisting of colorectal cancer, lung cancer, melanoma, pancreatic cancer, ovarian cancer, cervical and liver cancer.

The methods include administering therapeutically effective amounts of an oncolytic vaccinia virus and a cancer co-drug. A therapeutically effective amount is defined as that amount sufficient to induce oncolysis—the disruption or lysis of a cancer cell. Preferably, the oncolytic vaccinia virus and the cancer co-drug are administered in synergistically effective amounts. The term includes the slowing, inhibition, or reduction in the growth or size of a tumor and includes the eradication of the tumor in certain instances. In certain aspects an effective amount of vaccinia virus results in systemic dissemination of the therapeutic virus to tumors, e.g., infection of non-injected tumors.

V. Embolic Agents

Some aspects of the present disclosure relate to methods for treating cancer in a mammal by introducing into the vasculature of a mammal a composition containing a synthetic oncolytic vaccinia virus that expresses a cytokine and a carboxylesterase enzyme and that preferably does not express an active thymidine kinase, and a biocompatible microparticle or hydrophilic polymer gel agent suitable for active embolization. In some embodiments, the combination of an oncolytic vaccinia virus and a cancer co-drug are introduced into the vasculature. Some aspects of the present disclosure relate to methods for treating cancer in a mammal by (a) administering by introducing into the vasculature of a mammal a composition containing a synthetic oncolytic vaccinia virus that expresses a cytokine and a carboxylesterase enzyme and that preferably does not express an active thymidine kinase, and a biocompatible microparticle or hydrophilic polymer gel agent suitable for active embolization and (b) administering to the mammal a composition comprising an effective amount of a cancer co-drug. As above, the oncolytic vaccinia virus and the cancer co-drug may be administered simultaneously, sequentially or separately. Simultaneous administration may, e.g., take place in the form of one fixed combination comprising these agents, or by simultaneously administering each agent in independent formulations. Sequential use (administration) preferably means that the oncolytic vaccinia virus and the cancer co-drug are administered at different time points, that is, in a chronically staggered manner, preferably such that the combination is more effective than when the oncolytic vaccinia virus and the cancer co-drug are independently administered. Separate use (administration) preferably means that the oncolytic vaccinia virus and the cancer co-drug are administered independently of each other at different time points, preferably meaning that the oncolytic vaccinia virus and the cancer co-drug are administered such that no overlap of measurable blood levels of both agents are present in an overlapping manner (at the same time). Where administered independently, one or both may be administered via active embolization with a biocompatible microparticle or hydrophilic polymer gel agent suitable therefor. The present disclosure is therefore to be understood as embracing all such regimes of simultaneous or alternating treatment and the term "administering" is to be interpreted accordingly.

Numerous biocompatible microparticle or hydrophilic polymer gel agents can be used in the compositions, combinations, and methods of this disclosure. In a preferred embodiment, the biocompatible microparticle or hydrophilic polymer gel agents are selected from: degradable starch microparticles, polyvinyl alcohol microparticles, gelatin foam microparticles, and sulfonated polyvinyl alcohol hydrogel microparticles.

Biocompatible microparticle or hydrophilic polymer gel agents ("embolic agents") can be either temporary or permanent. Exemplary temporary embolic agents include gelfoam, collagen, and thrombin. Exemplary permanent embolic agents include particles, such as polyvinyl alcohol particles (PVA) and embospheres, coils, such as pushable, injectable, detachable, mechanical, electrolytic, and hydrolytic coils, liquid agents, such as glue, onyx, alcohol, and ALGEL™ (a hydrogel, sugar-based polymer derived from alginate), and other agents, including amplatzer plugs, Gianturco-Grifka vascular occlusive device (GGVODs), and detachable balloons. Different embolic agents can be used depending on the size of the vessel to be embolized, the desired length of vessel occlusion following embolization, and whether embolized tissue should remain viable after occlusion. Given the extensive use of embolization, a skilled interventional radiologist would have no difficulty in selecting the appropriate type of agent, size range of agent, etc. to achieve the desired embolization. Vessel occlusion is useful in clinical scenarios such as traumatic injury and hemorrhage, or when repeated embolization procedures are desired, such may be desirable as in tumor embolization with oncolytic viruses as disclosed in this specification.

In one embodiment, the biocompatible microparticle or hydrophilic polymer gel agents are gelatin foam microparticles. Exemplary gelatin foam includes Gelfoam, produced by Alicon/Scion Medical Technologies. Gelfoam is a biological substance made from purified skin gelatin, and is formulated in sterile sheets or as a powder. Gelfoam has been used in embolization applications for over 30 years, and is a low cost, versatile embolic agent. Gelfoam slows blood flow by causing mechanical obstruction. Gelfoam powder consists of particulates that range in size from 150-1000?m and can aggregate to form larger conglomerate particles upon water absorption. Gelfoam sheets can be cut into numerous different sizes and shapes and formulated with other aqueous agents upon injection depending upon the desired application. Gelfoam slurry containing both a contrast agent and Gelfoam sponge can be used to form a "cast" of proximal embolized vessels, while Gelfoam torpedoes or cubes can be used for larger vessels. Gelfoam temporarily occludes vessels by slowing blood flow, increasing thrombus formation, and functioning as a scaffold for clots.

In one embodiment, the biocompatible microparticle or hydrophilic polymer gel agents are degradable starch microparticles. Exemplary degradable starch microparticles (DSM) are EMBOCEPTS particles produced by Pharmacept and SPHEREX particles produced by Mangle Life Sciences. EMBOCEPTS particles (Amilomer as the active substance) are cross-linked particles composed of hydrolyzed potato starch. These particles are suitable for temporary embolization, as they have a half-life of approximately 35 minutes and are degradable. SPHEREX particles are composed of DSM-S microparticles, sterilized and suspended in saline solution. Starch microparticles may be prepared from an aqueous solution of purified amylopectin-based starch of reduced molecular weight by forming an emulsion of starch droplets in an outer phase of polymer solution, converting the starch droplets to a gel, and drying the starch particles. A release-controlling shell is optionally also applied to the particles. Biodegradable microparticles, after parenteral administration, are dissolved in the body to form endogenic substances, ultimately, for example, glucose. The biodegradability can be determined or examined through incubation with a suitable enzyme, for example alpha-amylase, in vitro. The biodegradability can also be examined through parenteral injection of the microparticles, for example subcutaneously or intramuscularly, and histological examination of the tissue as a function of time. Biodegradable starch microparticles disappear normally from the tissue within a few weeks and generally within one week. In those cases in which the starch microparticles are coated with a release-controlling shell, for example coated, it is generally this shell which determines the biodegradability rate, which then, in turn, determines when alpha-amylase becomes available to the starch matrix.

In one embodiment, the biocompatible microparticle or hydrophilic polymer gel agents are polyvinyl alcohol (PVA) microparticles. Exemplary polyvinyl alcohol microparticles are produced by Boston Scientific Corporation (Natick, Mass.). PVA particles are made from a PVA foam sheet that is vacuum dried and scraped into particles. The particles are filtered with sieves and are available in sizes ranging from 100?m to 1100?m. Polyvinyl alcohol particles are irregular in size and shape, which promotes aggregation. After suspension, PVA particles can be oblong, oval, irregular, sharp, and angulated with small fragments after suspension. Polyvinyl alcohol particles deliver permanent occlusion by adhering to vessel walls and by blocking the smallest vessel into which they pass. PVA occlusion results in inflammatory reactions, local vessel necrosis, and subsequent vessel fibrosis.

In one embodiment, the biocompatible microparticle or hydrophilic polymer gel agents are sulfonated polyvinyl alcohol hydrogel microparticles. Exemplary sulfonated polyvinyl alcohol hydrogel microparticles are DC-Beads produced by Biocompatibles (UK, Surrey, UK). DC Beads are embolic microparticle products based on a polyvinyl alcohol hydrogel that has been modified with sulfonate groups. DC Beads have the ability to actively sequester anthracycline compounds in their salt form, such as doxorubicin HCl, from solution and release it in a controlled and sustained manner. A drug can be added immediately prior to embolization, allowing for a one-step procedure in which the drug and device are delivered at the same time, resulting in a sustained local delivery of the drug.

As mentioned above, one of skill in the art can readily select the appropriate size of the biocompatible microparticle or hydrophilic polymer gel agents based upon, among other factors, the size of the tumor vasculature and the nature of the desired embolization. In a preferred embodiment, the biocompatible microparticle or hydrophilic polymer gel agents are between 100 µm and 2000 µm in size. In a preferred embodiment, the biocompatible microparticle or hydrophilic polymer gel agents are between 150 and 350 µm in size. In one embodiment, the biocompatible microparticle or hydrophilic polymer gel agents are between 150 and 200 µm in size. In one embodiment, the biocompatible microparticle or hydrophilic polymer gel agents are between 200 and 250 µm in size. In one embodiment, the biocompatible microparticle or hydrophilic polymer gel agents are between 250 and 300 µm in size. In one embodiment, the biocompatible microparticle or hydrophilic polymer gel agents are between 300 and 350 µm in size.

In certain embodiments, the biocompatible microparticle or hydrophilic polymer gel agents are uniform in size. This means that the difference in diameter between individual particles is from about 0 µm to about 100 µm, from about 0 µm to about 50 µm, or from about 0 µm to about 25 µm. In some embodiments, the microparticles have differences in diameter of 100 µm or less, about 50 µM or less, about 25 µm or less, about 10 µm or less or about 5 µm or less.

VI. Methods of Embolization

In one aspect, the disclosure provides a method for active embolization of a vascular site in a mammal by introducing into the vasculature of a mammal an oncolytic virus of the disclosure and a biocompatible microparticle or hydrophilic polymer gel suitable for active embolization, optionally in combination with a cancer co-drug.

Introduction of the biocompatible microparticle or hydrophilic polymer gel agents, the oncolytic viruses and the compositions and combinations of the present disclosure typically carried out by injection into blood vessels near and around tumors. In certain embodiments, the biocompatible microparticle or hydrophilic polymer gel agents, the oncolytic viruses and the compositions and combinations of the present disclosure are introduced by a catheter. In other embodiments, the biocompatible microparticle or hydrophilic polymer gel agents, the oncolytic viruses and the compositions and combinations of the present disclosure are introduced through injection by a catheter attached to a syringe. In some embodiments, introduction is into a blood vessel that directly feeds a tumor or portion of a tumor. In other embodiments, introduction is directly to the site of action, for example into a blood vessel at the proximal end of the tumor. The biocompatible microparticle or hydrophilic polymer gel agent according to the present disclosure can be introduced already loaded with the oncolytic virus (i.e., the compositions of the present disclosure) and/or a cancer co-drug (i.e., the combinations of the present disclosure). In other embodiments, the biocompatible microparticle or hydrophilic polymer gel agents are introduced in combination with the oncolytic virus, wherein the virus is introduced prior, simultaneously or after the introduction of the biocompatible microparticle or hydrophilic polymer gel agents. When introduced, the biocompatible microparticle or hydrophilic polymer gel agents, the oncolytic viruses and the compositions and combinations of the present disclosure are suitable for injection. In specific embodiments, the biocompatible microparticle or hydrophilic polymer gel agents, the oncolytic viruses and the compositions and combinations of the present disclosure are sterile.

The biocompatible microparticle or hydrophilic polymer gel agents, the oncolytic viruses and the compositions and combinations of the present disclosure may be delivered using a catheter or microcatheter. The catheter delivering the biocompatible microparticle or hydrophilic polymer gel agents, the oncolytic viruses and the compositions and combinations of the present disclosure may be a small diameter medical catheter. Catheter materials compatible with the biocompatible microparticle or hydrophilic polymer gel agents, the oncolytic viruses and the compositions and combinations of the present disclosure may include polyethylene, fluoropolymers and silicone. Once a catheter is in place, the biocompatible microparticle or hydrophilic polymer gel agents, the oncolytic viruses, the compositions, or combinations of the present disclosure are introduced through the catheters slowly, typically with the assistance of fluoroscopic guidance. The biocompatible microparticle or hydrophilic polymer gel agents, the oncolytic viruses and the compositions and combinations of the present disclosure may be introduced directly into critical blood vessels or they may be introduced upstream of target vessels. The amount of the biocompatible microparticle or hydrophilic polymer gel agents or the compositions or combinations of the present disclosure introduced during an embolization procedure will be an amount sufficient to cause embolization, e.g., to reduce or stop blood flow through the target vessels. The amount of the biocompatible microparticle or hydrophilic polymer gel agents, the oncolytic viruses and the compositions and combinations of the present disclosure delivered can vary depending on, e.g., the total size or area of the vasculature to be embolized and the size and nature of the tumor. After embolization, another arteriogram may be performed to confirm the completion of the procedure. Arterial flow will still be present to some extent to healthy body tissue proximal to the embolization, while flow to the diseased or targeted tissue is blocked. Further, a vasodilator (e.g., adenosine) may be administered to the patient beforehand, simultaneously, or subsequently, to facilitate the procedure.

One of skill in the medical or embolizing art will understand and appreciate how the biocompatible microparticle or hydrophilic polymer gel agents, the oncolytic viruses and the compositions and combinations of the present disclosure as described herein can be used in various embolization processes by guiding a delivery mechanism to a desired vascular body site, and delivering an amount of the biocompatible microparticle or hydrophilic polymer gel agents, the oncolytic viruses, the compositions, or the combinations of the present disclosure to the site, to cause restriction, occlusion, filling, or plugging of one or more desired vessels and reduction or stoppage of blood flow through the vessels. Factors that might be considered, controlled, or adjusted for, in applying the process to any particular embolization process might include the chosen biocompatible microparticle or hydrophilic polymer gel agent, oncolytic virus, composition and/or combination of the present disclosure (e.g., to account for imaging, tracking, and detection of a radiopaque particle substrate); the biocompatible microparticle or hydrophilic polymer gel agents, the oncolytic viruses and the compositions and combinations of the present disclosure delivered to the body site; the method of delivery, including the particular equipment (e.g., catheter) used and the method and route used to place the dispensing end of the catheter at the desired body site, etc. Each of these factors will be appreciated by one of ordinary skill, and can be readily dealt with to apply the described methods to innumerable embolization processes.

VII. Additional Anticancer Therapeutics

One or more additional chemotherapeutic agents may be administered with the compositions and combinations of the present disclosure, including, without limitation, 5-fluorouracil (FU), folinic acid (FA) (or leucovorin), methotrexate, capecitabine (Xeloda; an oral prodrug of 5-FU), oxaliplatin (Eloxatin), bevacizumab (Avastin), cetuximab (Erbitux) and panitumumab (Vectibix), in any combination. These agents may be administered according to known treatment protocols. Generally, the additional chemotherapeutic agent is administered intravenously, with the exception of capecitabine which is an oral formulation.

5-FU is typically administered with FA in order to increase 5-FU activity. In one aspect, 5-FU and FA are administered with the compositions or combinations of the present disclosure.

In a related aspect, 5-FU, FA and oxaliplatin are administered with the composition or combinations of the present disclosure. For example, a FOLFOX treatment protocol may be administered to a mammal with the compositions of the present disclosure. FOLFOX treatment employs 5-FU (400 mg/m$^2$ IV over 2 hours on day 1), FA (400 mg/m$^2$ IV over 2 hours on day 1) and oxaliplatin (1200 mg/m$^2$/day for 2 days continuous infusion) repeated every 2 weeks for 4 cycles. Alternatively a FLOX treatment protocol may be administered with the compositions of the present disclosure (oxaliplatin 85 mg/m$^2$ on days 1, 15 and 29 plus FA 500 mg/m$^2$ on days 1, 8, 15, 22, 29 and 36, followed by 5-FU 500 mg/m$^2$ on days 1, 8, 15, 22, 29 and 39 for 2 cycles).

In another related aspect, capecitabine and oxaliplatin are administered with the composition or combinations of the present disclosure, for example as a XELOX treatment regimen.

In another related aspect, a monoclonal antibody such as bevacizumab, cetuximab or panitumumab, optionally with 5-FU/FA, is administered with the composition or combinations of the present disclosure. Bevacizumab, which targets and inhibits vascular endothelial growth factor (VEGF) is an approved first-line treatment for patients with metastatic cancer. Cetuximab and Panitumumab target epidermal growth factor (EGFR).

In other aspects, methods of the disclosure further comprise administering an additional cancer therapy such as radiotherapy, hormone therapy, surgery and combinations thereof.

Radiotherapy includes, without limitation, n-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present disclosure, chemotherapy, radiotherapy, hormonal therapy, gene therapy, and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present disclosure may be used in conjunction with removal of superficial cancers, precancers, or incidental amounts of normal tissue.

Upon excision of part of or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

Another form of therapy for use in conjunction with the current methods includes hyperthermia, which is a procedure in which a patient's tissue is exposed to high temperatures (up to 106?F). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present disclosure or in combination with any other cancer therapy previously described. The use of hormones may be employed in the treatment of certain cancers such as breast, prostate, ovarian, or cervical cancer to lower the level or block the effects of certain hormones such as testosterone or estrogen.

VIII. Compositions And Formulations

A preferred method for the delivery of the oncolytic vaccinia virus to cancer or tumor cells is via intratumoral or intravascular injection. However, the pharmaceutical compositions disclosed herein may alternatively be administered parenterally, intradermally, intramuscularly, transdermally or even intraperitoneally as described in U.S. Pat. Nos. 5,543,158; 5,641,515 and 5,399,363 (each specifically incorporated herein by reference in its entirety).

Injection of the oncolytic vaccinia virus may be by syringe or any other method used for injection of a solution, as long as the expression construct can pass through the particular gauge of needle required for injection. A novel needleless injection system has recently been described (U.S. Pat. No. 5,846,233) having a nozzle defining an ampule chamber for holding the solution and an energy device for pushing the solution out of the nozzle to the site of delivery. A syringe system has also been described for use in gene therapy that permits multiple injections of predetermined quantities of a solution precisely at any depth (U.S. Pat. No. 5,846,225).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical. Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

EXAMPLES

The following are examples of methods and compositions of the present disclosure.

It is understood that various other embodiments may be practiced, given the general description provided above.

Example 1: Generation of a Recombinant Vaccinia Virus SJ-815 Expressing Human Carboxylesterase 2 and Interferon Beta Introduction A recombinant vaccinia virus, SJ-815, expressing human carboxylesterase 2 and human interferon beta 1 was generated by inserting these two genes into the thymidine kinase region of Western Reserve strain vaccinia virus. The parental vaccinia virus Western Reserve has a mutation in the A34R gene which is known to produce enhanced amounts of the extracellular enveloped form (EEV) of vaccinia virus.

The two foreign genes of interest were cloned into a transfer plasmid vector flanked by thymidine kinase (TK) from the vaccinia virus genome J2R. The transfer plasmid was then transfected into 143B cells that had been infected with vaccinia virus Western Reserve A34R. Homologous recombination occurred and recombinant virus was obtained in a cell lysate. For TK selection, the reagent 5-bromo-2'-deoxy uridine (BrdU) was used to isolate TK– virus, since in the presence of active TK, phosphorylated BrdU causes lethal mutations in viral DNA, thus theoretically permitting only recombinant virus to survive.

Materials and Methods

Virus

Vaccinia virus Western Reserve bearing a K151E mutation in A34R (WR A34R K151E) was chosen as the backbone of SJ-815 since the Western Reserve (WR) strain has been demonstrated to be more potent than Wyeth strain and is expected to improve the therapeutic index of oncolytic vaccinia virus. The lysine (K) to glutamic acid (E) mutation at codon 151 of the A34R region reduces the A34R protein's ability to retain EEV particles at the cell membrane. This mutation was included with the intention of enhancing recombinant vaccinia virus SJ-815's ability to affect metastatic tumor as well as solid tumor in situ.

The parental vaccinia virus was WR A34R K151E. The virus was further propagated in adherently cultured human cervix adenocarcinoma (HeLa) cells. The HeLa cells, taken from a cell bank derived from ATCC® # CCL-2, were maintained in complete growth medium (Dulbecco's Modified Eagle Medium (DMEM) containing 10% fetal bovine serum (FBS, Hyclone®, Cat # SH30919.03), 100 U/mL penicillin, and 100μ/mL streptomycin) and were passaged using porcine-sourced Trypsin with EDTA (Gibco, cat #15400-054). Three days post infection (at target MOI of 0.1), HeLa cells which showed full cytopathic effect were collected, supernatant was discarded, and intracellular virus was released from cells by homogenization. Released virus was semi-purified by centrifugation (Beckman Avanti J-E High speed centrifuge #369001, rotor JA-20.1, 12,000 rpm, 80 min, 4° C.), resuspended in 10 mM Tris pH 9.0, and stored in a deep freezer (−75±20° C.). The amplified virus was titered on U-2 OS cells to determine the concentration of plaque forming units (pfu).

Plasmid Vector

The plasmid vector used for homologous recombination was composed of the pSC65 plasmid bearing two transgenic inserts. For the two inserts, the human carboxylesterase 2 (hCE2) and human interferon beta 1 (hIFNβ1) genes were synthesized de novo.

The wild-type (WT) coding sequence (CDS) for Human carboxylesterase 2 (hCE2, 1978 base pairs, NM_003869.5; GI: 297632399) was modified to eliminate the Small XmaI and BamHI restriction sites and was placed under the control of a vaccinia virus synthetic early late promoter (pSE/L). The CDS for Human interferon beta (hIFNb, 1734 base pairs, NM_002176.2; GI: 50593016) was placed under the control of the vaccinia virus early-late promoter p7.5.

After synthesis, the two fragments were gel-purified and then ligated into the Thymidine Kinase (TK) site of the pSC65 vector (which had previously been digested to remove LacZ and then gel-purified) by GENEWIZ, Inc. (South Plainfield, N.J.) to generate the pSC65-hCE2-hIFNβ construct. The first transgene hCE2, including added 5' XmaI and 3' HindIII sequences, was digested with two restriction enzymes, XmaI and HindIII, and cloned into pSC65-LacZ (ampicillin) via 5' XmaI and 3' HindIII to make an intermediate pSC65-hCE2 construct for the next step. The second transgene hIFNβ, including added 5' HindIII and 3' BamHI sequences, was digested with two restriction enzymes, HindIII and BamHI, and cloned into pSC65-hCE2 (ampicillin) from the previous step via 5' HindIII and 3' BamHI to make the final pSC65-hCE2-hIFNβ construct.

The final construct was then prepared at a concentration of more than 1.0 ?g/uL by maxi-scale DNA preparation. Half of the maxi-scale DNA preparation was linearized with BglII to increase the efficiency of homologous recombination. The quality and quantity of the linearized construct was determined by measuring optical density (OD) at the wavelengths of 260 nm and 280 nm and by agarose gel electrophoresis. The final transfer plasmid consisted of a purified and ethanol precipitated DNA fragment.

Construction of Recombinant Vaccinia Virus

Generation of the recombinant virus was conducted following the principles of homologous recombination. The detailed procedure draws on published methods.

Selection of Functionally Active Recombinant Virus: Confirmation of Carboxylesterase and Human Interferon Activity Interferon-β expressed by recombinant vaccinia virus can be measured by monitoring the IFN-β-mediated activation of the JAK/STAT/ISGF3 pathway in a human interferon beta sensor cell line. JAK/STAT/ISGF3 stimulation in this sensor cell line subsequently induces the production of secreted alkaline phosphatase (SEAP). The level of SEAP in the suspension can be determined using the QUANTI-Blue™ system. In this system, the QUANTI-Blue™ medium turns purple/blue in the presence of SEAP, and the colorimetric change, proportional to the amount of SEAP, can be assessed through OD measurement using a spectrophotometer at 620-655 nm.

To select the clones expressing transgenic interferon-β, the isolated clone samples were analyzed with interferon sensor cells following the manufacturer's instructions. 10 ?L of sample clones were mixed with 50,000 cells/180 ?L of the sensor cell suspension in a 96-well tissue culture plate. The plate was then incubated at 37° C., 5% $CO_2$ for 48 hours. The 20 uL supernatant from HEK-Blue™ IFN ?/β sensor cells was added in a new 96-well tissue culture plate and 180 uL of QUANTI-blue solution was added. After 3 hours of incubation at 37° C., 5% $CO_2$, the SEAP level was measured using a spectrophotometer (Synergy H1 Hybrid Multi-Mode Microplate Reader, BioTek Instruments, Inc.) at 655 nm. Among 64 isolated clones, 7 clones showed positive signal (FIGS. 1A&B).

For the seven clones exhibiting interferon functionality, expression of the carboxylesterase transgene was then assessed through a carboxylesterase enzyme activity assay, using p-nitrophenyl acetate as substrate. The phenol liberated from p-nitrophenyl acetate in basic solution by the enzyme can be detected at 405 nm. Accordingly, 20 ?L from recombinant clones resuspended in 100 ?L of DMEM serum free medium was used to inoculate HeLa cells seeded 24 hours prior to infection at $5.0 \times 10^4$ cells/well in 24-well plates and incubated 48 hours at 37° C., 5% $CO_2$. Cells were harvested after washing once with phosphate buffered saline and lysed by incubating for 20 minutes on ice with 50 ?L of lysis buffer, 1.5% N-docecyl BD-Maltoside. Cell lysate was collected by centrifugation at 12,000 rpm for 10 minutes at 4° C. and resuspended in phosphate buffered saline with the 4-fold volume of lysis buffer used. 10 ?L of the cell lysate was transferred to new 96-well plates with 90 ?L of assay buffer, 50 mM p-nitrophenyl acetate dissolved in methanol. The absorbance at 405 nm was measured every 100 seconds for 10 minutes. Activity Units were calculated as the absorbance measured at 405 nm at 5 minutes after addition of pNPA assay buffer minus absorbance measured at 0 minutes.

All seven clones showed positive signal for carboxylesterase (FIGS. 1C&D) and were therefore used as seed clones for further clone purifications. Negative controls for this assay were the parental backbone virus (WR A34R K151E), a WR A34R TK− virus, and other potential recombinant clones that had been isolated for functionality testing but that were found negative for IFN-β activity. The seven clones were subjected to multiple rounds of clone purification using standard methods, which resulted in fourteen recombinant clones of which nine showed positive interferon activity using the previously described method.

TK Disruption Confirmation by PCR

Presence of interferon was confirmed by PCR product. Primers specifically targeting both flanking sides of the interferon transgene were designed, and subsequently synthesized by BIONEER, (Daejeon, Korea) (Forward:

GCCTAGATCTGTCGACTTCGAGC (SEQ ID NO: 2). Reverse: AACGTATATGTGTACCGGGAGCAG (SEQ ID NO: 3)) (FIG. 2). The reaction mixture was prepared in 500 µL tubes including 100 ng of template DNA following manufacturer's instruction (TaKaRa Ex Taq™). The tubes were put into the thermocycler (SureCycler 8800, G8800A, Agilent Technologies) pre-programmed with the typical parameters.

Example 2: In Vitro Characterization of SJ-815 Virus

Introduction

The SJ-815 virus was evaluated using in vitro cell culture assays for plaque size, viral yield, infectious particle quantity, viral protein production, infected cell morphogenesis, and extracellular envelop virion (EEV) formation.

Plaque Assays

For plaque assays, U-2 OS or BS-C-1 cell monolayers in 6-well tissue culture plates were infected with 10-fold dilutions of WR, WR.A34R, SJ-815, or mSJ-815 virus. After 2 hours of absorption, the virus inoculum was removed, the cells were washed with D-MEM or E-MEM with 2.5% FBS, and medium containing 3% methylcellulose was added. The infection was allowed to proceed for 72 or 48 hours at 37° C. The monolayer was then stained with 0.1% crystal violet for 1 hour, washed, and the plaques were counted. The observed plaque size of SJ-815 was smaller than other viruses in U-2 OS (FIGS. 3A&B and BS-C-1 cells (FIG. 3B).

OS cells had a smaller observed plaque size than BS C-1 cells. In addition, the plaque size of mSJ-815 was not reduced in human cell lines. This data suggests that components of the SJ-815 virus, particularly hIFNβ, impacted plaque formation and likely also impacted EEV release and infectivity of the virus.

SJ-815 Cytolysis and Replication in Pancreatic Cancer Cell Lines

Pancreatic and cervix cancer cell lines PANC-1, MIA PaCa-2, AsPc-1, Capan-1, Capan-2, BxPc-3 and HeLa were seeded at a concentration of 1×10$^4$ cell/well in 96-well plates in a volume of 100?L of growth media. Plates were incubated in a 37° C. incubator for 24 hours. The cells were infected with SJ-815 and WR.A34R.TK– with a multiplicity of infection dilution of 10 fold starting from 100 to 0.0001 PFU/cell. After 48 hours post-infection the cellular viability was assessed using CCK-8 (Dojindo) according to the manufacturer's instructions. The EC50 was calculated using GraphPad Prism version 5.

For viral replication (viral burst) assays, pancreatic and cervix cancer cells were seeded in 48-well plates. After 24 hours of incubation at 37° C., the cells were counted and infected with SJ-815 and WR.A34R.TK–. After 2 hours at 37° C., the inoculum was removed and the cells were washed. The cells were harvested after 48 hours post-infection. The production of infectious virus was determined by plaque assay on U-2 OS cells. SJ-815 induced stronger cytolysis (FIG. 4A) and replicated less (FIG. 4B) than the control virus in pancreatic cancer cell lines.

Of the six different pancreatic cancer cell lines tested in vitro, SJ-815 was consistently stronger than WRA34R TK– virus in three lines (BXPC-3, Capan-1 and MiaPaca-2), as indicated by a lower EC-50 in CPE assays. In addition, in one pancreatic tumor cell line (Capan-2), SJ-815 had a stronger CPE than WRA34R TK– at lower MOIs (0.001 to 0.1) and had a similar effect at higher MOIs. In a second experiment with the same cell line, SJ-815 was stronger than WRA34R TK– at the different MOIs evaluated (data not shown). Although the CPE was stronger in four tumor cell lines, the total production of infectious particles per cell was lower for SJ-815 than WRA34R TK–. SJ-815 had a stronger CPE in BXPC-3 and Capan-1 than WRA34R TK–, although the total production of PFU in these cells was lower than 20 PFU/cell. SJ-815 had a similar CPE and lower production of infectious virus than WRA34R TK– in AsPC-1 and PANC-1. Overall these results suggest that SJ-815 was more effective than WRA34R TK– virus in killing pancreatic cancer cells in vitro, even though its replication was considerably lower than WRA34R TK–.

SJ-815 Cytolysis and Replication in Colon Cancer Cell Lines

Human colon cancer cell lines HCT-116, HCT-15, HCT-8 and SW620 were seeded at a concentration of 1×10$^4$ cell/well in 96-well plates in a volume of 100?L of growth media. Plates were incubated in a 37° C. incubator for 24 hours. The cells were infected with SJ-815 and WR.A34R.TK– with a multiplicity of infection dilution of 10 fold starting from 100 to 0.0001 PFU/cell. After 48 hours post-infection the cellular viability was assessed using CCK-8 (Dojindo) according to the manufacturer's instructions. The EC50 was calculated using GraphPad Prism version 5.

For viral replication (viral burst) assays, colon cancer cells were seeded in 48-well plates. After 24 hours of incubation at 37° C., the cells were counted and infected with SJ-815 and WR.A34R.TK–. After 2 hours at 37° C., the inoculum was removed and the cells were washed. The cells were harvested after 48 hours post-infection. The production of infectious virus was determined by plaque assay on U-2 OS cells. SJ-815 induced stronger cytolysis (FIG. 5A) and replicated less (FIG. 5B) than the control virus in colon cancer cell lines.

Four colon cancer cell lines were evaluated (HCT-116, HCT-115, HCT-8 and SW620). Two cell lines (HCT-15 and HCT-8) were more resistant to the vaccinia virus infection, with HCT-15 being slightly more susceptible to the infection with SJ-815 than WR.A34R.TK–. HCT-116 and SW620 were in general more susceptible to the vaccinia virus infection, with SJ-815 demonstrating a stronger killing effect in SW620 cell lines than WR.A34R.TK virus. Despite the different susceptibility of these colon cancer cell lines to the vaccinia virus, the production of infectious particles after 48 hours post-infection was lower than 1 PFU/cell in all cases. No significant differences were observed in the production of infectious particles between SJ-185 and WR.A34R.TK– virus in the colon cancer cell lines tested. Overall this data suggests that SJ-815 was more effective than WRA34R TK– virus in killing some colon cancer cells in vitro, even though its replication was considerably lower.

SJ-815 Cytolysis and Replication in Liver Cancer Cell Lines

Human liver cancer cell lines SNU398, SNU449 and SNU739 were seeded at a concentration of 1×10$^4$ cell/well in 96-well plates in a volume of 100?L of growth media. Plates were incubated in a 37° C. incubator for 24 hours. The cells were infected with SJ-815, mSJ-815 and WR.A34R.TK– with a multiplicity of infection dilution of 10 fold starting from 10 to 0.0001 PFU/cell. After 48 hours post-infection the cellular viability was assessed using CCK-8 (Dojindo) according to the manufacturer's instructions. The EC50 was calculated using GraphPad Prism version 5.

For viral replication (viral burst) assays, liver cancer cells were seeded in 48-well plates. After 24 hours of incubation at 37° C., the cells were counted and infected with SJ-815, mSJ-815 and WR.A34R.TK−. After 2 hours at 37° C., the inoculum was removed and the cells were washed. The cells were harvested after 48 hours post-infection. The production of infectious virus was determined by plaque assay on U-2 OS cells. SJ-815 induced stronger cytolysis (FIG. 6A) and had a similar replication level (FIG. 6B) than the control virus in liver cancer cell lines.

Three liver cancer cell lines were evaluated (SNU398, SNU449 and SNU739). All three viruses had similar cytotoxicity in SNU739 and demonstrated a dose dependent effect. The virus produced in these cells was between ~10 and 20 PFU per cell, with a significant difference observed between the total virus levels produced by SJ-815, mSJ-815 and WRA34RTK−. Even though the number of infections particles produced by SJ-815 was lower, it did not impact the potency of cell killing. SJ-815 had a stronger killing effect in SNU398 and SNU449 cells and the number of virus produced after 48 hours was similar between all viruses. These results suggest that the three liver cancer cell lines evaluated were sensitive to the viral infection and that the killing effect was increased by the human interferon carried in SJ-815, as mSJ-815 did not demonstrate the same efficacy. The enhanced killing of liver cancer cell lines correlated with a higher production of infectious viral particles by the tumor cells.

SJ-815 Cytolysis and Replication in Myeloma and Melanoma Cell Lines

Human myeloma and melanoma cancer cell lines SK-MEL 5, SK-MEL 2, RPMI8226 and IM-9 cells were seeded in 96-well plates in a volume of 100 μL of growth media. Plates were incubated in a 37° C. incubator for 24 hours. The cells were infected with SJ-815, mSJ-815 and WR.A34R.TK− with 10 fold multiplicity of infection dilutions from 10 to 0.0001 PFU/cell. After 48 hours post-infection the cellular viability was assessed using CCK-8 (Dojindo) according to the manufacturer's instructions. The production of infectious virus was determined by plaque assay on U-2 OS cells. SJ-815 induced stronger cytolysis in some myeloma and melanoma cells than the control virus, as indicated by decreased cell viability in cell lines SK-MEL 5 (FIG. 7A), SK-MEL 2 (FIG. 7B), RPMI8226 (FIG. 7C) and IM-9 (FIG. 7D).

For viral replication (viral burst) assays, myeloma (RPMI8226 and IM-9) and melanoma (SK-MEL 5 and SK-MEL 2) cancer cells were seeded in 48-well plates. After 24 hours of incubation at 37° C., the cells were counted and infected with 1 pfu/cell of SJ-815, mSJ-815 and WR.A34R.TK−. The cells were incubated at 37° C. in 5% $CO_2$ incubator and harvested after 48 hours post-infection. SJ-815 replicated less than the control virus in some myeloma and melanoma cancer cell lines (FIG. 8).

Two melanoma cancer cell lines were evaluated (SK-MEL 2 and SK-MEL 5). The viruses demonstrated similar cytotoxicity in SK-MEL 5 and a dose dependent effect was observed (FIG. 8). The virus produced in these cells was ~0.10 PFU per cell, and there were no significant differences in the total viral production between the different viruses tested. SJ-815 demonstrated a stronger killing effect in SK-MEL 2 cells (FIG. 8) and there was no difference in the viral production after 48 hours post infection between SJ-815 and WR.A34R.TK− virus. The number of infectious particles produced in SK-MEL2 cells was higher than the number produced in SK-MEL 5 cells. RPMI2886 and IM-9 myeloma cells (B lymphocytes) were susceptible to the virus killing (FIG. 8). However RPMI2886 was more susceptible to SJ-815 than mSJ-815 and WRA34RTK− 9 (FIG. 8).

Interestingly there was a significant difference observed in the total amount of SJ-815 infectious particles produced in the cancer cells as compared to the control WR.A34R.TK− virus. Suspension cells were harder to infect, leading to lower overall viral recovery after infection with 1 PFU per cell. Overall these results suggest that SJ-815 was more effective than WRA34R TK− virus at killing some melanoma and myeloma cancer cells in vitro, even though its replication was considerably lower than WRA34R TK− in some instances.

SJ-815 Cytolysis and Replication in Murine Cancer Cell Lines

Mouse cancer cell lines TIB-75, CT-26, B16-F10, MC-38, RENCA and 4T1 were seeded in 96-well plates in a volume of 100?L of growth media. Plates were incubated in a 37° C. incubator for 24 hour. The cells were infected with mSJ-815 and WR.mGMCSF.TK− with 10 fold dilutions of multiplicity of infection from 100 to 0.0001 PFU/cell. After 48 hours post-infection the cellular viability was assessed using Cyto Tox-Glo assay (Promega) according to the manufacturer's instructions. Increasing concentrations of mSJ-815 virus induced cytolysis in some murine cancer cell lines including TIB-75 hepatocellular carcinoma (FIG. 9A), CT-26 colon carcinoma (FIG. 9B), B16-F10 skin melanoma (FIG. 9C), MC-38 colon carcinoma (FIG. 9D), RENCA renal adenocarcinoma (FIG. 9E), and 4T1 breast cancer (FIG. 9F).

Example 3: In-Vivo Characterization of SJ-815 Virus Efficacy and Toxicity

Introduction

The SJ-815 virus was evaluated in-vivo by measuring the impact of murine SJ-815 viral administration, both alone and in combination with irinotecan treatment, on tumor growth, animal survival, and organ weight.

MC-38 Murine Colon Carcinoma Growth

C57BL/6 mice were implanted subcutaneously with MC-38 mouse colon cancer cells ($2 \times 10^6$ cells per mouse). Once tumors had formed (100-200 mm³), mice were randomized into 4 treatment groups (n=5 mice/group): (1) Phosphate buffered saline (PBS) alone, (2) WR.TK−.mG-MCSF (four intravenous administrations of $1 \times 10^8$ pfu given every three days), (3) WR.TK−.mGMCSF (same schedule as 2 via intratumoral), and (4) treatment with mSJ-815 with the same treatment schedule as referenced and control administered via intratumoral. Subsequent tumor burden was followed by caliper measurement and mice were sacrificed when their tumor reached 1,500 mm³. Mice were weighted every 2 days per week. Data analysis was performed using graphpad prism version 5. MC-38 murine colon carcinoma growth was delayed by treatment with mSJ-815, as indicated by decreased tumor size at days 21, 24, and 27 (FIG. 10C). No significant changes were observed in survival or body weight (FIGS. 10A&B).

The tumor growth rate of MC38 cells in C57BL/6 mice was evaluated. Mice were treated on day 13 after tumor cell injection at an average tumor size of 100 mm³. At 27 days after treatment, most of the groups reached a tumor size average of 1500 mm³. The effect on tumor growth and overall survival of JX-594 and SJ-815 treatment was evaluated. There was no significant difference in survival between the control and treated groups. However there was a significant difference in tumor size between the PBS and mSJ-815 treated group at days 21, 24 and 27. Administering the treatment IV versus IT was evaluated using WR.mG-MCSF and no significant different in tumor size was observed. Overall, the group treated with mSJ-815 had an increase tumor reduction compared to WRmGMCSF.

MIA PaCa-2 Human Pancreatic Carcinoma Growth

Female nude mice were injected with MIA PaCa-2 human pancreatic cancer cells subcutaneously and developed tumors. Once tumors reached a volume between 100 to 200 mm$^3$, mice were randomized into 8 treatment groups (n=3 mice/group): (1) Phosphate buffered saline (PBS), (2) SJ-815 ($1 \times 10^5$), (3) SJ-815 ($1 \times 10^6$), (4) SJ-815 ($1 \times 10^7$) administered intratumoral once per week (Days 0, 7 and 14), (5) CPT-11 (0.25 mg/kg), (6) CPT-11 (2.5 mg/kg), (7) CPT-11 (25 mg/kg) administered intravenous on days 3, 10 and 17, (8) SJ-815 ($1 \times 10^6$)+CPT-11 (25 mg/kg). Tumor measurements were performed with calipers twice per week through the endpoint. MIA PaCa-2 human pancreatic carcinoma growth was delayed by combination treatment with mSJ-815 and CPT-11 (irinotecan), as indicated by a decreased average tumor volume (FIG. 11). This experiment shows that the expression of the carboxylesterase enzyme in combination with a topoisomerase inhibitor was having the desired effect independent of the cytokine (hIFN-b) since the nude mice have an inhibited immune system due to the near lack of T cells. Even if the human IFN-b could be affecting the mouse immune system, the nude mice should be even less capable of responding to the IFN-b.

These data suggest that the virus monotherapy demonstrated a trend towards increased potency as compared to irinotecan monotherapy. Combination therapy similarly demonstrated a trend towards increased potency than either monotherapy. Within the monotherapy groups, the highest doses generated the highest anti-tumor responses. Systemic delivery of virus to tumors generated an anti-tumor response comparable to that seen in directly injected tumors, suggesting that the IV route may be as effective as the IT route.

Survival of B57B116 Mice Harboring B16-F10 Melanoma Tumors

Female C57BL/6 mice were implanted subcutaneously with B16-F10 mouse melanoma cells ($1 \times 10^5$ cells per mouse). Once tumors had formed (50-100 mm$^3$), mice were randomized into 5 treatment groups (n=5 mice/group): (1) Phosphate buffered saline (PBS), (2) mSJ-815 ($1 \times 10^6$) 1 dose at Day 0, (3) mSJ-815 ($1 \times 10^7$) 1 dose at Day 0, (4) mSJ-815 ($1 \times 10^8$) 1 dose at Day 0 and (5)) mSJ-815 ($1 \times 10^6$) 3 doses at Day 0, 7 and 14 intratumoral. Subsequent tumor burden was followed by caliper measurement and mice were sacrificed when their tumors reached 1,500 mm$^3$. Mice were weighted twice per week. Data analysis was performed using graphpad prism version 5. Survival of B57BL/6 mice harboring B16-F10 melanoma tumors was significantly enhanced by treatment with mSJ-815 (FIG. 12A).

Body weight data was analyzed by one-way analysis of variance (ANOVA) followed by Dunnett's multiple comparison test (FIG. 12B). The data was statistically significant with a P=0.0267. There was no significant difference between the different groups with Dunnett's multiple comparison test. Homogeneity of variance was determined using Bartlett's test, which indicated that the variances were not significant with a P=0.3973.

B16-F10 Melanoma Tumor Growth with Intratumoral mSJ-815

Female C57BL/6 mice were implanted subcutaneously with B16-F10 mouse melanoma cells ($1 \times 10^5$ cells per mouse). Once tumors had formed (50-100 mm$^3$), mice were randomized into 5 treatment groups (n=5 mice/group): (1) Phosphate buffered saline (PBS), (2) mSJ-815 ($1 \times 10^6$) 1 dose at Day 0, (3) mSJ-815 ($1 \times 10^7$) 1 dose at Day 0, (4) mSJ-815815 ($1 \times 10^8$) 1 dose at Day 0 and (5)) mSJ-815 ($1 \times 10^6$) 3 doses at Day 0, 7 and 14 intratumoral. Subsequent tumor burden was followed by caliper measurement and mice were sacrificed when their tumors reached 1,500 mm$^3$. Data analysis was performed using graphpad prism version 5. B16-F10 melanoma tumor growth was delayed by combination treatment with mSJ-815, as indicated by a decreased tumor volume (FIGS. 13A&B).

The average tumor size per group was calculated and the SEM was plotted. The difference in the tendency of the plots was due to animals that were sacrificed. Data was analyzed by One-way analysis of variance (ANOVA) followed by Dunnett's multiple comparison test and unpaired t test. The data was not statistically significant with a P=0.3755. Homogeneity of variance was determined using Bartlett's test which indicated that the variances were significantly different with a P=0.0247. By unpaired T test the data was not significantly different. If the data was analyzed at day 12, which corresponded to the day at which animals from the PBS group reached the maximum tumor size and were sacrificed, the data was statistically different by one-way ANOVA with a P=0.0119. At this time point, all groups were statistically different from the PBS group by Dunnett's multiple comparison test (P<0.05). A significant difference was observed between PBS and mSJ-815 (3e7) by unpaired t test with a P=0.0434.

Survival of B57BL/6 Mice Harboring B16-F10 Melanoma Tumors

Female C57BL/6 mice were implanted subcutaneously with B16-F10 mouse melanoma cells ($1 \times 10^5$ cells per mouse). Once tumors had formed (50-100 mm$^3$), mice were randomized into 8 treatment groups (n=8 mice/group): (1) Phosphate buffered saline (PBS), (2) WR.A34R.TK– labeled as WR.TK– (3) SJ-815, (4) mSJ-815 delivered via intratumoral, (5) mSJ-815 delivered via intravenous, (6) PBS+CPT-11, (7) WR.TK–+CPT-11 and (8) mSJ-815+CPT-11. All the viruses were delivered intratumoral except group 5 where mSJ-815 was delivered via an intravenous route, with three treatments of $1 \times 10^7$ PFU administered on days 0, 7 and 14. 25 mg/kg of CPT-11 was delivered intravenously on days 3, 9 and 17. Survival was assessed every day after treatment. Data analysis was performed using graphpad prism version 5. Survival of B57BL/6 mice harboring B16-F10 melanoma tumors was significantly enhanced by combination treatment with mSJ-815 and CPT-11 (Irinotecan). Kaplan-Meier survival curve were produced (FIG. 14). The data was analyzed by Long-rank (Mantel-Cox) Test, and was significantly different with a P<0.0001. P values were also calculated by Log-rank (Matel-Cox) test for between-group comparisons. The statistically significant P-values were calculated as follow: G1 vs G2 P=0.0166, G1 vs G4 P=0.0025, G2 vs G4 P=0.0199, G6 vs G7 P=0.0053, G6 vs G8 P=0.0007, G7 vs G8 P=0.0022. G4 vs G8 was not statistically different.

B16-F10 Melanoma Tumor Growth with Intratumoral Combination Treatment with mSJ-815 and Irinotecan Female C57BL/6 mice were implanted subcutaneously with B16-F10 mouse melanoma cells ($1 \times 10^5$ cells per mouse). Once tumors had formed (50-100 mm$^3$), mice were randomized into 8 treatment groups (n=8 mice/group): (1) Phosphate buffered saline (PBS), (2) WR.A34R.TK– labeled as WR.TK– (3) SJ-815, (4) mSJ-815 delivered via intratumoral, (5) mSJ-815 delivered via intravenous, (6) PBS+CPT-11, (7) WR.TK–+CPT-11 and (8) mSJ-815+CPT-11. All the viruses were delivered intratumoral except group 5 where mSJ-815 was delivered via an intravenous route, with three treatments of $1 \times 10^7$ PFU administered on days 0, 7 and 14. 25 mg/kg of CPT-11 was delivered intravenously on days 3, 9 and 17. Subsequent tumor burden was followed by caliper measurement and mice were sacrificed when their tumors reached 1,500 mm³. Data analysis was performed using graphpad prism version 5. One mouse died during the experiment. The tumor volume values from the dead mouse were excluded from FIGS. 15A&B and included in FIGS. 15C&D. FIGS. 15A&B show dips in the tumor volume, which represent artifacts due to exclusion of the tumor volume values from the dead mouse. Conversely, FIGS. 15C&D include the tumor volume values from the dead mouse and no dips are observed. These data indicate that treatment with an oncolytic vaccinia virus, with or without a topoisomerase inhibitor, delayed tumor growth.

Overall, the oncolytic vaccinia virus that did not express a carboxylesterase enzyme, WR.TK−, showed no improvement when combined with a topoisomerase inhibitor indicating that there is no natural improvement when combining an oncolytic vaccinia virus with a topoisomerase inhibitor. Similarly, the WR.TK− virus produced similar results as the SJ-815 showing that neither expression of a carboxylesterase without a topoisomerase inhibitor nor expression of a human cytokine (not expected to significantly impact the mouse immune system) improve the effectiveness. On the other hand, expression of the murine cytokine improved the outcome as compared to the WR.TK− virus. Addition of the topoisomerase shows promising signs of further improvement overall. The average tumor size per group was calculated and the SEM was plotted. The data was analyzed by unpaired T test for between-group analysis at different days of tumor measurement. The following combinations showed statistically significant differences: G1 vs G2 (D9) P=0.052, (D13) P=0.032; G1 vs G3 (D9) P=0.027, (D13) P=0.0097; G1 vs G4 (D13) P=0.012; G6 vs G7 (D9) P=0.027, (D13) P=0.0105 and G6 vs G8 (D6) P=0.067, (D9) P=0.011, (D13) P=0.004.

Body Weight in Animals Treated with Vaccinia Virus Alone or in Combination with Irinotecan Female C57BL/6 mice were implanted subcutaneously with B16-F10 mouse melanoma cells ($1\times10^5$ cells per mouse). Once tumors had formed (50-100 mm³), mice were randomized into 8 treatment groups (n=8 mice/group): (1) Phosphate buffered saline (PBS), (2) WR.A34R.TK− labeled as WR.TK− (3) SJ-815, (4) mSJ-815 delivered via intratumoral, (5) mSJ-815 delivered via intravenous, (6) PBS+CPT-11, (7) WR.TK−+CPT-11 and (8) mSJ-815+CPT-11. All the viruses were delivered intratumoral except group 5 where mSJ-815 was delivered via an intravenous route, with three treatments of $1\times10^7$ PFU administered on days 0, 7 and 14. 25 mg/kg of CPT-11 was delivered intravenously on days 3, 9 and 17. Mice were weighted twice per week. Data analysis was performed using graphpad prism version 5. No significant body weight loss and therefore toxicity was observed in animals treated with vaccinia virus alone or in combination with Irinotecan (FIG. 16).

Weight Variation in Major Organs in Animals Treated with mSJ-815

Female C57BL/6 mice were implanted subcutaneously with B16-F10 mouse melanoma cells ($1\times10^5$ cells per mouse). Once tumors had formed (50-100 mm³), mice were randomized and treated intratumoral or intravenous with mSJ-815. Liver, kidney, brain and lungs were collected and weighted at the end point for each animal. The data was normalized against each animal's body weight. Data analysis was performed using graphpad prism version 5. No significant weight variation in liver (FIG. 17A), kidney (FIG. 17B), brain (FIG. 17C), or lung (FIG. 17D) was detected in animals treated with mSJ-815 intratumoral or intravenous.

Spleen Weight with IT and IV Treatment with mSJ-815

Female C57BL/6 mice were implanted subcutaneously with B16-F10 mouse melanoma cells ($1\times10^5$ cells per mouse). Once tumors had formed (50-100 mm³), mice were randomized and treated intratumoral or intravenous with mSJ-815. Spleens were collected and weighted at the end point for each animal. The data was normalized against each animal's body weight. Data analysis was performed using graphpad prism version 5. Spleen weight increased with IV (FIG. 18A) and IT (FIG. 18B) treatment with mSJ-815 and normal spleen weight was recovered after time.

Virus Quantitation within Tumors and Organs

On the day of animal death tumor, muscle, ovaries and liver were removed, placed in 2 mL of balanced salt solution containing 0.1% bovine serum albumin, and immediately stored at −80° C. until further use. Organs were thawed and homogenized with a Bead Ruptor 24 Homogenizer (OMNI International) using 1.5 mL tubes with 1.4 mm size ceramic beads. Tissue homogenates were sonicated for 45 seconds intervals in tubes immersed in ice water and then centrifuged for 10 seconds at 400×g in a microcentrifuge Sorvall Legend Micro 17R. Supernatants were aliquoted and virus titers were determined by plaque assay on. U-2 OS cells. Viral levels were higher within tumors as compared to levels within muscle, ovaries, and liver. Virus was found predominantly within tumors but not organs at later timepoints (FIG. 19).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A composition comprising a recombinant Western Reserve strain oncolytic vaccinia virus that expresses a cytokine and a carboxylesterase enzyme and that does not express an active thymidine kinase, wherein the cytokine is interferon-beta-1 and the carboxylesterase enzyme is CES2 and wherein the recombinant Western Reserve strain oncolytic vaccinia virus comprises a functional B18R gene.

2. The composition of claim 1, wherein the vaccinia virus does not express an active vaccinia growth factor (VGF) gene and/or expresses one or more of the following: a granulocyte-macrophage colony-stimulating factor (GM-CSF), a cytosine deaminase protein, and somatostatin receptor type 2 protein.

3. The composition of claim 1, wherein the vaccinia virus is the Western Reserve strain, the carboxylesterase is a human CES2 enzyme with a C-terminal retention sequence, and the cytokine is human interferon-beta-1.

4. The composition of claim 3, wherein the recombinant vaccinia virus further comprises an A34R gene comprising a K151E mutation.

5. The composition of claim 1, wherein the composition comprises between $1\times10^6$ and $1\times10^{12}$ plaque forming units (pfu).

6. The composition of claim 1, further comprising an agent suitable for active embolization.

7. A method for treating cancer in a mammal, comprising administering to the mammal an effective amount of the composition of claim 1.

8. The method of claim 7, wherein the cancer is colorectal cancer, lung cancer, melanoma, pancreatic cancer, ovarian cancer, cervical cancer or liver cancer.

9. The method of claim 7, wherein the cancer is refractory to treatment with one or more chemotherapeutic agents, a topoisomerase inhibitor, fluoropyrimidine and oxaliplatin, cetuximab and/or panitumumab, and/or is refractory to treatment with one or more antibodies.

10. The method of claim 7, wherein the oncolytic vaccinia virus is administered intratumorally or intravenously at one or more doses of between $1\times10^6$ and $1\times10^{12}$ plaque forming units (pfu).

11. The method of claim 7, her comprising administering to the mammal one or more additional anti-cancer agents selected from 5-fluorouracil (FU), folinic acid (FA), methotrexate, capecitabine, oxaliplatin, bevacizumab, cetuximab and any combination thereof.

12. The method of claim 7, wherein the (a) composition comprising the recombinant oncolytic vaccinia virus is part of an effective amount of a combination further comprising (b) a cancer co-drug.

13. The method of claim 12, wherein the cancer co-drug is a topoisomerase inhibitor or irinotecan.

14. The method of claim 12, wherein the cancer co-drug is an activatable cancer co-drug, an activatable topoisomerase inhibitor, paclitaxel-2-ethylcarbonate (which is converted to paclitaxel), capecitabine (which is converted to 5'-Deoxy-5-fluorocytidine (5-FU)), and any tertiary amidomethyl ester prodrugs of existing chemotherapeutics.

15. The method of claim 12, wherein (a) and (b) are administered in synergistically effective amounts and/or are sequentially, simultaneously or separately administered and/or are coadministered to the mammal in the same or different formulations.

16. The method of claim 12, wherein a first dose of oncolytic vaccinia virus is administered prior to a first dose of cancer co-drug.

17. The method of claim 12, wherein the oncolytic vaccinia virus is administered weekly or every other week and wherein the cancer co-drug is administered every other week.

18. The method of claim 7, wherein the administration of the composition comprises introducing the composition into the vasculature of a mammal, wherein the composition comprises an agent suitable for active embolization.

19. The method of claim 7, wherein the mammal is a human.

20. The method of claim 12, wherein administration of the cancer co-drug is initiated one to three days after the second weekly dose of the oncolytic vaccinia virus.

21. The composition of claim 1, wherein the recombinant vaccinia virus does not express a GM-CSF.

* * * * *